US008003689B2

(12) United States Patent
Veverka

(10) Patent No.: US 8,003,689 B2
(45) Date of Patent: Aug. 23, 2011

(54) METABOLITES OF SELECTIVE ANDROGEN RECEPTOR MODULATORS AND METHODS OF USE THEREOF

(75) Inventor: Karen A. Veverka, Cordova, TN (US)

(73) Assignee: GTx, Inc., Memphis, TN (US)

(*) Notice: Subject to any disclaimer, the term of this patent is extended or adjusted under 35 U.S.C. 154(b) by 0 days.

(21) Appl. No.: 12/487,769

(22) Filed: Jun. 19, 2009

(65) Prior Publication Data

US 2010/0004326 A1 Jan. 7, 2010

Related U.S. Application Data

(60) Provisional application No. 61/129,357, filed on Jun. 20, 2008, provisional application No. 61/100,169, filed on Sep. 25, 2008.

(51) Int. Cl.
*A61K 31/35* (2006.01)
*A61K 31/24* (2006.01)
*A61K 31/165* (2006.01)
*C07C 237/00* (2006.01)
*C07C 229/00* (2006.01)
*C07D 315/00* (2006.01)

(52) U.S. Cl. ........ 514/459; 514/538; 514/620; 549/417; 560/42; 564/164

(58) Field of Classification Search .................. 514/459, 514/538, 620; 549/417; 560/42; 564/164
See application file for complete search history.

(56) References Cited

U.S. PATENT DOCUMENTS

| | | |
|---|---|---|
| 3,239,345 A | 3/1966 | Hodge et al. |
| 3,865,801 A | 2/1975 | Chiba et al. |
| 4,036,979 A | 7/1977 | Asato |
| 4,411,890 A | 10/1983 | Momany |
| 5,179,080 A | 1/1993 | Rothkopf |
| 5,441,868 A | 8/1995 | Lin et al. |
| 5,547,933 A | 8/1996 | Lin et al. |
| 5,552,412 A | 9/1996 | Cameron et al. |
| 5,618,698 A | 4/1997 | Lin et al. |
| 5,621,080 A | 4/1997 | Lin et al. |
| 6,019,957 A | 2/2000 | Miller et al. |
| 2003/0086848 A1 | 5/2003 | Saccomanno |
| 2004/0214790 A1 | 10/2004 | Borgens |
| 2005/0038110 A1* | 2/2005 | Steiner et al. ............ 514/493 |
| 2006/0035966 A1 | 2/2006 | Dalton et al. |
| 2007/0161608 A1 | 7/2007 | Dalton et al. |

FOREIGN PATENT DOCUMENTS

| | | |
|---|---|---|
| EP | 0 668 351 | 10/1990 |
| WO | WO 89/07110 | 8/1989 |
| WO | WO 89/07111 | 8/1989 |
| WO | WO 91/05867 | 5/1991 |
| WO | WO 93/04081 | 3/1993 |
| WO | WO 01/68603 | 9/2001 |
| WO | WO 2005/113565 | 10/2005 |
| WO | WO 2005113565 A2 * | 12/2005 |

OTHER PUBLICATIONS

U.S. Appl. No. 09/519,079, filed Mar. 6, 2000, Robl et al.
Matsumoto. "Hormonal therapy of male hypogonadism." Endocrinol. Met. Clin. N. Am. 23:857-75 (1994).
Zhou et al. "Specificity of ligand-dependent androgen receptor stabilization: receptor domain interactions influence ligand dissociation and receptor stability." Molec. Endocrinol. 9:208-18 (1995).
Sundaram et al. "7a-Methyl-Nortestosterone (MENT): The Optimal Androgen for Male Contraception" (Annals of Medicine 25: 199-205, (1993).
Thevis et al. "Screening for metabolically stable aryl-propionamide-derived selective androgen receptor modulators for doping control purposes" Rapid Communications in Mass Spectrometry vol. 20, Issue 5, pp. 870-876, Mar. 15, 2006.
Thevis et al. "Screening for 2-quinolinone-derived selective androgen receptor agonists in doping control analysis" Rapid Commun Mass Spectrom. ;21(21):3477-86. (2007).
Thevis et al. "New drugs and methods of doping and manipulation" Drug Discovery Today vol. 13, Issues 1-2, pp. 59-66 , Jan. 2008.
Kuuranne et al. "Aryl-propionamide-derived selective androgen receptor modulators: liquid chromatography-tandem mass spectrometry characterization of the in vitro synthesized metabolites for doping control purposes" Drug Metab Dispos. 36(3):571-81, Mar. 2008.
Singh et al. "Androgens stimulate myogenic differentiation and inhibit adipogenesis in C3H 10T1/2 pluripotent cells through an androgen receptor-mediated pathway" Endocrinology. 144(11):5081-8, Nov. 2003.
Langer. "New methods of drug delivery" Science 28: vol. 249 No. 4976 pp. 1527-1533, Sep. 1990.
Treat et al. "In Liposomes in the Therapy of Infectious Disease and Cancer" Lopez-Berestein and Fidler (eds.), Liss, New York, pp. 353-365 (1989).
Lopez-Berestein in Liposomes in the Therapy of Infectious Disease and Cancer, Lopez-Berestein and Fidler (eds.), Liss, New York, pp. 317-327. (1984).
Sefton, CRC Crit. Ref. Biomed. Eng. 14:201 (1987).
Buchwald et al. "Long-term, continuous intravenous heparin administration by an implantable infusion pump in ambulatory patients with recurrent venous thrombosis." Surgery 88:507 (1980).
Saudek et al."A preliminary trial of the programmable implantable medication system for insulin delivery." N. Engl. J. Med. 321:574 (1989).
Goodson, in Medical Applications of Controlled Release, supra, vol. 2, pp. 115-138 (1984).
Abuchowski et al. "Immunosuppressive properties and circulating life of Achromobacter glutaminase-asparaginase covalently attached to polyethylene glycol in man" Cancer Treat Rep. 65(11-12):1077-81. Nov.-Dec. 1981.
Katre et al. "Chemical modification of recombinant interleukin 2 by polyethylene glycol increases its potency in the murine Meth A sarcoma model" Proc Natl Acad Sci U S A. 84(6):1487-91. Mar. 1987.
Edwards et al. "Nonsteroidal androgen receptor agonists based on 4-(trifluoromethyl)-2H-pyrano[3,2-g]quinolin-2-one" Bioorg. Med. Chem. Lett., 9: 1003-1008, (1999).

(Continued)

*Primary Examiner* — Yong Chu
(74) *Attorney, Agent, or Firm* — Mark S. Cohen; Pearl Cohen Zedek Latzer, LLP

(57) ABSTRACT

This invention provides metabolites of SARM compounds including inter alia glucuronidated metabolites and uses thereof in treating a variety of diseases or conditions in a subject, including, inter alia, muscle wasting disease and/or disorder, a bone related disease and/or disorder, metabolic syndrome, diabetes and associated diseases, and others.

2 Claims, 48 Drawing Sheets

OTHER PUBLICATIONS

Hamann et al. "Discovery of a potent, orally active nonsteroidal androgen receptor agonist: 4-ethyl-1,2,3,4-tetrahydro-6-(trifluoromethyl)-8-pyridono[5,6-g]-quinoline (LG121071)" J. Med. Chem., 42:210-212, (1999).

Roymans et al. Expression and Induction Potential of Cytochromes P450 in Human Cryopreserved Hepatocytes Drug Metab. Dispos., 33(7), 1004-1016, (2005).

International Search Report of Application No. PCT/US 09/47892 Date of Mailing Sep. 16, 2009.

* cited by examiner

But intensity of metabolite m/z 530 is significantly lower at time=1min than time=120min.

METABOLITES OF SELECTIVE ANDROGEN RECEPTOR MODULATORS AND METHODS OF USE THEREOF

CROSS REFERENCE TO RELATED APPLICATIONS

This application claims the benefit of U.S. Provisional Application Ser. No. 61/129,357 filed on Jun. 20, 2008 and of U.S. Provisional Application Ser. No. 61/100,169 filed on Sep. 25, 2008 which are incorporated in their entirety herein by reference.

FIELD OF INVENTION

This invention provides metabolites of SARM compounds including inter alia, glucuronidated metabolites, uses thereof in treating a variety of diseases or conditions and methods of detection in a subject, including, inter alia, muscle wasting disease and/or disorder, a bone related disease and/or disorder, metabolic syndrome, diabetes and associated diseases, and others. This invention also relates to methods of detection of metabolites of SARM compounds.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids which are produced in the body by the testes and the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857-75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., Molec. Endocrinol. 9:208-18 (1995)). Other steroidal androgens include esters of testosterone, such as the cypionate, propionate, phenylpropionate, cyclopentylpropionate, isocarprate, enanthate, and decanoate esters, and other synthetic androgens such as 7-Methyl-Nortestosterone ("MENT") and its acetate ester (Sundaram et al., "7 Alpha-Methyl-Nortestosterone(MENT): The Optimal Androgen For Male Contraception," Ann. Med., 25:199-205 (1993) ("Sundaram")). Because the AR is involved in male sexual development and function, the AR is a likely target for effecting male contraception or other forms of hormone replacement therapy.

Selective androgen receptor modulator (SARM) compound metabolites, either alone or as a composition, are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, hair loss, anemia, obesity, sarcopenia, osteopenia, osteoporosis, benign prostate hyperplasia, alterations in mood and cognition and prostate cancer; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; and/or g) decreasing the incidence of, halting or causing a regression of prostate cancer.

SUMMARY OF THE INVENTION

In one embodiment, this invention provides a metabolite of a selective androgen receptor modulator (SARM) compound, wherein said SARM is represented by the structure of formula I:

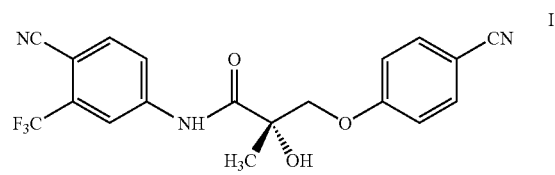

In another embodiment, the metabolite of the selective androgen receptor modulator of structure I, is represented by the structure:

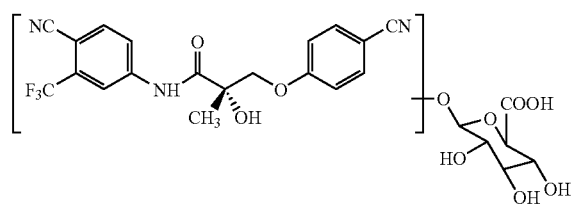

In another embodiment, the metabolite of the selective androgen receptor modulator of structure I, is represented by the structure:

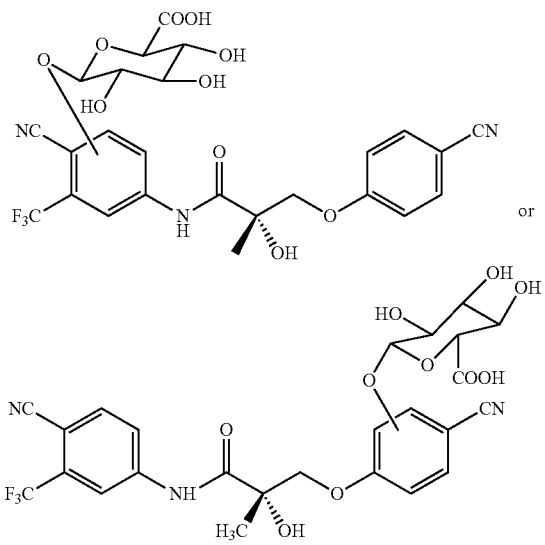

In another embodiment, the metabolite of the selective androgen receptor modulator of structure I, is represented by the structure:

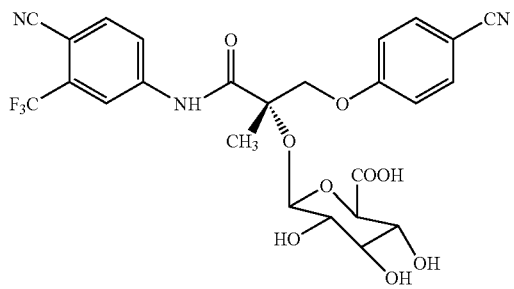

In another embodiment, the metabolite of the selective androgen receptor modulator of structure I, is represented by the structure:

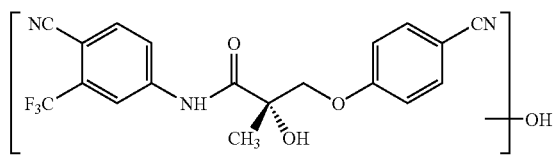

In another embodiment, the metabolite of the selective androgen receptor modulator of structure I, is represented by the structure:

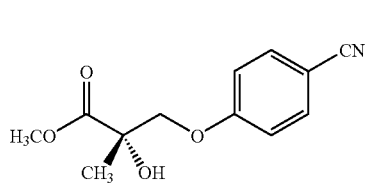

In another embodiment, the metabolite of the selective androgen receptor modulator of structure I, is represented by the structure:

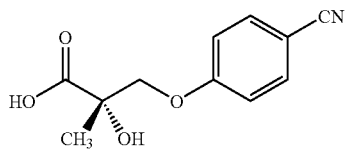

In another embodiment, this invention provides a metabolite of a selective androgen receptor modulator (SARM) compound, wherein said SARM is represented by the structure of formula II:

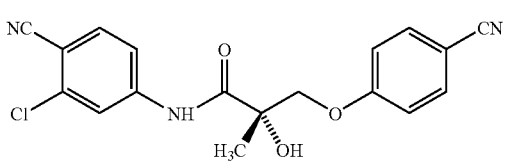

In another embodiment, the metabolite of the selective androgen receptor modulator of structure II, is represented by the structure:

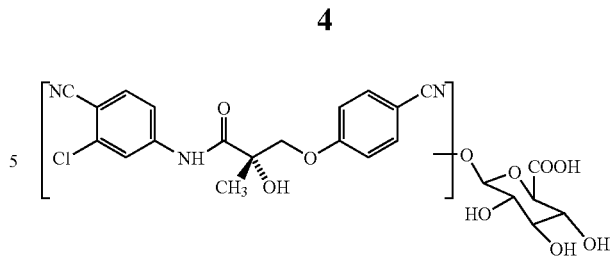

In another embodiment, the metabolite of the selective androgen receptor modulator of structure II, is represented by the structure:

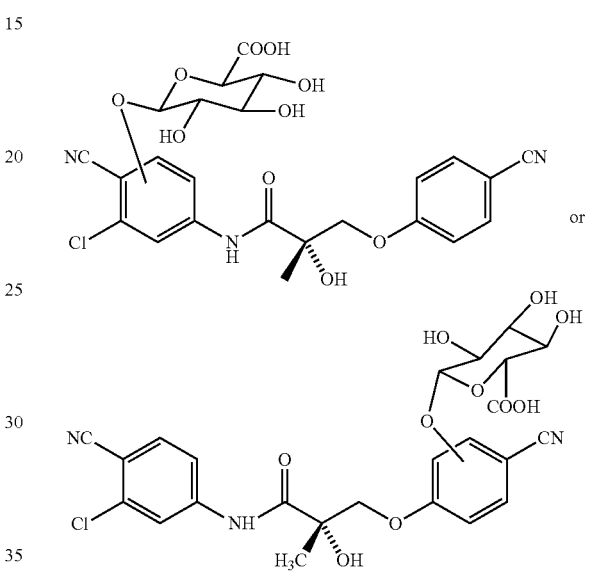

or

In another embodiment, the metabolite of the selective androgen receptor modulator of structure II, is represented by the structure:

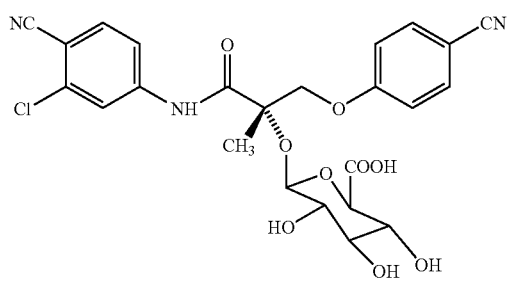

In another embodiment, the metabolite of the selective androgen receptor modulator of structure II, is represented by the structure:

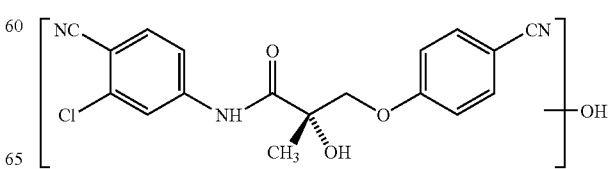

In another embodiment, the metabolite of the selective androgen receptor modulator of structure II, is represented by the structure:

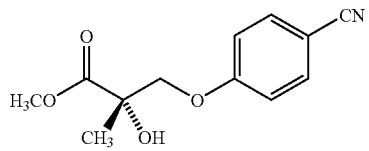

In another embodiment, the metabolite of the selective androgen receptor modulator of structure II, is represented by the structure:

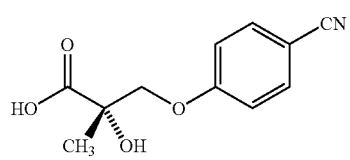

In one embodiment, this invention provides a composition comprising a metabolite of the selective androgen receptor modulator structure I-IV and a suitable carrier or diluents.

In one embodiment, this invention provides a method of detecting a metabolite of a compound of formula III,

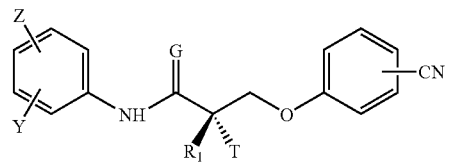

wherein
G is O or S;
T is OH, OR, —NHCOCH$_3$, or NHCOR;
Z is NO$_2$, CN, COOH, COR, NHCOR or CONHR;
Y is CF$_3$, alkyl, F, I, Br, Cl, CN, C(R)$_3$ or Sn(R)$_3$;
R is hydrogen, alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH; and
R$_1$ is CH$_3$, CH$_2$F, CHF$_2$, CF$_3$, CH$_2$CH$_3$, or CF$_2$CF$_3$;
said method comprising the step of:
incorporating $^{13}$C, $^{14}$C, $^{15}$N, $^{18}$O, $^{2}$H, $^{3}$H or any combination thereof in said compound and detecting a metabolite of said compound by spectroscopy, whereby a metabolite of said compound exhibits different spectroscopic characteristics than a compound of formula III.

In one embodiment, incorporating results in a compound represented by the following structure:

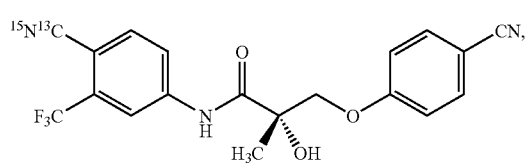

or in some embodiments, incorporating results in a compound represented by the following structure:

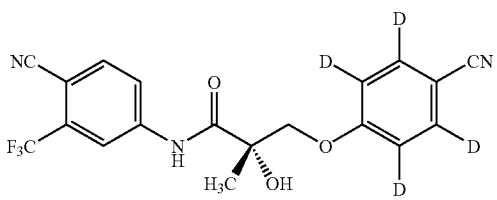

wherein D represents $^2$H; or in some embodiments, incorporating results in a compound represented by the following structure:

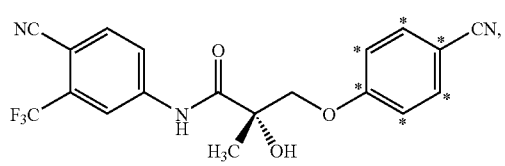

wherein the asterisk represents $^{14}$C incorporation; or in some embodiments, incorporating results in a compound represented by the following structure:

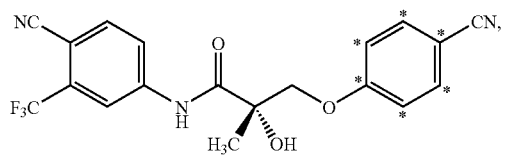

or in some embodiments, incorporating results in a compound represented by the following structure:

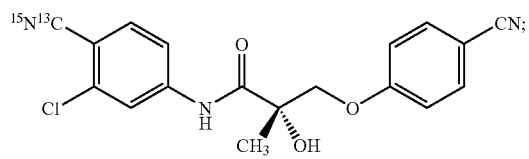

wherein D represents $^2$H; or in some embodiments, incorporating results in a compound represented by the following structure:

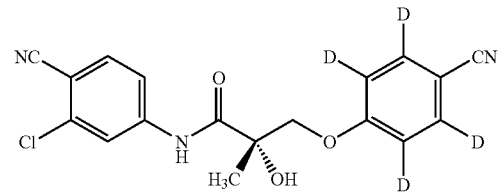

wherein the asterisk represents $^{14}$C incorporation.

In one embodiment, this invention provides a compound represented by the following structure:

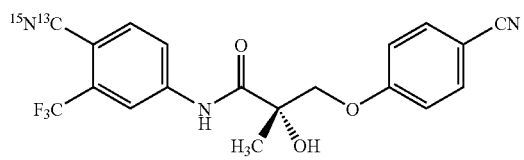

In one embodiment, this invention provides a compound represented by the following structure:

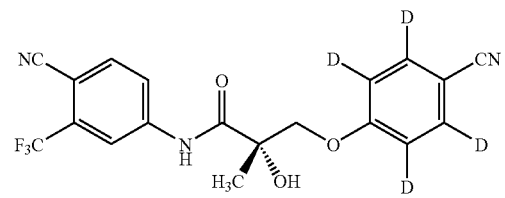

wherein D represents $^2$H.

In one embodiment, this invention provides a compound represented by the following structure:

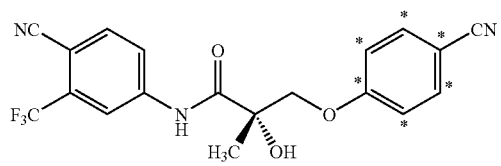

wherein the asterisk represents $^{14}$C incorporation.

In one embodiment, this invention provides a compound represented by the following structure:

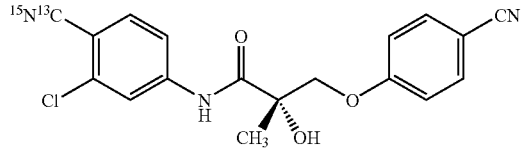

In one embodiment, this invention provides a compound represented by the following structure:

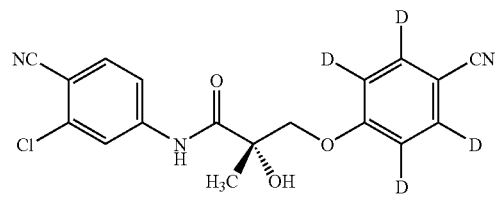

wherein D represents $^2$H.

In one embodiment, this invention provides a compound represented by the following structure:

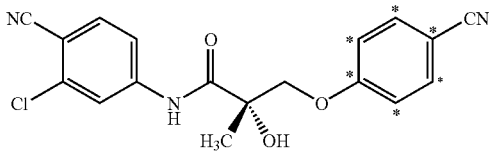

wherein the asterisk represents $^{14}$C incorporation.

In some embodiments, this invention provides a process for the preparation of a labeled compound of formula III:

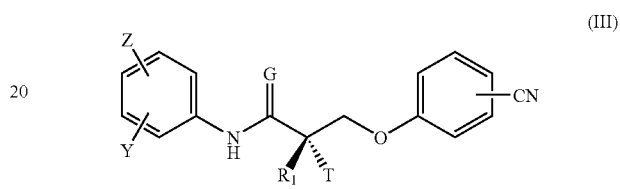

(III)

wherein:
G is O or S;
T is OH, OR, —NHCOCH$_3$, or NHCOR;
Z is NO$_2$, CN, or $^{13}$C$^{15}$N, COOH, COR, NHCOR or CONHR;
Y is CF$_3$, alkyl, F, I, Br, Cl, CN, C(R)$_3$ or Sn(R)$_3$;
R is hydrogen, alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$; and
Z is $^{13}$C$^{15}$N or the cyano-substituted phenol ring incorporates at least one deuterium atom or $^{14}$C atom;
said process comprising the steps of:
➢ reacting

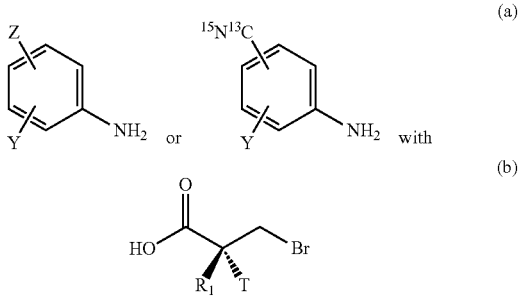

(a)

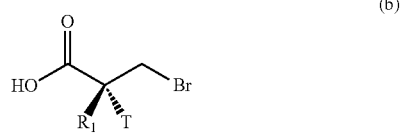

(b)

to obtain

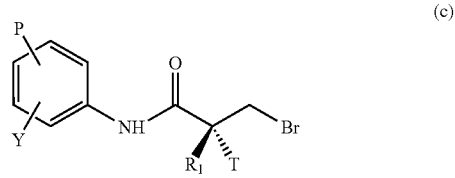

(c)

where P is Z or $^{15}N^{13}C$; and

➢ reacting (c) with

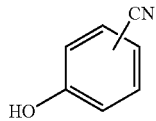

having at least one deuterium atom or $^{13}C$ atom or

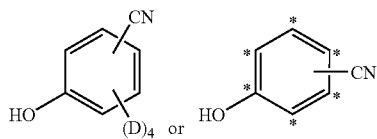

(wherein the asterisk represents $^{14}C$ incorporation)
to obtain a labeled of compound of formula III.

Metabolites of the SARM compound of formula I and compositions comprising the same are useful, in some embodiments, for a) binding a selective androgen receptor modulator metabolite to an androgen receptor; b) male contraception; c) suppressing spermatogenesis; d) hormone therapy; e) hormone related therapy; f) treatment of a variety of hormone-related conditions, for example conditions associated with Androgen Decline in Aging Male (ADAM), such as fatigue, depression, decreased libido, sexual dysfunction, erectile dysfunction, hypogonadism, hair loss, anemia, obesity, sarcopenia, osteopenia, osteoporosis, benign prostate hyperplasia, alterations in mood and cognition and prostate cancer; g) preventing, delating the progression, preventing the recurrence and/or treating the recurrence of prostate cancer; h) inducing the apoptosis in a cancer cell; i) treating a subject having muscle wasting disorder; j) treating cachexia in a human subject; k) treating bone-related disorder in a human subject; l) increasing bone mass in a human subject; m) treating, reducing the severity of, reducing the incidence of, delaying the onset of, or reducing pathogenesis of diabetes in a human subject; n) improving lipid profile; o) treating, reducing the severity of, reducing the incidence of, delaying the onset of, or reducing pathogenesis of fatty liver conditions in a human subject; p) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; q) preventing and/or treating dry eye conditions; and/or r) oral androgen replacement therapy.

The metabolites of the present invention offer a significant advancement over steroidal androgen treatment. The selective androgen receptor modulator compound metabolites thereof, as described herein, in some embodiments, exhibit androgenic and anabolic activity. The selective androgen receptor modulator compound metabolites thereof, as described herein, in some embodiments, exhibit antiandrogenic activity. The selective androgen receptor modulator compound metabolites thereof, as described herein, in some embodiments, exhibit partial agonist and/or partial antagonist activity. The selective androgen receptor modulator compound metabolites thereof, as described herein, in some embodiments, exhibit antiandrogenic activity. The selective androgen receptor modulator compound metabolites thereof, as described herein, are non-steroidal ligands for the androgen receptor, and in some embodiments, use thereof is not accompanied by serious side effects, inconvenient modes of administration, or high costs yet possesses the advantages of oral bioavailability, lack of cross-reactivity with other steroid receptors, and long biological half-lives.

BRIEF DESCRIPTION OF THE FIGURES

The present invention will be understood and appreciated more fully from the following detailed description taken in conjunction with the appended figures which depict:

FIG. 1: schematically depicts the synthesis of compound I.

FIG. 45 schematically depicts the synthesis of isotope labeled compounds I and II.

DETAILED DESCRIPTION OF THE INVENTION

Figure 1A:
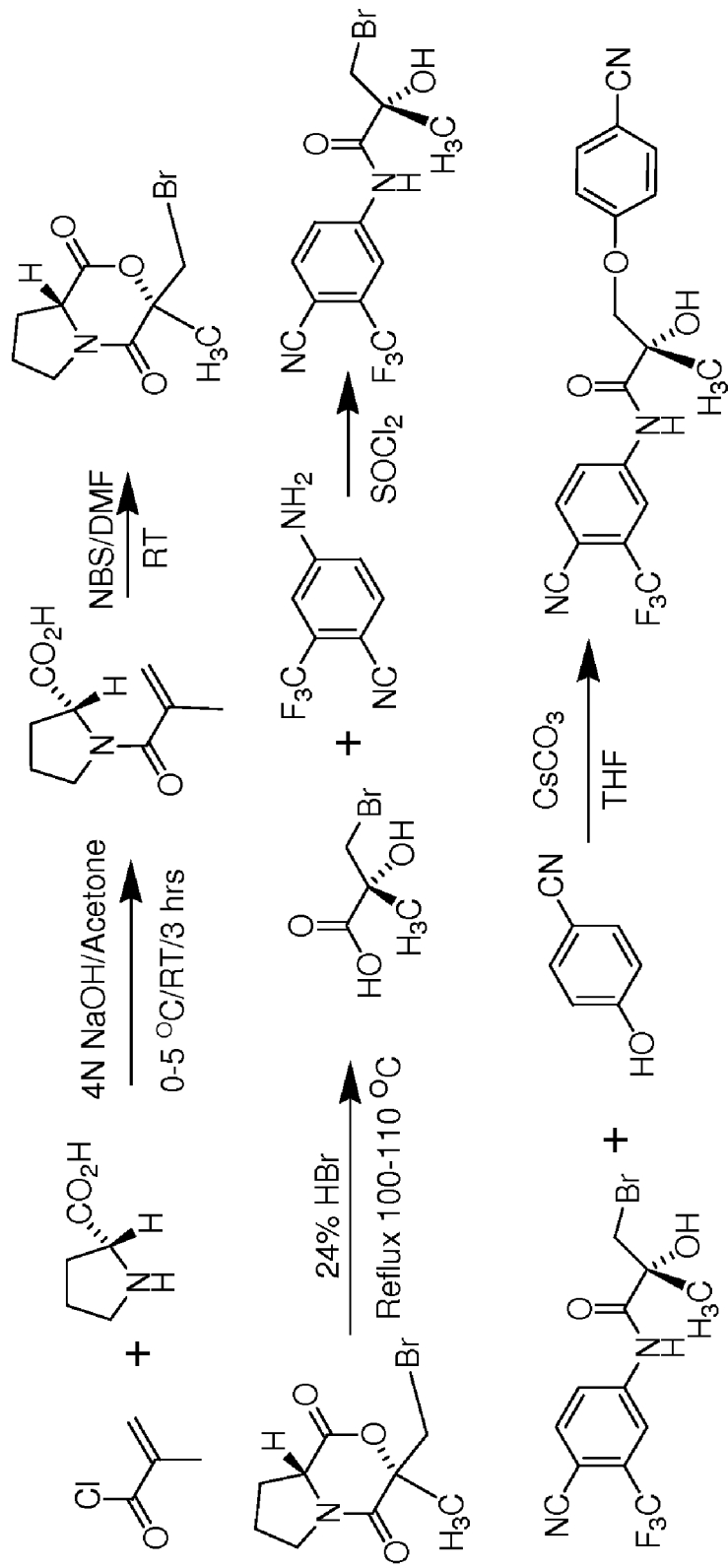
FIG. 1A depict the (S)-enantiomer of compound I.
Figure 1B:
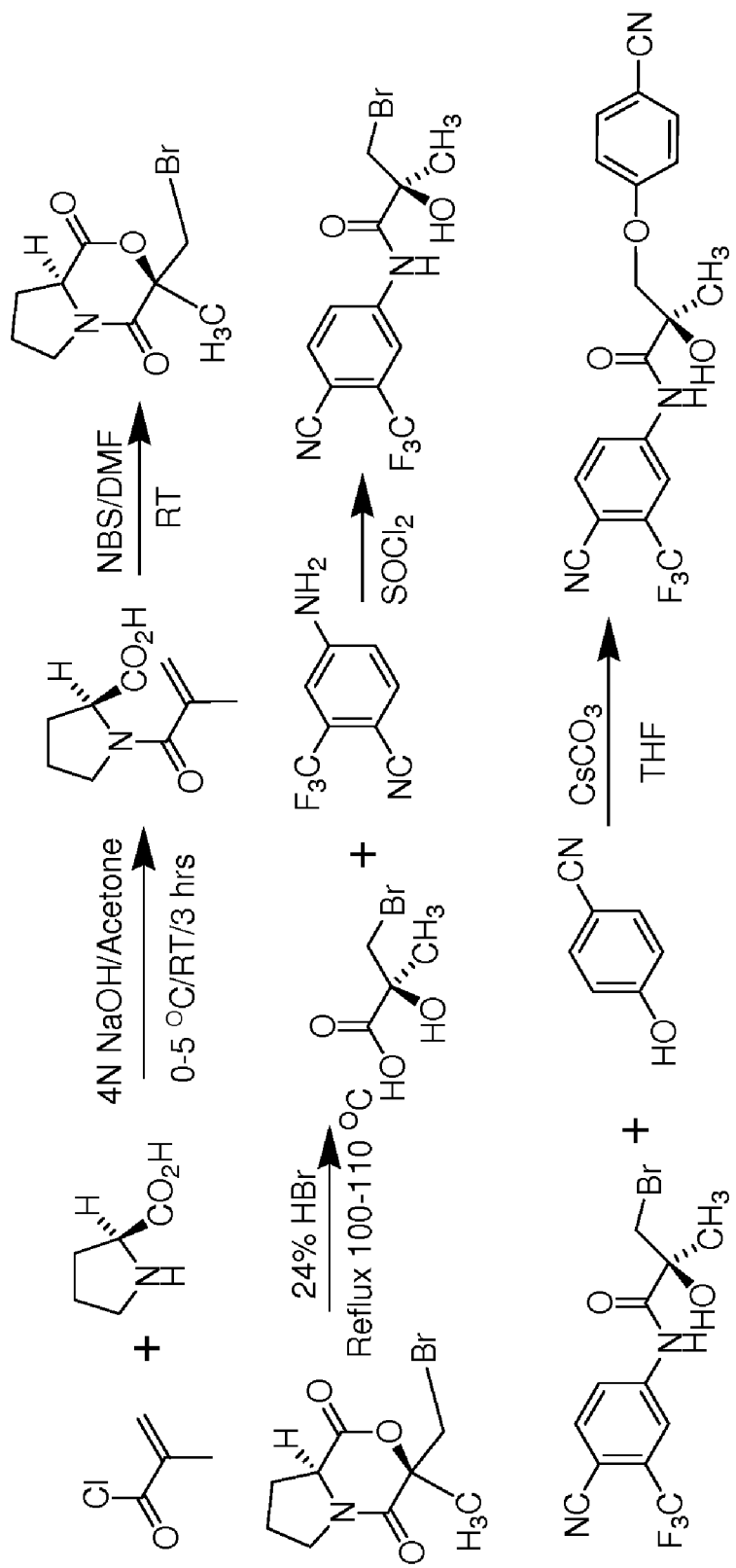
FIG. 1B depicts the (R) enantiomer of compound I.
Figure 2:
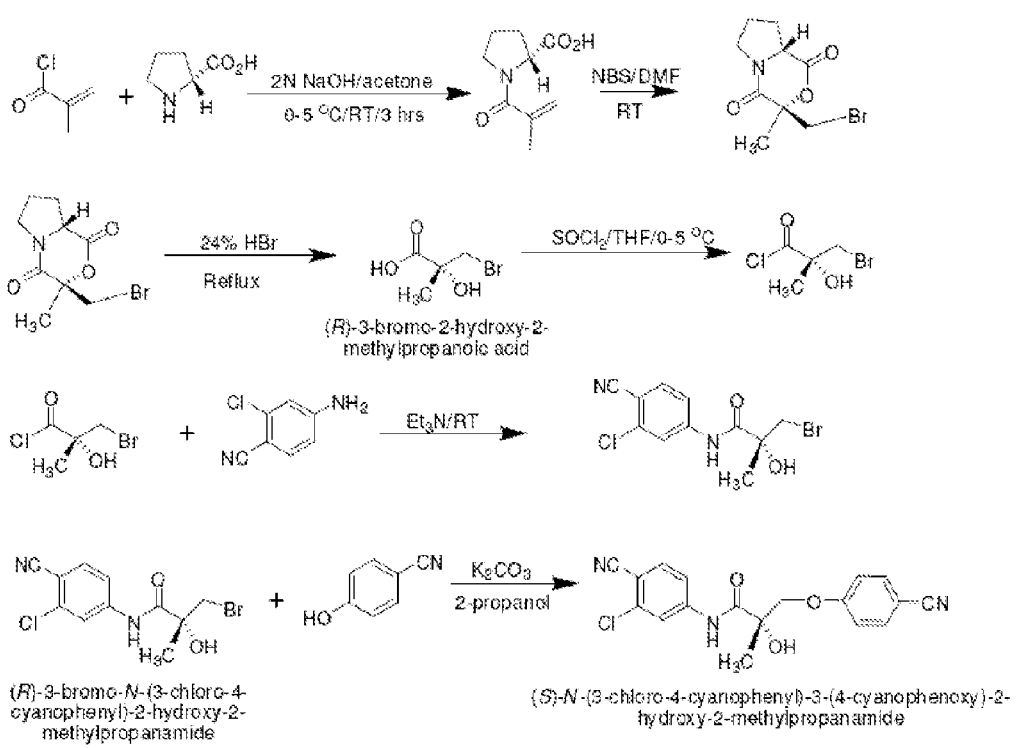
FIG. 2: schematically depicts the synthesis of the (S)-enantiomer of compound II.

In one embodiment, this invention provides a metabolite of a selective androgen receptor modulator (SARM) compound, wherein said SARM is represented by the structure of formula I:

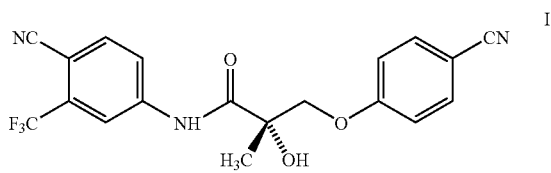

In one embodiment, the metabolite is a glucuronide metabolite of the compound of formula I. "Glucuronic acid" is the substituent that is transferred to a metabolite or transferred to a parent compound to form a metabolite from the phase II conjugation reaction of glucuronidation. Glucuronic acid reacts with an acid or alcohol or phenol moiety on the metabolite or parent compound to form the "glucuronide". The glucuronide substituent is abbreviated in the formulae herein as "Glu" or "Glucuronide".

In another embodiment, the metabolite of the selective androgen receptor modulator of structure I, is represented by the structure:

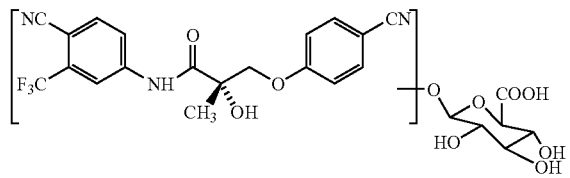

In another embodiment, the metabolite of the selective androgen receptor modulator of structure I, is represented by the structure:

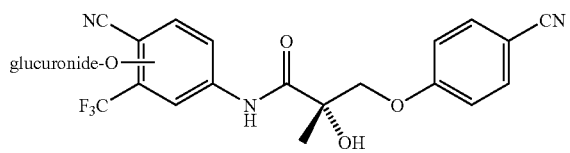

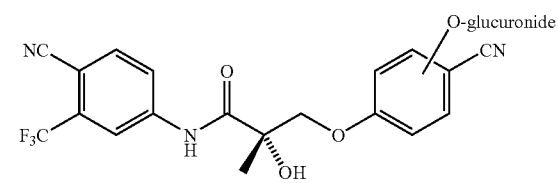

In another embodiment, the metabolite of the selective androgen receptor modulator of structure I, is represented by the structure:

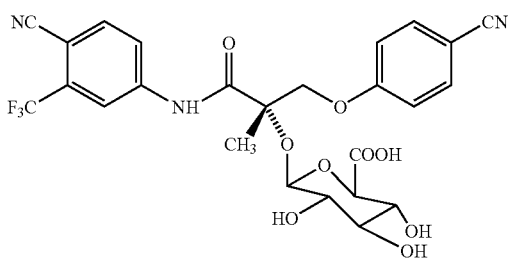

In another embodiment, the metabolite of the selective androgen receptor modulator of structure I, is represented by the structure:

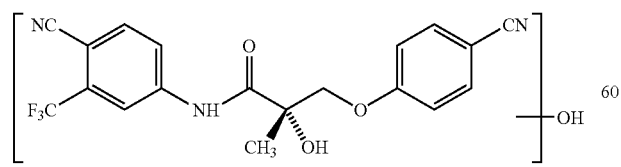

In another embodiment, the metabolite of the selective androgen receptor modulator of structure I is represented by structure:

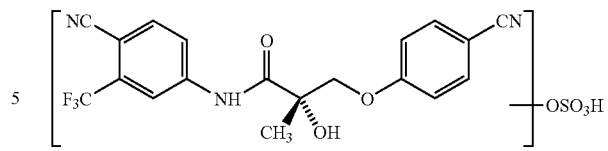

In another embodiment, the metabolite of the selective androgen receptor modulator of structure I, is represented by the structure:

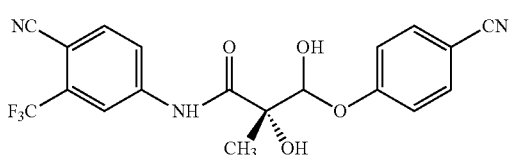

In another embodiment, the metabolite of the selective androgen receptor modulator of structure I, is represented by the structure:

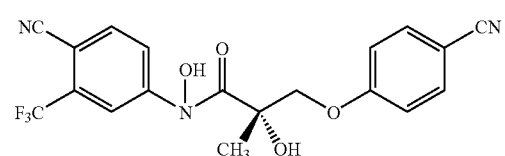

In another embodiment, the metabolite of the selective androgen receptor modulator of structure I, is represented by the structure:

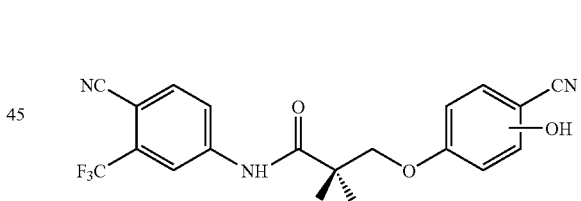

In another embodiment, the metabolite of the selective androgen receptor modulator of structure I, is represented by the structure:

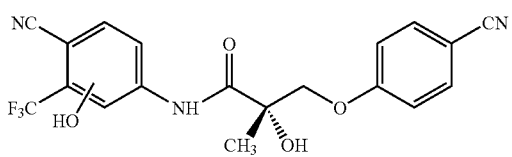

In another embodiment, the metabolite of the selective androgen receptor modulator of structure I, is represented by the structure:

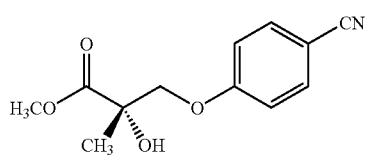

In another embodiment, the metabolite of the selective androgen receptor modulator of structure I, is represented by the structure:

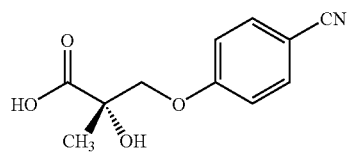

In another embodiment, this invention provides a metabolite of a selective androgen receptor modulator (SARM) compound, wherein said SARM is represented by the structure of formula II:

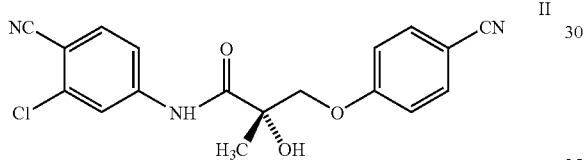

II

In one embodiment, the metabolite is a glucuronide metabolite of the compound of formula II. In another embodiment, the metabolite of the selective androgen receptor modulator of structure II, is represented by the structure:

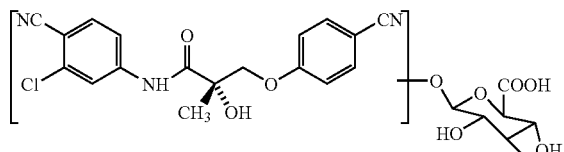

In another embodiment, the metabolite of the selective androgen receptor modulator of structure II, is represented by the structure:

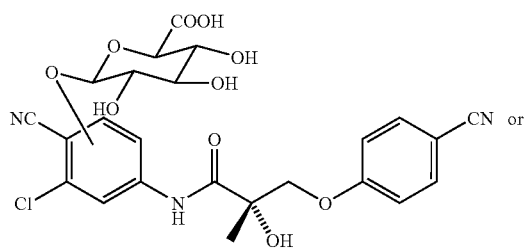

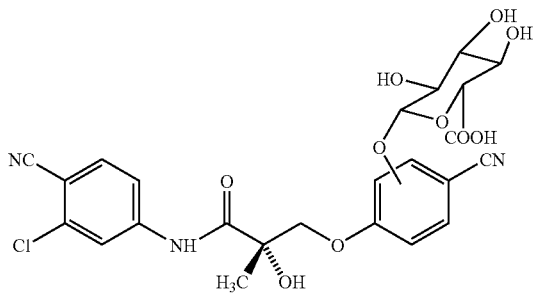

In another embodiment, the metabolite of the selective androgen receptor modulator of structure II, is represented by the structure:

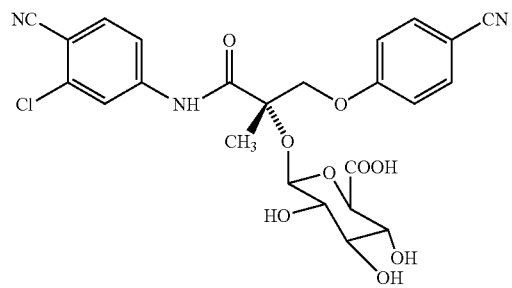

In another embodiment, the metabolite of the selective androgen receptor modulator of structure II, is represented by the structure:

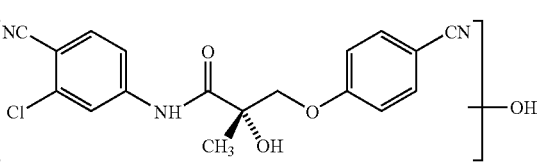

In another embodiment, the metabolite of the selective androgen receptor modulator of structure II, is represented by the structure:

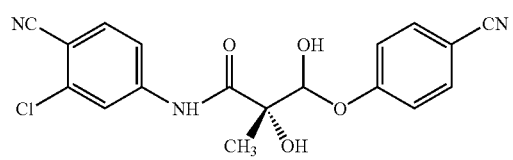

In another embodiment, the metabolite of the selective androgen receptor modulator of structure II, is represented by the structure:

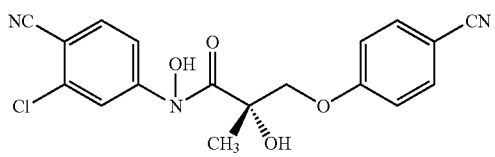

In another embodiment, the metabolite of the selective androgen receptor modulator of structure II, is represented by the structure:

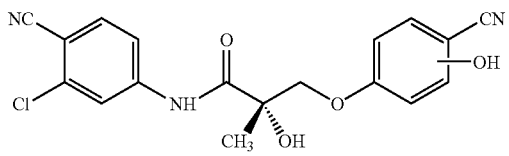

In another embodiment, the metabolite of the selective androgen receptor modulator of structure II, is represented by the structure:

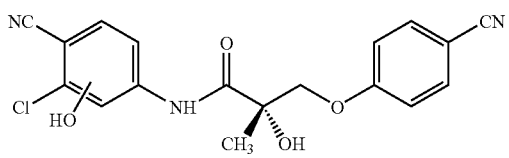

In another embodiment, the metabolite of the selective androgen receptor modulator of structure II, is represented by the structure:

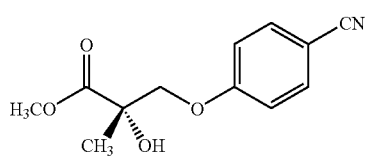

In another embodiment, the metabolite of the selective androgen receptor modulator of structure II, is represented by the structure:

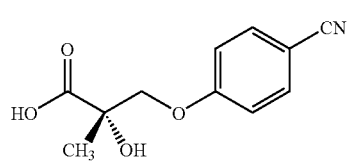

In another embodiment, the metabolite of the selective androgen receptor modulator of structure II, is represented by the structure:

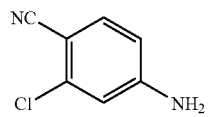

In another embodiment, the metabolite of the selective androgen receptor modulator of structure II, is represented by the structure:

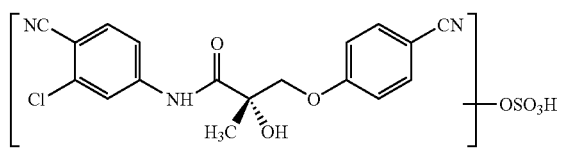

In one embodiment, the present invention provides a metabolite of a selective androgen receptor modulator (SARM) compound, wherein the SARM compound is represented by the structure of formula III:

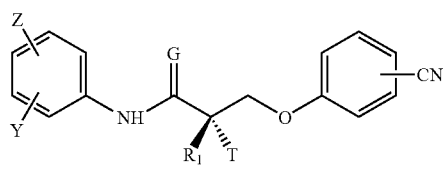

III wherein
G is O or S;
T is OH, OR, —NHCOCH$_3$, or NHCOR;
Z is NO$_2$, CN, COOH, COR, NHCOR or CONHR;
Y is CF$_3$, alkyl, F, I, Br, Cl, CN, C(R)$_3$ or Sn(R)$_3$;
R is hydrogen, alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH; and
R$_1$ is CH$_3$, CH$_2$F, CHF$_2$, CF$_3$, CH$_2$CH$_3$, or CF$_2$CF$_3$.

In another embodiment, T in compound III is OH. In another embodiment, R$_1$ in compound III is CH$_3$. In another embodiment, Z in compound III is NO$_2$. In another embodiment, Z in compound III is CN. In another embodiment, Y in compound III is CF$_3$. In another embodiment, the CN on the phenol ring in compound III is in the para position. In another embodiment, Z in compound III is in the para position. In another embodiment, Z in compound III is CN and is in the para position. In another embodiment, Y in compound III is in the meta position. In another embodiment Y in compound III is in the meta position. In another embodiment, Z is CN, and Y is Cl.

The substituents Z and Y can be in any position of the ring carrying these substituents (hereinafter "A ring"). In another embodiment, the substituent Z is in the para position of the A ring and substituent Y is in the meta position of the A ring.

The substituent CN can be in any position of the ring carrying this substituent (hereinafter "B ring"). In another embodiment, the substituent CN and is in the para position of the B ring.

In another embodiment, the metabolite of the selective androgen receptor modulator of structure III, is represented by the structure:

IIIa

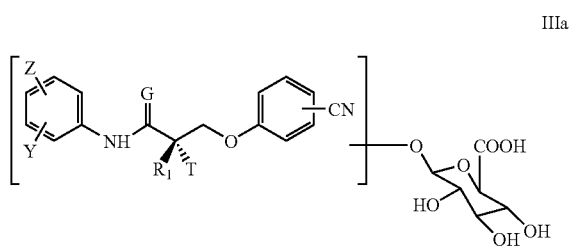

In another embodiment, the metabolite of the selective androgen receptor modulator of structure III, is represented by the structure:

IIIb

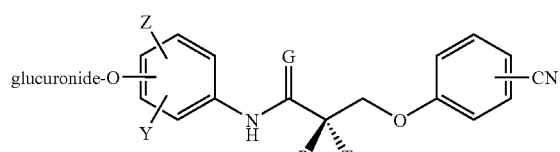

IIIc

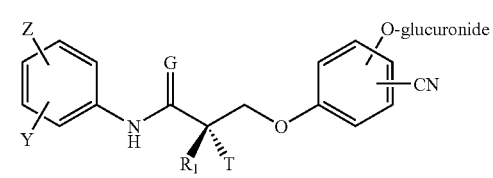

In another embodiment, the metabolite of the selective androgen receptor modulator of structure III, is represented by the structure:

IIId

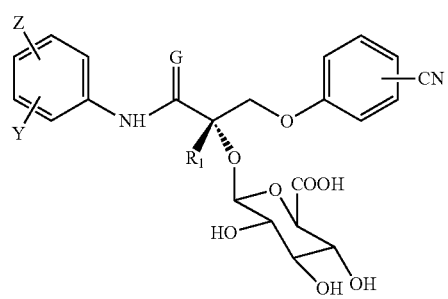

In another embodiment, the metabolite of the selective androgen receptor modulator of structure III, is represented by the structure:

IIIe

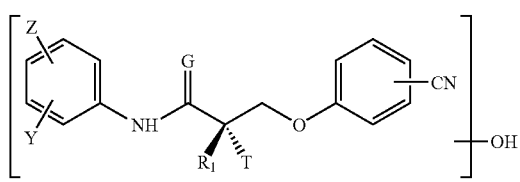

In another embodiment, the metabolite of the selective androgen receptor modulator of structure III, is represented by the structure:

IIIf

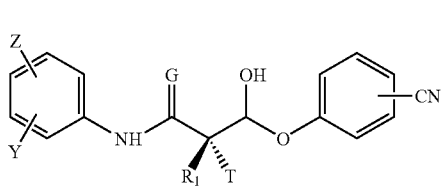

In another embodiment, the metabolite of the selective androgen receptor modulator of structure III, is represented by the structure:

IIIg

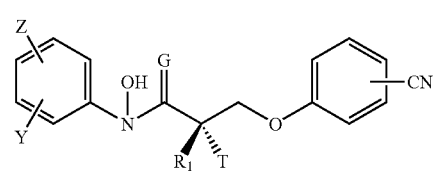

In another embodiment, the metabolite of the selective androgen receptor modulator of structure III, is represented by the structure:

IIIh

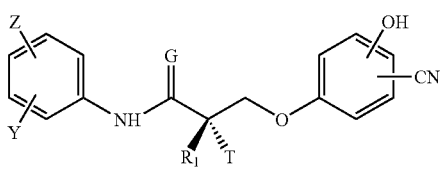

In another embodiment, the metabolite of the selective androgen receptor modulator of structure III, is represented by the structure:

IIIi

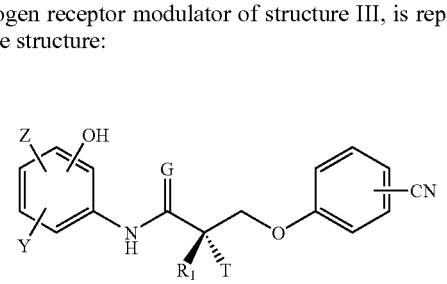

In another embodiment, the metabolite of the selective androgen receptor modulator of structure III, is represented by the structure:

IIIj

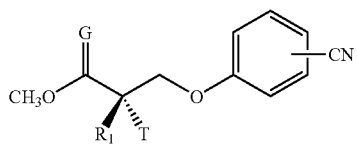

IIIk

In another embodiment, the metabolite of the metabolite of the androgen receptor modulator of structure III, is represented by the structure:

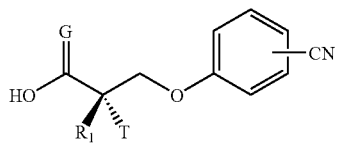

IIIl

In one embodiment, the present invention provides a metabolite of a selective androgen receptor modulator (SARM) compound, wherein the SARM compound is represented by the structure of formula IV:

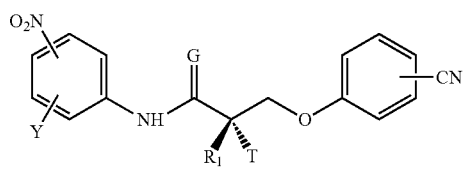

IV wherein
G is O or S;
T is OH, OR, —NHCOCH$_3$, or NHCOR;
Y is CF$_3$, alkyl, F, I, Br, Cl, CN, C(R)$_3$ or Sn(R)$_3$;
R is hydrogen, alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH; and
R$_1$ is CH$_3$, CH$_2$F, CHF$_2$, CF$_3$, CH$_2$CH$_3$, or CF$_2$CF$_3$.

In one embodiment, the metabolite of the SARM compound of formula IV is represented by the structure:

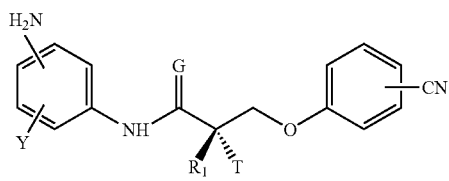

In another embodiment, the metabolite of the SARM compound of formula IV is represented by the structure:

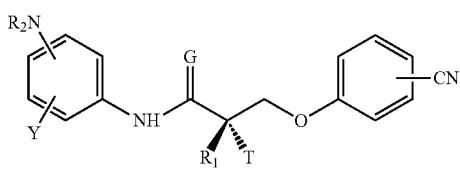

wherein NR$_2$ is NO, NHOH, NHOSO$_3$, or NHO-glucuronide.

In another embodiment, the metabolite of the selective androgen receptor modulator of structure IV, is represented by the structure:

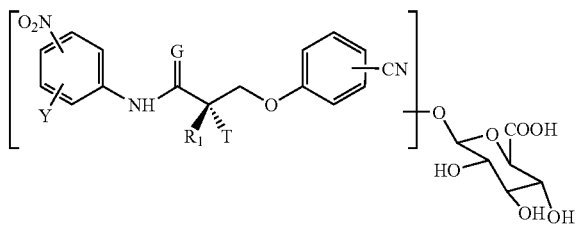

In another embodiment, the metabolite of the selective androgen receptor modulator of structure IV, is represented by the structure:

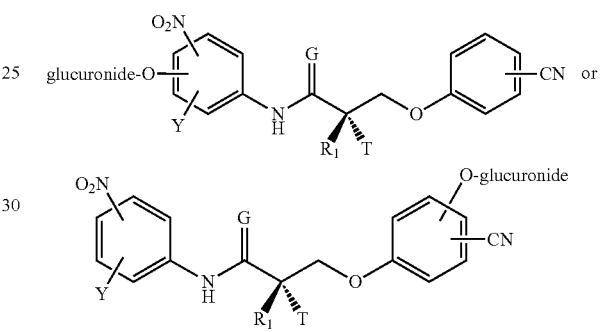

In another embodiment, the metabolite of the selective androgen receptor modulator of structure IV, is represented by the structure:

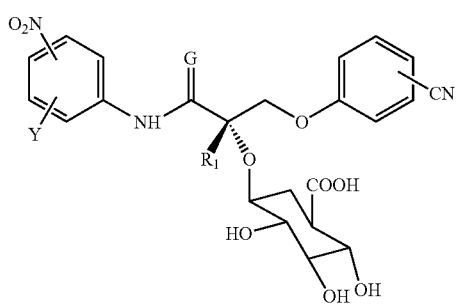

In another embodiment, the metabolite of the selective androgen receptor modulator of structure IV, is represented by the structure:

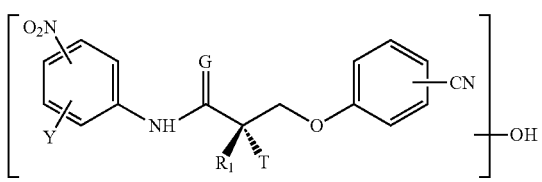

In another embodiment, the metabolite of the selective androgen receptor modulator of structure IV, is represented by the structure:

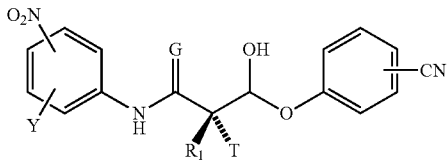

In another embodiment, the metabolite of the selective androgen receptor modulator of structure IV, is represented by the structure:

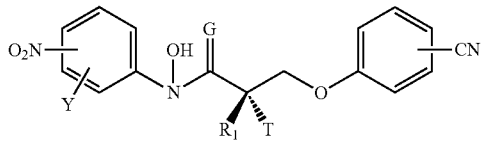

In another embodiment, the metabolite of the selective androgen receptor modulator of structure IV, is represented by the structure:

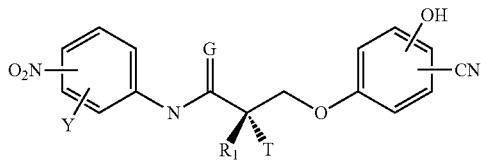

In another embodiment, the metabolite of the selective androgen receptor modulator of structure IV, is represented by the structure:

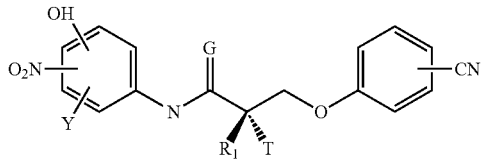

In another embodiment, the metabolite of the selective androgen receptor modulator of structure IV, is represented by the structure:

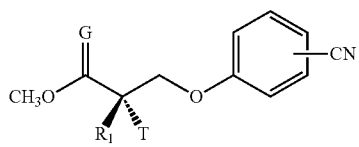

In another embodiment, the metabolite of the selective androgen receptor modulator of structure IV, is represented by the structure:

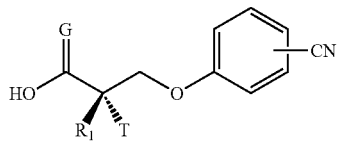

In another embodiment, this invention provides a metabolite of the compounds of formula I, II, III or IV wherein the metabolite is a glucuronide modification. In another embodiment, this invention provides a metabolite of compounds of formula I, II, III or IV wherein the metabolite is a glucuronide modification of the hydroxyl on the chiral carbon. In another embodiment, this invention provides a metabolite of compounds of formula I, II, III or IV wherein the metabolite is a glucuronide modification of the cyanophenol ring.

In another embodiment, this invention provides a metabolite of compounds of formula I, II, III or IV wherein the metabolite is a hydroxyl modification. In another embodiment, this invention provides a metabolite of compounds of formula I, II, III or IV wherein the metabolite is a mono-hydroxy modification. In another embodiment, this invention provides a metabolite of compounds of formula I, II, III or IV wherein the metabolite is a mono-hydroxy modification, which is represented by three distinct mono-hydroxy species. In another embodiment, this invention provides a metabolite of compounds of formula I, II, III or IV wherein the metabolite includes di-hydroxy modifications. In another embodiment, this invention provides a metabolite of compounds of formula I, II, III or IV wherein the metabolite includes tri-hydroxy modifications. In another embodiment, this invention provides a metabolite of the compounds of formula I, II, III or IV wherein the metabolite includes di-hydroxy modifications in which the di-hydroxy group resides on the phenol ring. In another embodiment, this invention provides a metabolite of compounds of formula I, II, III or IV wherein the metabolite is a mono-hydroxy modification of a cyanophenol ring. In another embodiment, this invention provides a metabolite of the compounds of formula I, II, III or IV wherein the metabolite includes tri-hydroxy modifications.

In another embodiment, this invention provides a metabolite of compounds of formula I, II, III or IV wherein the metabolite includes a mono-hydroxyl, di-hydroxy or tri-hydroxy modification of said compounds, wherein said modification is present on the anilide ring, or in some embodiments, said modification is present on the phenol ring of the compounds of formula I, II, III or IV.

In another embodiment, this invention provides a metabolite of compounds of formula I, II, III or IV wherein the metabolite is a sulfate modification. In another embodiment, this invention provides a metabolite of the compounds of formula I, II, III or IV wherein the metabolite is a hydroxyl-sulfate modification. In another embodiment, this invention provides a metabolite of the compounds of formula I, II, III or IV wherein the metabolite is a hydroxyl-sulfate modification is a product of the cyano-anilide. In another embodiment, this invention provides a metabolite of the compounds of formula I, II, III or IV wherein the metabolite is a sulfate modification of a mono-hydroxy metabolite. In another embodiment, this invention provides a metabolite of formula I, II, III or IV wherein the metabolite is a sulfate modification, di-hydroxy-sulfate modification, mono-hydroxy modification, O-glucuronide-modification, glycine-modification, or combinations thereof. It is to be understood that the metabolite compounds of this invention may comprise multiple modifications of the parent compound, as herein described, including any combination of such modifications as herein described, as will be appreciated by the skilled artisan. For example, and in some embodiments, the metabolites of this invention may comprise any hydroxyl-modification, any O-sulfate modification, any O-glucuronide modification, any glycine modification, any ester modification, or any thio-ester modification, or any combination thereof, including multiple modifications of a comparable type in combination with another. For example, and in some embodiments, the metabolites of this invention may comprise a di-hydroxy modification on the anilide ring and a monohydroxy and O-sulfate modification on the phenol ring. Such exemplary modifications are to be construed as teaching any of the possible modifications, and should not be construed to be limiting in this regard.

In another embodiment, this invention provides a metabolite of the compounds of formula I, II, III or IV wherein the modification is an ester or thio-ester. In another embodiment, this invention provides a metabolite of the compounds of formula I, II, III or IV wherein the metabolite is an ester formed by hydrolysis of the acylanilide ring.

In some embodiments, metabolism of the compounds of formula I, II, III or IV may result in a metabolite product, which comprises cyanophenol, O-glucuronide-cyano-phenyl, O-sulfate-cyano-phenyl or an ester of cyano-phenyl.

In another embodiment, this invention provides a metabolite of the compounds of formula I, II, III or IV wherein the modification is on the acylanilide ring. In another embodiment, this invention provides a metabolite of the compounds of formula I, II, III or IV wherein the metabolite is on the phenol ring. In another embodiment, this invention provides a metabolite of the compounds of formula I, II, III or IV wherein the metabolite is on the acylanilide ring or on the phenyl ring, or both.

In another embodiment, this invention provides for further metabolism of the metabolites of the compounds of formula I, II, III or IV and products formed thereby, wherein said metabolism comprises further modification on the acylanilide ring, and said one or more modifications comprises hydrolysis, glucuronidation, sulfation, esterification, and other processes as described herein, and as appreciated by the skilled artisan. Such modifications may result in any or multiple metabolites as herein described, for example, production of hydroxyl-cyanophenol; O-glucuronidation of cyanophenol; and O-sulfation of cyanophenol, and others.

In another embodiment, this invention provides for further metabolism of the metabolites of the compounds of formula I, II, III or IV as herein described, and compounds formed thereby, wherein said metabolism results in incorporation of a modification on the phenol ring or the anilide ring of compounds of formula I, II, III or IV.

As contemplated herein, the present invention provides metabolites of the selective androgen receptor modulator of formula I, II, III or IV. However, also contemplated within the scope of the present invention are analogs, isomers, derivatives, pharmaceutically acceptable salts, pharmaceutical products, hydrates, N-oxides, impurities, polymorphs or crystals of the metabolites of the compounds of formula I, II, III or IV, or any combination thereof.

In another embodiment, the SARM compound metabolite, is a metabolite of the metabolite of a SARM compound of structures I, II, II and IV, its sub-structures, or combinations thereof. In another embodiment, the SARM compound metabolite, is a metabolite of a SARM compound of structures I, II, II and IV, its sub-structures, or analogs, isomers, derivatives, pharmaceutically acceptable salts, pharmaceutical products, hydrates, N-oxides, impurities, polymorphs or crystals of the metabolites of the compounds of formula I, II, III or IV, or any combination thereof.

In another embodiment, the metabolite is a methylated modification of the SARM compound of formula I, II, III or IV.

In another embodiment, the use of a SARM compound metabolite/s as herein described for treating a subject having a muscle wasting disorder, or any of the disorders described herein, includes administering a pharmaceutical composition including a SARM compound metabolite/s as herein described In one embodiment, the metabolite is an androgen receptor agonist. In another embodiment, the metabolite is an androgen receptor antagonist.

In one embodiment, this invention provides radiolabeled compounds of formulae I, II, III and/or IV, and methods of detecting the same. In one embodiment, the term "radiolabeled" refers to a molecule, which is incorporated into the indicated compound, which is a radioactive isotope, or in some embodiments, the term radiolabel includes stable isotopes. In some embodiments, the term radiolabeled specifically includes the incorporation of $^{13}C$, $^{14}C$, $^{15}N$, $^{18}O$, deuterium, $^{3}H$ or any combination thereof within the referenced compounds of this invention.

In some embodiments, the radiolabeled compound is a compound of formula III:

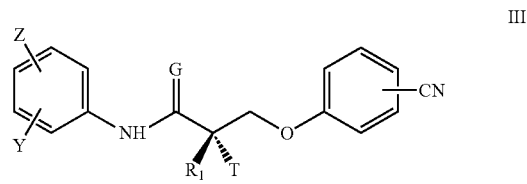

III wherein
G is O or S;
T is OH, OR, —NHCOCH$_3$, or NHCOR;
Z is NO$_2$, CN, COOH, COR, NHCOR or CONHR;
Y is CF$_3$, alkyl, F, I, Br, Cl, CN, C(R)$_3$ or Sn(R)$_3$;
R is hydrogen, alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH; and
R$_1$ is CH$_3$, CH$_2$F, CHF$_2$, CF$_3$, CH$_2$CH$_3$, or CF$_2$CF$_3$;
and a radiolabel comprising $^{13}C$, $^{14}C$, $^{15}N$, $^{18}O$, deuterium, $^{3}H$ or any combination thereof is incorporated in any appropriate atom or atoms.

In some embodiments, this invention provides methods of detecting the metabolites of the compounds as herein described, including in some embodiments, methods of detecting radiolabeled metabolite compounds as herein described, wherein said method comprises detecting the radiolabeled metabolite by spectroscopy means.

In one embodiment, this invention provides a method of detecting a metabolite of a compound of formula III,

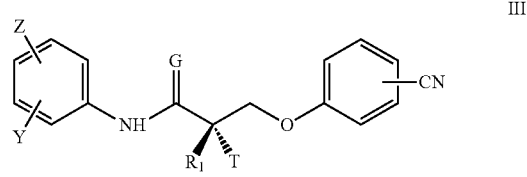

III wherein
G is O or S;
T is OH, OR, —NHCOCH₃, or NHCOR;
Z is NO₂, CN, COOH, COR, NHCOR or CONHR;
Y is CF₃, alkyl, F, I, Br, Cl, CN, C(R)₃ or Sn(R)₃;
R is hydrogen, alkyl, haloalkyl, dihaloalkyl, trihaloalkyl, CH₂F, CHF₂, CF₃, CF₂CF₃, aryl, phenyl, F, Cl, Br, I, alkenyl or OH; and
R₁ is CH₃, CH₂F, CHF₂, CF₃, CH₂CH₃, or CF₂CF₃;
said method comprising the step of:
incorporating ¹³C, ¹⁴C, ¹⁵N, ¹⁸O, ²H, ³H or any combination thereof in said compound and detecting a metabolite of said compound by spectroscopy, whereby a metabolite of said compound exhibits different spectroscopic characteristics than a compound of formula III.

In one embodiment, incorporating results in a compound represented by the following structure:

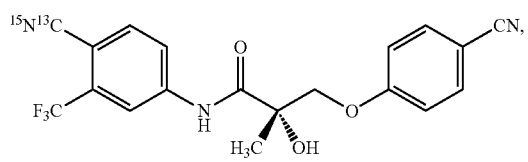

or in some embodiments, incorporating results in a compound represented by the following structure:

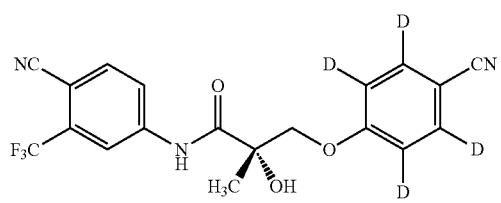

wherein D represents ²H; or in some embodiments, incorporating results in a compound represented by the following structure:

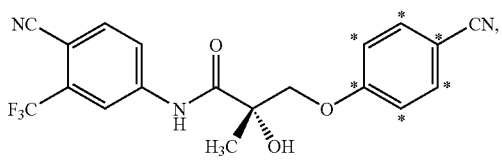

wherein the asterisk represents ¹⁴C incorporation; or in some embodiments, incorporating results in a compound represented by the following structure:

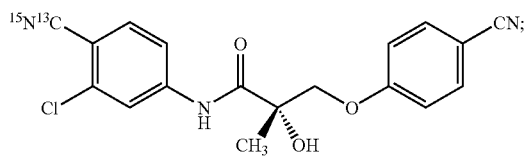

or in some embodiments, incorporating results in a compound represented by the following structure:

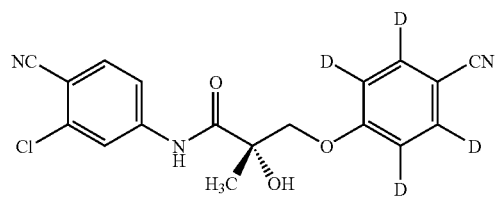

wherein D represents ²H; or in some embodiments, incorporating results in a compound represented by the following structure:

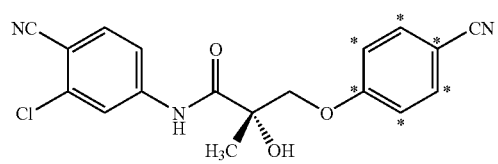

wherein the asterisk represents ¹⁴C incorporation.

Yet another embodiment of the invention is a method of detection of one or more metabolites of a SARM compound of the formula I, II, III and IV. Another embodiment is the detection of one or more metabolites of a SARM compound of the formula I, II, III and IV, wherein the metabolite is detected from a patient sample.

In another embodiment the patient sample is selected from hair, tissue, urine, blood, plasma, sweat, saliva or combinations thereof. Another embodiment is a method of detection and assay for the detection of metabolites for a variety of purposes, for example, for detecting the use of performance enhancing drugs.

In another embodiment the method of detection is an assay. In another embodiment, the metabolite is determined by spectroscopic means such as LC-MS/MS and MS/MS/MS. In another embodiment, the method of detection involves analyzing radiolabeled metabolite of a compound described herein. Other methods of detection are well known to those skilled in the art. For example, and in some embodiments, methods such as those described in Thevis, Mario, et al. Screening for Metabolically Stable aryl-propionamide-derived Selective Androgen Receptor Modulators for Doping Purposes. *Rapid Commun. Mass Spectrom.* 2006; 20:870-876; in Thevis, Mario, et al. Screening for 2-Quinolinone-derived Selective Androgen Receptor Agonists in Doping Control Analysis. *Rapid Commun. Mass Spectrom.* 2007; 21:3477-3486; in Thevis, Mario, et al. New Drugs and Methods of Doping and Manipulation. *Drug Discovery Today.* 2008; 13(1/2): 60-65; and in Tiia, Kuuranne, et al. Aryl-Propionamide-Derived Selective Androgen Receptor Modulators: Liquid Chromatography-Tandem Mass Spectrometry Characterization of the in Vitro Synthesized Metabolites for Doping Control Purposes. *Drug Metabolism and Disposition.* 2008; 36: 571-581, may be used, which are all incorporated herein in their entirety by reference.

Synthesis of radiolabeled compounds may be accomplished, for example, as described in U.S. Pat. No. 6,019,957 granted Feb. 1, 2000, which in incorporated by reference herein in its entirety. In another embodiment, this invention provides a process for the preparation of radiolabled compounds I-IV. In another embodiment, the radiolabled compounds are prepared according to Examples 8-10. In another embodiment, the radiolabled compounds are prepared according to FIG. 45.

In some embodiments, this invention provides a process for the preparation of a labeled compound of formula III:

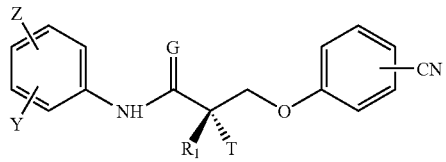

wherein:
G is O or S;
T is OH, OR, —NHCOCH$_3$, or NHCOR;
Z is NO$_2$, CN, or $^{13}C^{15}N$, COOH, COR, NHCOR or CONHR;
Y is CF$_3$, alkyl, F, I, Br, Cl, CN, C(R)$_3$ or Sn(R)$_3$;
R is hydrogen, alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$; and
Z is $^{13}C^{15}N$ or the cyano-substituted phenol ring incorporates at least one deuterium atom or $^{14}C$ atom; said process comprising the steps of:

➢ reacting

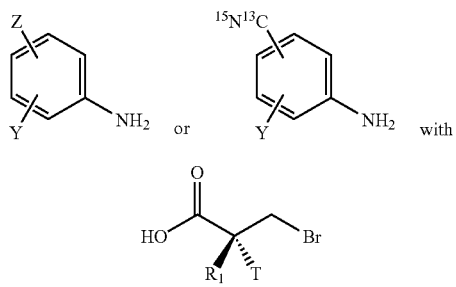

to obtain

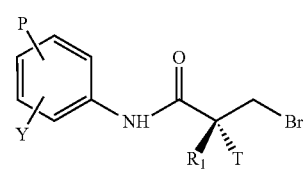

where P is Z or $^{15}N^{13}C$; and
➢ reacting (c) with

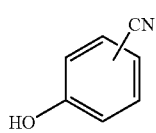

having at least one deuterium atom or $^{13}C$ atom or

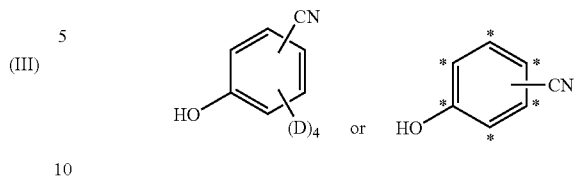

wherein the asterisk represents $^{14}C$ incorporation) to obtain a labeled of compound of formula III.

In one embodiment, this invention provides a radiolabled compound of formula I, II, III or IV. In one embodiment, this invention provides an isotope labels of compound of formula I, II, III or IV. In another embodiment, the isotopes are incorporated into the anilide ring, the phenol ring, carbonyl or combination thereof of compounds of formula I-IV. In another embodiment, the isotopes are $^{15}N$, $^{13}C$, $^{14}C$, $^{18}O$, deuterium, $^3H$, or a combination thereof, where applicable.

In one embodiment, this invention provides a radiolabeled compound of formula I represented by the following structure:

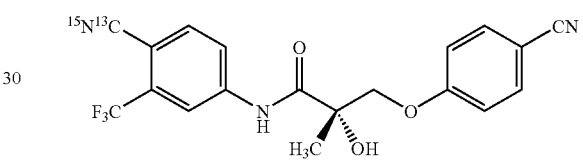

In one embodiment, this invention provides a radiolabeled compound of formula I represented by the following structure:

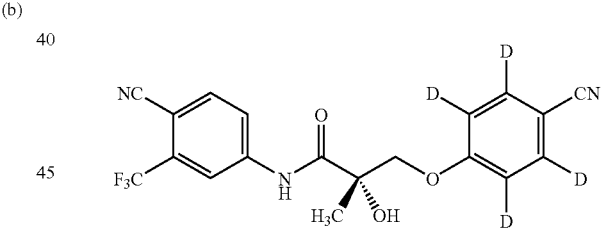

wherein D represents deuterium.

In one embodiment, this invention provides a radiolabeled compound of formula I represented by the following structure:

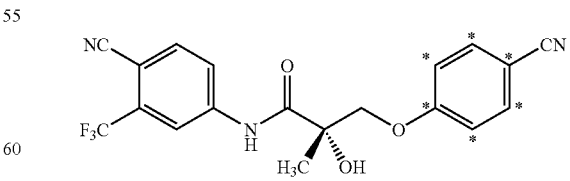

wherein the asterisk represents $^{14}C$ incorporation.

In one embodiment, this invention provides a radiolabeled compound of formula II represented by the following structure:

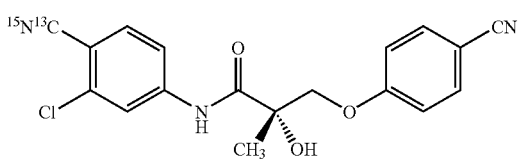

In one embodiment, this invention provides a radiolabeled compound of formula II represented by the following structure:

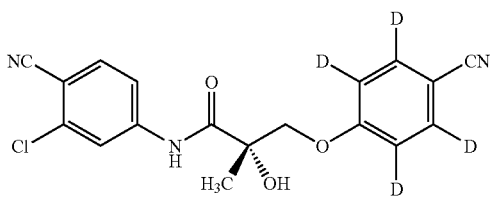

wherein D represents deuterium.

In one embodiment, this invention provides a radiolabeled compound of formula II represented by the following structure:

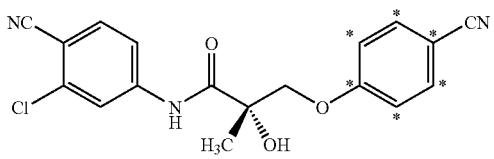

wherein the asterisk represents $^{14}C$ incorporation.

In some embodiments, the substituent R is an alkyl, hydrogen, haloalkyl, dihaloalkyl, trihaloalkyl, $CH_2F$, $CHF_2$, $CF_3$, $CF_2CF_3$; aryl, phenyl, F, Cl, Br, I, alkenyl, or hydroxyl (OH).

An "alkyl" group refers, in some embodiments, to a saturated aliphatic hydrocarbon, including straight-chain, branched-chain and cyclic alkyl groups. In one embodiment, the alkyl group has 1-18 carbons. In another embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen (e.g. F, Cl, Br, I), hydroxy, alkoxy, carbonyl, amido, alkylamido, dialkylamido, nitro, amino, alkylamino, dialkylamino, carboxyl, thio and thioalkyl.

A "haloalkyl" group refers, in some embodiments, to an alkyl group as defined above, which is substituted by one or more halogen atoms, e.g. by F, Cl, Br or I. A "halogen" refers, in some embodiments, to elements of Group VII of the periodic table, e.g. F, Cl, Br or I.

An "aryl" group refers, in some embodiments, to an aromatic group having at least one carbocyclic aromatic group or heterocyclic aromatic group, which may be unsubstituted or substituted by one or more groups selected from halogen (e.g. F, Cl, Br, I), haloalkyl, hydroxy, alkoxy, carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. An "alkenyl" group refers to a group having at least one carbon to carbon double bond.

An "arylalkyl" group refers to an alkyl bound to an aryl, wherein alkyl and aryl are as defined above. An example of an aralkyl group is a benzyl group.

As contemplated herein, the present invention relates to the use of a metabolite of the selective androgen receptor modulator of the present invention. However, also contemplated within the scope of the present invention are analogs, isomers, metabolites, derivatives, pharmaceutically acceptable salts, pharmaceutical products, hydrates, N-oxides, impurities, polymorphs or crystals of the metabolites of the present invention or any combination thereof.

In some embodiments, the term "isomer" includes, but is not limited to, optical isomers and analogs, structural isomers and analogs, conformational isomers and analogs, and the like.

In one embodiment, this invention encompasses the use of various optical isomers of the metabolites as herein described. It will be appreciated by those skilled in the art that the metabolites of the present invention contain at least one chiral center. Accordingly, the metabolites used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or mixtures thereof, which form possesses properties useful in the methods as described herein. In one embodiment, the metabolites are the pure (R)-isomers. In another embodiment, the metabolites are the pure (S)-isomers. In another embodiment, the metabolites are a mixture of the (R) and the (S) isomers. In another embodiment, the metabolites are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The term "metabolite", in some embodiments refers to a substance, which can be converted in vivo into a biologically active agent by such reactions as hydrolysis, hydroxylation, monohydroxylation, di-hydroxylation methylation, glucuronidation, O-glucuronidation, sulfation, amide-hydrolysis, esterification, de-esterification, activation, salt formation and the like, or any combination thereof.

The invention includes pharmaceutically acceptable salts of amino-substituted compounds with organic and inorganic acids, for example, citric acid and hydrochloric acid. The invention also includes N-oxides of the amino substituents of the metabolites described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

In some embodiments, the salts may be derived from using both organic and inorganic acids. Non-limiting examples of such acids include hydrochloric, nitric, sulfuric, and phosphoric. In addition, the metabolites containing a carboxylic acid functionality may form basic addition salts with certain inorganic counter-ions, for example, sodium, potassium, lithium, calcium, magnesium, and the like as well as those formed from organic bases.

The pharmaceutically acceptable salts may be formed by taking about 1 equivalent of the metabolite and contacting it with about 1 equivalent of the appropriate corresponding desired acid or base. Workup and isolation of the resulting salt may be effected by means that will be well-known to one of ordinary skill in the art in light of the instant disclosure.

In some embodiments, the term "about" when in regard to an amount, will refer to an amount that is equal to the indicated amount, or in some embodiments, exceeds or is less than the indicated amount by 1%, or in some embodiments, 2.5%, or in some embodiments, 5%, or in some embodiments, 7.5%, or in some embodiments, 10%, or in some embodiments, 15%, or in some embodiments, any amount therebetween.

This invention further includes derivatives of the metabolites. The term "derivatives" includes but is not limited to ether derivatives, acid derivatives, amide derivatives, ester derivatives and the like. In addition, this invention further includes hydrates of the metabolites. The term "hydrate" includes but is not limited to hemihydrate, monohydrate, dihydrate, trihydrate and the like.

This invention further includes pharmaceutical products of the metabolites. The term "pharmaceutical product" means a composition suitable for pharmaceutical use (pharmaceutical composition), as defined herein.

This invention further includes crystals of the metabolites. Furthermore, this invention provides polymorphs of the metabolites. The term "crystal" means a substance in a crystalline state. The term "polymorph" refers to a particular crystalline state of a substance, having particular physical properties such as X-ray diffraction, IR spectra, melting point, and the like.

The subject invention also includes isotopically-labeled compounds, which are identical to those shown in Formulae I-IV, or any metabolite as described herein, among other compounds encompassed by the invention, but for the fact that one or more atoms are replaced by an atom having an atomic mass or mass number different from the atomic mass or mass number usually found in nature. Non limiting examples of isotopes that can be incorporated into compounds of the invention include isotopes of hydrogen, carbon, nitrogen, oxygen, phosphorous, sulfur, fluorine and chlorine. Metabolites of the present invention, prodrugs thereof, and pharmaceutically acceptable salts of said compounds or of said prodrugs which contain the aforementioned isotopes and/or other isotopes of other atoms are within the scope of this invention.

Certain isotopically-labeled compounds, radioactive isotopes of the present invention useful in drug and/or substrate tissue distribution assays. Non-limiting examples are $^3$H, $^{14}$C, $^2$H, $^3$H, and carbon-14, which aid in ease of preparation and can afford certain therapeutic advantages resulting from greater metabolic stability. Isotopically labeled compounds of formulae I-IV of this invention, metabolites as described herein, and prodrugs thereof can generally be prepared by carrying out the procedures exemplified below or those known in the art. For example, $^{14}$C-PPTN can be prepared by the methods outlined and exemplified in U.S. Pat. No. 5,552, 412 by substituting a readily available isotopically labeled reagent for a non-isotopically labeled reagent.

In some embodiments, this invention provides compositions comprising the compounds/metabolites as herein described, present in the composition in an effective amount, as further described hereunder. In some embodiments, the term "effective amount" means an amount of compound of the methods of the present invention that is capable of effecting the listed indication, for example, treating the specific disease or pathological condition. The specific dose of a compound administered according to this invention will, of course, be determined by the particular circumstances surrounding the case including, for example, the compound administered, the route of administration, the state of being of the subject, and the severity of the pathological condition being treated.

Biological Activity of Selective Androgen Receptor Modulator Compounds

The processes provided herein are useful in the preparation of metabolites of certain selective androgen receptor modulators (SARMs), which are useful in a variety of applications. This invention provides metabolites of a class of androgen receptor targeting agents (ARTA), or selective androgen receptor modulators (SARMs). The SARM compounds metabolites, either alone or as a composition, are useful for a) binding a selective androgen receptor modulator or metabolite to an androgen receptor; b) suppressing spermatogenesis; c) hormone therapy; d) hormone related therapy; f) inducing the apoptosis in a cancer cell; g) treating cachexia in a human subject; h) treating bone-related disorder in a human subject; i) increasing bone mass in a human subject; j) treating, reducing the severity of, reducing the incidence of, delaying the onset of, or reducing pathogenesis of diabetes in a human subject; k) improving lipid profile; and/or l) treating, reducing the severity of, reducing the incidence of, delaying the onset of, or reducing pathogenesis of fatty liver conditions in a human subject.

In some embodiments, the SARM metabolites possess in vivo tissue selective androgenic and anabolic activity, which is accordingly utilized for particular applications, as will be appreciated by one skilled in the art.

In one embodiment, this invention provides: a) a method of treating a subject having a muscle wasting disorder; b) a method of treating a subject suffering from malnutrition; c) a method of treating a bone-related disorder in a subject; d) a method of increasing a bone mass in a subject; e) a method of improving the lipid profile in a subject; f) a method of treating atherosclerosis and its associated diseases; and g) a method of improving dexterity and movement in a subject, comprising the step of administering to said subject an effective amount of a metabolite of a selective androgen receptor modulator (SARM) compound of formula I-IV, or any metabolite as herein described and/or an analog, derivative, isomer, metabolite, pharmaceutically acceptable salt, pharmaceutical product, hydrate, N-oxide, prodrug, polymorph, impurity or crystal, or any combination thereof.

In some embodiments, the SARMs/metabolites as described herein and/or compositions comprising the same may be used for applications and treating diseases in which the improvement of cognition, reduction or treatment of depression, or other neuroprotective effects are desired.

In some embodiments, the metabolites of the SARMs of compounds I-IV as described herein and/or compositions comprising the same may be used for applications and treating diseases in which the improvement of cognition, reduction or treatment of depression, or other neuroprotective effects are desired. In one embodiment, the glucuronide metabolite of the SARM compound of formula I-IV and/or compositions comprising the same may be used for applications and treating diseases in which the improvement of cognition, reduction or treatment of depression. In another embodiment, the metabolites of the SARM compounds of formulas I-IV may increase the bioavailability, dissolution, improve the pharmacokinetics and reduce the concentration of the active ingredient in the pharmaceutical composition.

In one embodiment, alterations mean any change for the positive or negative, in cognition and/or mood.

In one embodiment, the signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

In one embodiment, any of the methods of this invention or compositions/compounds as described herein are useful or applicable in a subject, which is a human. In another embodiment, the subject is a mammal. In another embodiment the subject is an animal. In another embodiment the subject is an invertebrate. In another embodiment the subject is a vertebrate. In one embodiment, the subject is male. In another embodiment, the subject is female.

In some embodiments, while the methods as described herein may be useful for treating either males or females, females may respond more advantageously to administration of certain compounds, for certain methods, as will be appreciated by one skilled in the art.

In some embodiments, while the methods as described herein may be useful for treating either males or females, males may respond more advantageously to administration of certain compounds, for certain methods, as described herein.

In some embodiments, the SARMs/metabolites as described herein and/or compositions comprising the same may be used for applications in or treating hair loss in males or females. In one embodiment, "hair loss", or "alopecia", refers to baldness as in the very common type of male-pattern baldness.

In some embodiments, the SARMs/metabolites as described herein and/or compositions comprising the same may be used for applications in, or treating diseases or conditions associated with a subject having anemia. In one embodiment, "anemia" refers to the condition of having less than the normal number of red blood cells or less than the normal quantity of hemoglobin in the blood, reduced hematocrit or reduced mean corpuscular volume, or reduced corpuscular size. The oxygen-carrying capacity of the blood is decreased in anemia. In some embodiments, treating anemia may also refer herein to treating underlying factors resulting in anemia, such as for example: a) hemorrhage (bleeding); b) hemolysis (excessive destruction of red blood cells); c) underproduction of red blood cells; and d) not enough normal hemoglobin. In some embodiments, treating anemia in this invention refers to treating any form thereof, including aplastic anemia, benzene poisoning, Fanconi anemia, hemolytic disease of the newborn, hereditary spherocytosis, iron deficiency anemia, pernicious anemia, sickle cell disease, thalassemia, myelodysplastic syndrome, and a variety of bone marrow diseases.

In some embodiments, the SARMs/metabolites as described herein and/or compositions comprising the same may be used for applications in and/or treating diseases and/or conditions associated with problems with a subject's libido, or erectile dysfunction in a subject. In one embodiment, "libido", may refer to sexual desire.

In one embodiment, the term "erectile" refers to the ability to be erect or upright. An erectile tissue is a tissue, which is capable of being greatly dilated and made rigid by the distension of the numerous blood vessels, which it contains.

In another embodiment of the present invention, a method is provided for hormonal therapy in a patient (i.e., one suffering from an androgen-dependent condition) which includes contacting an androgen receptor of a patient with a SARM compound/metabolite as herein described, which in some embodiments behaves as a non steroidal agonist of the androgen receptor, and/or its analog, derivative, isomer, metabolite, pharmaceutically acceptable salt, pharmaceutical product, polymorph, crystal, impurity, hydrate, N-oxide or any combination thereof, in an amount effective to bind the SARM compound or metabolite as herein described to the androgen receptor and effect a change in an androgen-dependent condition.

In one embodiment of this invention, a method is provided for hormone replacement therapy in a patient (i.e., one suffering from an androgen-dependent condition) which includes administering a SARM compound and/or metabolite as herein described and/or its analog, derivative, isomer, pharmaceutically acceptable salt, pharmaceutical product, polymorph, crystal, impurity, hydrate, N-oxide or any combination thereof, to a subject, in an amount sufficient to effect a change in a hormone-dependent condition in the subject.

It is to be understood that reference to the term "compounds of this invention" includes metabolites as herein described, including any embodiment thereof.

Androgen-dependent conditions which may be treated with the compounds and/or compositions as herein described, comprising the methods of the present invention include those conditions which are associated with aging, hypogonadism, sarcopenia, diminished erythropoiesis, osteoporosis, and any other conditions dependent upon low androgen (e.g., testosterone) or estrogen levels.

Androgen-dependent conditions which may be treated with the compounds and/or compositions as herein described, and comprising a method of the invention, may include conditions characterized by elevated androgen or estrogen levels, including hirsutism, infertility, polycystic ovarian syndrome, endometrial carcinoma, breast cancer, male pattern baldness, prostate cancer, testicular cancer, and others, as will be known to one skilled in the art. For such conditions, the subject may be administered a compound as herein described, alone or in combination with another therapeutic agent, as will be appreciated by one skilled in the art.

In one embodiment, this invention provides methods for the treatment of a cancer in a subject, reduction of incidence or severity or pathogenesis of a cancer in a subject, delaying progression, prolonging remission or delaying onset of cancer in a subject, comprising the step of administering to the subject a SARM compound and/or a metabolite as herein described and/or its analog, derivative, isomer, pharmaceutically acceptable salt, pharmaceutical product, polymorph, crystal, impurity, hydrate, N-oxide or any combination thereof. In some embodiments, such cancers are hormone-dependent or associated with reproductive tissue in males or females, such as cancer of the prostate, ovary, breast, uterus, testicle, or others. In one embodiment, the metabolite is the glucuronide metabolite of the SARM compound of formula I-IV.

In some embodiments, this invention provides methods for the treatment of a precancerous precursor or lesion in a subject, reduction of incidence of precancerous precursors or lesions in a subject, comprising the step of administering to the subject a SARM compound and/or metabolite as herein described and/or its analog, derivative, isomer, pharmaceutically acceptable salt, pharmaceutical product, polymorph, crystal, impurity, hydrate, N-oxide or any combination thereof. In some embodiments, such precancerous precursors are found in hormone-responsive tissue or are associated with reproductive tissue in males or females, such as in the prostate, ovary, breast, uterus, testicle, or others. In some embodiments, such precancerous precursors comprise any local intraepithelial neoplasia, for example, of the prostate, the cervix, etc. In some embodiments, such methods are useful in treating neoplasia or pre-neoplasia, dysplasia or hyperplasia in a tissue, such as in reproductive tissue in males or females.

In some embodiments, this invention provides for the use of a SARM compound metabolite/s as herein described, or its prodrug, analog, isomer, derivative, pharmaceutically acceptable salt, pharmaceutical product, polymorph, crystal, impurity, N-oxide, hydrate or any combination thereof, for treating reducing the severity of, reducing the incidence of, or reducing pathogenesis of cachexia and/or cachexia associated with cancer in a subject. In another embodiment, the metabolite is the glucuronide metabolite of the SARM compound of formula I-IV. In another embodiment, the cancer comprises adrenocortical carcinoma, anal cancer, bladder cancer, brain tumor, brain stem glioma, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, Ewings family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell lung cancer, small cell lymphoma, Hodgkins lymphoma, non-Hodgkins lymphoma, AIDS-related lymphoma, central nervous system (primary), lymphoma, cutaneous T-cell, lymphoma, malignant mesothelioma, melanoma, Merkel cell carcinoma, metastatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof.

In another embodiment, this invention provides for the use of a SARM compound metabolite/s as herein described, or its prodrug, analog, isomer, derivative, pharmaceutically acceptable salt, pharmaceutical product, polymorph, crystal, impurity, N-oxide, hydrate or any combination thereof, for treating reducing the severity of, reducing the incidence of, delaying the onset of lung cancer, which in one embodiment is non-small cell lung cancer.

A wasting condition or disorder is defined herein as a condition or disorder that is characterized, at least in part, by an abnormal, progressive loss of body, organ or tissue mass. A wasting condition can occur as a result of a pathology such as, for example, cancer, or an infection, or it can be due to a physiologic or metabolic state, such as disuse deconditioning that can occur, for example, due to prolonged bed rest or when a limb is immobilized, such as in a cast. A wasting condition can also be age associated. The loss of body mass that occurs during a wasting condition can be characterized by a loss of total body weight, or a loss of organ weight such as a loss of bone or muscle mass due to a decrease in tissue protein.

In one embodiment, "muscle wasting" or "muscular wasting", used herein interchangeably, refer to the progressive loss of muscle mass and/or to the progressive weakening and degeneration of muscles, including the skeletal or voluntary muscles which control movement, cardiac muscles which control the heart, and smooth muscles, and may be a result of a pathology, disease, condition or disorder. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

In one embodiment, the muscle wasting may be due to chronic or acute, or in some embodiments, may represent a genetic etiology.

In some embodiments, the metabolites of this invention may be utilized to treat any disease, disorder or condition whose etiology is due to advanced age, immobilization (e.g. as in hospitalization), alcoholism, burns, trauma, cancer, injuries or damage to the central nervous system, including but not limited examples are central nerve injury or damage, peripheral nerve injury or damage and spinal cord injury or damage, which in some embodiments, results in muscle wasting. In some embodiments, the etiology of muscle wasting may be neurological or infectious.

Genetic disorder arising in muscle diseases treatable with the compounds as described herein include but are not limited to muscular dystrophy; muscle atrophy; X-linked spinal-bulbar muscular atrophy (SBMA), duchenne muscular dystrophy, myotonic dystrophy, duchenne muscular dystrophy, becker muscular dystrophy, limb-girdle muscular dystrophy, facioscapulhumeral muscular dystrophy, congenital muscular dystrophy, oculopharyngeal muscular dystrophy, distal muscular dystrophy, emery-dreifuss muscular dystrophy, post-Polio, X-linked spinal-bulbar muscular atrophy (SBMA—also known as Kennedy's Disease).

The loss of muscle mass that occurs during muscle wasting can be characterized by a muscle protein breakdown or degradation, by muscle protein catabolism.

The term "catabolism" has its commonly known meaning in the art, specifically an energy burning form of metabolism associate with loss of muscle mass.

In one embodiment, the invention provides a use of SARM compound metabolite/s as described herein or its prodrug, analog, isomer, derivative, pharmaceutically acceptable salt, pharmaceutical product, polymorph, crystal, impurity, N-oxide, hydrate or any combination therefore the treatment of a wasting disease, disorder or condition in a subject.

This invention is directed to treating, in some embodiments, any wasting disorder, which may be reflected in muscle wasting, weight loss, malnutrition, starvation, or any wasting or loss of functioning due to a loss of tissue mass.

In some embodiments, wasting diseases or disorders, such as cachexia; malnutrition, tuberculosis, leprosy, diabetes, renal disease, chronic obstructive pulmonary disease (COPD), cancer, end stage renal failure, sarcopenia, emphysema, osteomalacia, or cardiomyopathy, may be treated by the methods of this invention, via the administration of a SARM compound metabolite/s as herein described, compositions comprising the same, with or without additional drugs, compounds, or agents, which provide a therapeutic effect for the condition being treated.

In some embodiments, wasting is due to infection with enterovirus, Epstein-Barr virus, herpes zoster, HIV, trypanosomes, influenza, coxsackie, rickettsia, trichinella, schistosoma or mycobacteria, and this invention, in some embodiments, provides methods of treatment thereof.

"Cachexia" is weakness and a loss of weight caused by a disease or as a side effect of illness. For example, cardiac cachexia, cancer cachexia, cachexia associated with acquired immunodeficiency syndrome (AIDS) and infection with the human immunodeficiency virus (HIV).

In some embodiments, the present invention provides a method for treating, reducing the incidence, delaying the onset or progression, or reducing and/or abrogating the symptoms associated with a musculoskeletal disease in a subject.

In one embodiment, this invention provides compounds, compositions and/or methods of use thereof in treating benign prostate hyperplasia (BPH) and its associated morbidities, such as frequent urge to urinate, incomplete bladder emptying, lack of control over urination, inability to empty the bladder, incontinence, urinary obstruction and urinary failure.

In another embodiment of the present invention, the method for treating benign prostate hyperplasia (BPH) in a subject, comprises the step of administering to the subject a SARM compound and/or a metabolite as herein described and/or its analog, derivative, isomer, metabolite, pharmaceutically acceptable salt, pharmaceutical product, polymorph, crystal, impurity, hydrate, N-oxide or any combination thereof, in an amount effective to treat BPH in the subject. In another embodiment, the metabolite is the glucuronide metabolite of the SARM compound of formula I-IV.

In one embodiment, this invention provides for the use of a SARM compound metabolite/s as herein described, or its prodrug, analog, isomer, derivative, pharmaceutically acceptable salt, pharmaceutical product, polymorph, crystal, impurity, N-oxide, hydrate or any combination thereof, for a) treating a bone related disorder; b) preventing a bone related disorder; c) suppressing a bone related disorder; d) inhibiting a bone related disorder; e) increasing a strength of a bone of a subject; f) increasing a bone mass in a subject; g) use for osteoclastogenesis inhibition. In another embodiment, the metabolite is the glucuronide metabolite of the SARM compound of formula I-IV.

In one embodiment, the bone related disorder is a genetic disorder, or in another embodiment, is induced as a result of a treatment regimen for a given disease. For example, and in one embodiment, the SARMs compound metabolites/s as herein described are useful in treating a bone-related disorder that arises as a result of cancer metastasis to bone, or in another embodiment, as a result of androgen-deprivation therapy, for example, given in response to prostate carcinogenesis in the subject.

In one embodiment, the bone-related disorder is osteoporosis. In another embodiment, the bone-related disorder is osteopenia. In another embodiment, the bone-related disorder is increased bone resorption. In another embodiment, the bone-related disorder is bone fracture. In another embodiment, the bone-related disorder is bone frailty.

In another embodiment, the bone-related disorder is a loss of bone mineral density (BMD). In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein in another embodiment, bones that are affected by osteoporosis can fracture with only a minor fall or injury that normally would not cause a bone fracture. It is to be understood that any treatment or amelioration of osteoporosis or symptoms related thereto effected by administration of a metabolite of this invention is to be considered part of this invention.

According to this aspect of the invention and in one embodiment, the bone-related disorder is treated with a SARM compound metabolite/s as herein described, or a combination thereof. In another embodiment, other bone-stimulating compounds can be provided to the subject, prior to, concurrent with or following administration of a SARM metabolite/s as herein described. In one embodiment, such a bone stimulating compound may comprise natural or synthetic materials.

In one embodiment, the bone stimulating compound may comprise a bone morphogenetic protein (BMP), a growth factor, such as epidermal growth factor (EGF), a fibroblast growth factor (FGF), a transforming growth factor (TGF, an insulin growth factor (IGF), a platelet-derived growth factor (PDGF) hedgehog proteins such as sonic, indian and desert hedgehog, a hormone such as follicle stimulating hormone, parathyroid hormone, parathyroid hormone related peptide, activins, inhibins, follistatin, frizzled, frzb or frazzled proteins, BMP binding proteins such as chordin and fetuin, a cytokine such as IL-3, IL-7, GM-CSF, a chemokine, such as eotaxin, a collagen, osteocalcin, osteonectin and others, as will be appreciated by one skilled in the art.

In another embodiment, the compositions for use in treating a bone disorder of this invention may comprise a SARM metabolite/s as herein described, an additional bone stimulating compound, or compounds, and osteogenic cells. In one embodiment, an osteogenic cell may be a stem cell or progenitor cell, which may be induced to differentiate into an osteoblast. In another embodiment, the cell may be an osteoblast. In another embodiment, nucleic acids which encode bone-stimulating compounds may be administered to the subject, which is to be considered as part of this invention.

The treatments as herein described allow for combination therapies suitable for a particular application and according to this aspect the metabolite may be administered with additional SARMs, SERMs and other bone stimulating compounds as herein described In another embodiment, the methods of the present invention comprise administering the SARM compound metabolite/s as herein described, in combination with bisphosphonates such as alendronate, etidronate, alendronate, zoledronate, ibandronate, risedronate, or homoresidronate or combinations thereof for treating osteoporosis.

In another embodiment, the methods of the present invention comprise administering the SARM compound metabolite/s as herein described, in combination with Calcitonin such as salmon, Elcatonin, SUN-8577 or TJN-135 for treating osteoporosis.

In another embodiment, the methods of treating osteoporosis of the present invention comprise administering the SARM compound and/or metabolite as herein described, in combination with a) vitamin D or derivative such as ZK-156979; b) vitamin D receptor ligand and analogues such as calcitriol, topitriol, ZK-150123, TEI-9647, BXL-628, Ro-26-9228, BAL-2299, Ro-65-2299 or DP-035; c) estrogen, estrogen derivative, or conjugated estrogens; d) antiestrogen, progestins, or synthetic estrogen/progestins; e) RANK ligand mAb such as denosumab formerly AMG162 (Amgen); and f) dietary calcium supplement or combinations thereof.

In one embodiment, the methods of this invention are useful in treating diseases or disorders caused by, or associated with a hormonal disorder, disruption or imbalance.

In one embodiment, the hormonal disorder, disruption or imbalance comprises an excess of a hormone. In another embodiment, the hormonal disorder, disruption or imbalance comprises a deficiency of a hormone. In one embodiment, the hormone is a steroid hormone. In another embodiment, the hormone is an estrogen. In another embodiment, the hormone is an androgen. In another embodiment, the hormone is a glucocorticoid. In another embodiment, the hormone is Luteinizing Hormone (LH). In another embodiment, the hormone is Follicle Stimulating Hormone (FSH). In another embodiment, the hormone is any other hormone known in the art. In another embodiment, the hormonal disorder, disruption or imbalance is associated with menopause. In another embodiment, hormone deficiency is a result of specific manipulation, as a byproduct of treating a disease or disorder in the subject. For example, the hormone deficiency may be a result of androgen depletion in a subject, as a therapy for prostate cancer in the subject. Each possibility represents a separate embodiment of the present invention.

In another embodiment, the administering step includes intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

In some embodiments, the present invention provides a method for treating, reducing the incidence, delaying the onset or progression, or reducing and/or abrogating the symptoms associated with an infection in a subject. In one embodiment, the method comprises administering to a subject a composition comprising a SARM compound and/or metabolite as herein described and an immunomodulating agent, an anti-infective agent, a gene therapy agent, or a combination thereof.

In one embodiment, the method comprises administering to a subject a composition comprising a SARM compound and/or metabolite as herein described and an anti-cancer agent, an immunomodulating agent, an antidiabetic agent, an agent treating the central nervous system, an agent treating a metabolic disease, an agent treating a wasting disease, a gene therapy agent, an agent treating the endocrine system, vitamins, or a combination thereof.

In some embodiments, the present invention provides a method for treating, reducing the incidence, delaying the onset or progression, or reducing and/or abrogating the symptoms associated with a digestive system disease in a subject. In one embodiment, the method comprises administering to a subject a composition comprising a SARM compound and/or metabolite as herein described and an anti-cancer agent, an immunomodulating agent, an antidiabetic agent, an agent treating the central nervous system, an agent treating the gastrointestinal system, an anti-infective agent, an agent treating a metabolic disease, a gene therapy agent, an agent treating the endocrine system, vitamins, or a combination thereof. In some embodiments, gastrointestinal diseases comprise adenomatous polyposis coli, ulcerative colitis, Crohn's disease, deglutition disorders, enterocolitis, pseudomembranous disease, esophageal atresia, esophagitis, exocrine pancreatic insufficiency, fatty liver, gastritis, hernia, liver cirrhosis, liver diseases, rectal diseases, Whipple's disease, or Zollinger-Ellison syndrome. Related diseases which may be treated or symptoms ameliorated by administration of the SARM metabolite/s of this invention may be found in The Merck Manual, 18$^{th}$ edition (Merck Research Laboratories, Whitehouse Station, N.J.), which is incorporated herein by reference.

In some embodiments, the present invention provides a method for treating, reducing the incidence, delaying the onset or progression, or reducing and/or abrogating the symptoms associated with a stomatognathic disease in a subject. In one embodiment, the method comprises administering to a subject a composition comprising a SARM compound and/or metabolite as herein described and an anti-cancer agent, an immunomodulating agent, an anti-infective agent, an agent treating a wasting disease, a gene therapy agent, an agent treating the endocrine system, vitamins, or a combination thereof. In some embodiments, stomatognathic diseases comprise ankyloglossia, bruxism, burning mouth syndrome, cheilitis, cherubism, cleft lip, dentigerous cyst, gingivitis, glossitis, benign migratory, herpes labialis, sialorrhea, stomatitis, aphthous, temporomandibular joint disorders, temporomandibular joint dysfunction syndrome, or xerostomia. elated diseases which may be treated or symptoms ameliorated by administration of the SARM metabolite/s of this invention may be found in The Merck Manual, 18$^{th}$ edition (Merck Research Laboratories, Whitehouse Station, N.J.), which is incorporated herein by reference.

In some embodiments, the present invention provides a method for treating, reducing the incidence, delaying the onset or progression, or reducing and/or abrogating the symptoms associated with a respiratory tract disease in a subject. In one embodiment, the method comprises administering to a subject a composition comprising a SARM compound and/or metabolite as herein described and an anti-cancer agent, an immunomodulating agent, an agent treating the central nervous system, an agent treating the cardiovascular system, an anti-infective agent, an agent treating a wasting disease, a gene therapy agent, an agent treating the endocrine system, vitamins, or a combination thereof. In some embodiments, respiratory tract diseases comprise airway obstruction, apnea, asbestosis, asthma, atelectasis, bronchiolitis, hypertension, pulmonary hypertension, pneumonia, pneumothorax, chronic obstructive, pulmonary edema, pulmonary embolism, pulmonary emphysema, pulmonary fibrosis, Wegener's granulomatosis, or whooping cough. Related diseases which may be treated or symptoms ameliorated by administration of the SARM metabolite/s of this invention may be found in The Merck Manual, 18$^{th}$ edition (Merck Research Laboratories, Whitehouse Station, N.J.), which is incorporated herein by reference.

In some embodiments, the present invention provides a method for treating, reducing the incidence, delaying the onset or progression, or reducing and/or abrogating the symptoms associated with an otorhinolaryngologic disease in a subject. In one embodiment, the method comprises administering to a subject a composition comprising a SARM compound and/or metabolite as herein described and an anti-cancer agent, an immunomodulating agent, an anti-infective agent, an agent treating a wasting disease, a gene therapy agent, an agent treating the endocrine system, vitamins, or a combination thereof. In some embodiments, otorhinolaryngologic diseases comprise cholesteatoma, middle ear, Meniere's disease, otitis, pharyngitis, presbycusis, tinnitus, tonsillitis, vestibular neuronitis, vocal cord paralysis, or voice disorders. Related diseases which may be treated or symptoms ameliorated by administration of the SARM metabolite/s of this invention may be found in The Merck Manual, 18$^{th}$ edition (Merck Research Laboratories, Whitehouse Station, N.J.), which is incorporated herein by reference.

In some embodiments, the present invention provides a method for treating, reducing the incidence, delaying the onset or progression, or reducing and/or abrogating the symptoms associated with a nervous system disease in a subject. In one embodiment, the method comprises administering to a subject a composition comprising a SARM compound and/or metabolite as herein described and an anti-cancer agent, an immunomodulating agent, an agent treating the central nervous system, an anti-infective agent, an agent treating a metabolic disease, an agent treating a wasting disease, a gene therapy agent, an agent treating the endocrine system, vitamins, or a combination thereof. In some embodiments, nervous system diseases comprise autonomic nervous system diseases, central nervous system diseases, cranial nerve diseases, demyelinating diseases, nervous system malformations, neurologic manifestations, or neuromuscular diseases.

In some embodiments, autonomic nervous system diseases comprise causalgia, or reflex sympathetic dystrophy.

In some embodiments, central nervous system diseases comprise Alzheimer's disease, cerebral palsy, cerebrovascular disorders, Creutzfeldt-Jakob syndrome, Dandy-Walker syndrome, dementia, encephalitis, Huntington disease, hydrocephalus, meningitis, Parkinson's disease, parkinsonian disorders, spinal cord diseases, supranuclear palsy, syringomyelia, or tourette syndrome In some embodiments, the central nervous system disease is cystic fibrosis induced hypogonadal state.

In some embodiments, cranial nerve diseases comprise bell palsy, cranial nerve diseases, facial hemiatrophy, facial neuralgia, glossopharyngeal nerve diseases, Moebius syndrome, or trigeminal neuralgia.

In some embodiments, central nervous system diseases comprise injuries or damage to the central nervous system (CNS). damage.

A CNS injury includes, for example and without limitation, damage to retinal ganglion cells, a traumatic brain injury, a stroke-related injury, a cerebral aneurism-related injury, a spinal cord injury, including monoplegia, diplegia, paraplegia, hemiplegia and quadriplegia, a neuroproliferative disorder, or neuropathic pain syndrome.

A severing of the spinal cord, also referred to herein as a "transection," may be a complete severing or, may be an incomplete severing of the spinal cord.

In some embodiments, the methods of treating a subject suffering form a CNS injury or, in other embodiments, spinal cord injury, may be accompanied by treatment of the subject with electrical stimulation of the injured site and the administration of a purine nucleoside, or analog thereof, for example as described in United States Patent Application Publication Number 20040214790A1.

In some embodiments, demyelinating diseases comprise adrenoleukodystrophy, alexander disease, canavan disease, demyelinating disease, diffuse cerebral sclerosis of schilder, leukodystrophy-globoid cell, leukodystrophy-metachromatic, multiple sclerosis, or neuromyelitis optica.

In some embodiments, nervous system malformations comprise Arnold-Chiari malformation, Charcot-Marie-Tooth disease, encephalocele, hereditary motor and sensory neuropathies, septo-optic dysplasia, spina bifida occulta, or spinal dysraphism.

In some embodiments, neurologic manifestations comprise agnosia, amnesia, anomia, aphasiadystonia, facial paralysis, myoclonus, neck pain, nonverbal learning disorder, olfaction disorders, pain, paralysis, phantom limb, synesthesia tardive dyskinesia, taste disorders, or vertigo.

In some embodiments, neuromuscular diseases comprise amyotrophic lateral sclerosis, brachial plexus neuritis, brachial plexus neuropathies, bulbar palsy, guillain, barre syndrome, congenital, nerve compression syndromes, neuralgia, or thoracic disease.

In one embodiment, methods of treating a subject with a nervous system disease encompass treating any secondary conditions in the subject, which arise due to the subject having a nervous system disease, some of which are described herein. Related diseases which may be treated or symptoms ameliorated by administration of the SARM metabolite/s of this invention may be found in The Merck Manual, 18$^{th}$ edition (Merck Research Laboratories, Whitehouse Station, N.J.), which is incorporated herein by reference.

In some embodiments, the present invention provides a method for treating, reducing the incidence, delaying the onset or progression, or reducing and/or abrogating the symptoms associated with an ophthalmic disease in a subject. In one embodiment, the method comprises administering to a subject a composition comprising a SARM compound metabolite/s as herein described and an anti-cancer agent, an immunomodulating agent, an agent treating the cardiovascular system, an anti-infective agent, an agent treating a wasting disease, a gene therapy agent, an agent treating the endocrine system, vitamins, or a combination thereof.

In some embodiments, the present invention provides a method for treating, reducing the incidence, delaying the onset or progression, or reducing and/or abrogating the symptoms associated with an urologic and/or male genital disease in a subject. In one embodiment, the method comprises administering to a subject a composition comprising a SARM compound metabolite/s and an anti-cancer agent, an immunomodulating agent, an antidiabetic agent, an agent treating the gastrointestinal system, an anti-infective agent, an agent treating the kidney, an agent treating a metabolic disease, an agent treating a wasting disease, a gene therapy agent, an agent treating the endocrine system, vitamins, or a combination thereof. In some embodiments, the present invention provides a method for treating, reducing the incidence, delaying the onset or progression, or reducing and/or abrogating the symptoms associated with a dermatological disorder in a subject. In one embodiment, the method comprises administering to a subject a composition comprising a SARM compound metabolite/s and anti-cancer agent, an immunomodulating agent, an agent treating a dermatological disorder, an anti-infective agent, a gene therapy agent, an agent treating the endocrine system, vitamins, or a combination thereof.

In one embodiment, the dermatological disorder is a wound or a burn. In one embodiment, the term "wound" denotes a bodily injury with disruption of the normal integrity of tissue structures. The term is also intended to encompass the terms "sore", "lesion", "necrosis" and "ulcer". In one embodiment, the term "sore" refers to any lesion of the skin or mucous membranes and the term "ulcer" refers to a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions. All of these are encompassed by the term "wound".

The kinds of wounds to be treated according to the invention include also i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is as i) small tissue loss due to surgical incisions, minor abrasions and minor bites, or as ii) significant tissue loss. The latter group includes ischemic ulcers, pressure sores, fistulae, lacerations, severe bites, thermal burns and donor site wounds (in soft and hard tissues) and infarctions.

In other aspects of the invention, the wound to be prevented and/or treated is selected from the group consisting of aseptic wounds, infarctions, contused wounds, incised wounds, lacerated wounds, non-penetrating wounds, open wounds, penetrating wounds, perforating wounds, puncture wounds, septic wounds and subcutaneous wounds.

Other wounds which are of importance in connection with the present invention are wounds like ischemic ulcers, pressure sores, fistulae, severe bites, thermal burns and donor site wounds.

Donor site wounds are wounds which e.g. occur in connection with removal of hard tissue from one part of the body to another part of the body e.g. in connection with transplantation. The wounds resulting from such operations are very painful and an improved healing is therefore most valuable.

The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

In some embodiments, burns are associated with reduced testosterone levels, and hypgonadism is associated with delayed wound healing. In one embodiment, the methods of this invention, provide for treating a subject suffering from a wound or a burn.

In some embodiments, the present invention provides a method for treating, reducing the incidence, delaying the onset or progression, or reducing and/or abrogating the symptoms associated with an endocrine disorder in a subject. In one embodiment, the method comprises administering to a subject a composition comprising a SARM compound metabolite/s as herein described and anti-cancer agent, an immunomodulating agent, an antidiabetic agent, an agent treating the cardiovascular system, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, endocrine disorders comprise acromegaly, Addison disease, adrenal gland diseases, adrenal hyperplasia, congenital, androgen-insensitivity syndrome, congenital hypothyroidism, Cushing syndrome, diabetes insipidus, diabetes mellitus, diabetes mellitus-type 1, diabetes mellitus-type 2, diabetic ketoacidosis, empty Sella syndrome, endocrine gland neoplasms, endocrine system diseases, gigantism, gonadal disorders, graves disease, hermaphroditism, hyperaldosteronism, hyperglycemic hyperosmolar nonketotic coma, hyperpituitarism, hyperprolactinemia, hyperthyroidism, hypogonadism, hypopituitarism, hypothyroidism, Kallmann syndrome, Nelson syndrome, parathyroid diseases, pituitary diseases, polyendocrinopathies, autoimmune, puberty, delayed puberty, precocious, renal osteodystrophy, thyroid diseases, thyroid hormone resistance syndrome, thyroid neoplasms, thyroid nodule, thyroiditis, thyroiditis, autoimmune, thyroiditis, subacute, or Wolfram syndrome.

In one embodiment, "Hypogonadism" is a condition resulting from or characterised by abnormally decreased functional activity of the gonads, with retardation of growth and sexual development.

In some embodiments, the present invention provides a method for treating, reducing the incidence, delaying the onset or progression, or reducing and/or abrogating the symptoms associated with urogenital disease and/or fertility in a subject. In one embodiment, the method comprises administering to a subject a composition comprising a SARM compound and/or metabolite as herein described and an anti-cancer agent, an immunomodulating agent, an anti-infective agent, an agent treating the kidney, gene therapy agent, an agent treating the endocrine system, vitamins, or a combination thereof. In some embodiments, urogenital diseases and/or fertility diseases comprise abortion, spontaneous-adhesions-pelvic, eclampsia, endometriosis, fetal death, fetal growth retardation, premature rupture female genital neoplasms, female hydatidiform mole, ovarian cysts, or polycystic ovary syndrome. Related diseases which may be treated or symptoms ameliorated by administration of the SARM metabolite/s of this invention may be found in The Merck Manual, $18^{th}$ edition (Merck Research Laboratories, Whitehouse Station, N.J.), which is incorporated herein by reference.

In some embodiments, the present invention provides a method for treating, reducing the incidence, delaying the onset or progression, or reducing and/or abrogating the symptoms associated with hemic and/or lymphatic disease in a subject. In one embodiment, the method comprises administering to a subject a composition comprising a SARM compound metabolite/s as herein described and an anti-cancer agent, an immunomodulating agent, an antidiabetic agent, an agent treating the cardiovascular system, an anti-infective agent, an agent treating the liver, an agent treating the kidney, an agent treating a metabolic disease, a gene therapy agent, an agent treating the endocrine system, vitamins, or a combination thereof. In some embodiments, hemic and/or lymphatic diseases comprise afibrinogenemia, anemia, sickle cell anemia, angiolymphoid hyperplasia with eosinophilia, antithrombin III deficiency, Bemard-Soulier syndrome, blood coagulation disorders, blood platelet disorders, Chediak-Higashi syndrome, cryoglobulinemia, disseminated intravascular coagulation, factor V deficiency, factor VII deficiency, factor X deficiency, factor XI deficiency, factor XII deficiency, fanconi anemia, giant lymph node hyperplasia, histiocytosis, leukopenia, lymphadenitis, lymphangioleiomyomatosis, lymphedema, methemoglobinemia, myeloproliferative disorders, neutropenia, sarcoidosis, sarcoidosis spherocytosis, thalassemia, thrombocytopenia, or Waldenstrom macroglobulinemia. Related diseases which may be treated or symptoms ameliorated by administration of the SARM metabolite/s of this invention may be found in The Merck Manual, $18^{th}$ edition (Merck Research Laboratories, Whitehouse Station, N.J.), which is incorporated herein by reference.

In some embodiments, connective tissue diseases comprise ankylosing spondylitis, Ehlers-Danlos syndrome, Henoch-Schonlein purpura, Kawasaki disease, Marfan syndrome, polyarteritis nodosa, polymyositis, psoriatic arthritis, reactive arthritis, rheumatoid arthritis, scleroderma, Sjogren's syndrome, Still's disease, systemic lupus erythematosus, Takayasu disease, or Wegener's granulomatosis.

In some embodiments, the present invention provides a method for treating, reducing the incidence, delaying the onset or progression, or reducing and/or abrogating the symptoms associated with a metabolic disease in a subject.

In some embodiments, metabolic diseases comprise acid-base imbalance, amino acid metabolism inborn errors, amyloidosis, iron-deficiency anemia, ascorbic acid deficiency, avitaminosis, beriberi, fatty acid oxidation disorders, galactosemias, Gaucher disease, Gilbert disease, glucosephosphate dehydrogenase deficiency, rickets, Sandhoff disease, starvation, tangier disease, Tay-Sachs disease, tetrahydrobiopterin deficiency, trimethylaminuria, tyrosinemias, urea cycle disorders, water-electrolyte imbalance, Wernicke encephalopathy, Wolman disease, or Zellweger syndrome. Related diseases which may be treated or symptoms ameliorated by administration of the SARM metabolite/s of this invention may be found in The Merck Manual, 18$^{th}$ edition (Merck Research Laboratories, Whitehouse Station, N.J.), which is incorporated herein by reference.

In some embodiments, the present invention provides a method for treating, reducing the incidence, delaying the onset or progression, or reducing and/or abrogating the symptoms associated with a disorder of environmental origin in a subject. In some embodiments, disorders of environmental origin comprise barotrauma, bites and stings, brain concussion, burns, central cord syndrome, craniocerebral trauma, electric injuries, fractures, frostbite, heat stress disorders, motion sickness, occupational diseases, poisoning, shaken baby syndrome, shoulder injuries, space motion sickness, spinal cord injuries, tick paralysis, or wounds (penetrating and non-penetrating).

In some embodiments, the present invention provides a method for treating, reducing the incidence, delaying the onset or progression, or reducing and/or abrogating the symptoms associated with a mental disorder in a subject.

In one embodiment, "depression" refers to an illness that involves the body, mood and thoughts that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

In one embodiment, "cognition" refers to the process of knowing, specifically the process of being aware, knowing, thinking, learning and judging. Cognition is related to the fields of psychology, linguistics, computer science, neuroscience, mathematics, ethology and philosophy. In one embodiment, "mood" refers to a temper or state of the mind. As contemplated herein, alterations mean any change for the positive or negative, in cognition and/or mood.

In some embodiments, the present invention provides a method for treating, reducing the incidence, delaying the onset or progression, or reducing and/or abrogating the symptoms associated with a liver disease in a subject. In some embodiments, liver diseases comprise liver cancer, primary biliary cirrhosis, autoimmune hepatitis, chronic liver disease, cirrhosis of the liver, hepatitis, viral hepatitis, liver failure, jaundice, neonatal jaundice, hepatoma, liver cancer, liver abscess, alcoholic liver disease, hemochromatosis, Wilson's disease, portal hypertension, primary sclerosing cholangitis, sarcoidosis, tapeworms, alveolar hydatid disease, fascioliasis, schistosomiasis, gaucher disease, Zellweger syndrome, alcoholism, food poisoning, pneumococcal pneumonia' or vibrio vulnificus. Related diseases which may be treated or symptoms ameliorated by administration of the SARM metabolite/s of this invention may be found in The Merck Manual, 18$^{th}$ edition (Merck Research Laboratories, Whitehouse Station, N.J.), which is incorporated herein by reference.

In some embodiments, the present invention provides a method for treating, reducing the incidence, delaying the onset or progression, or reducing and/or abrogating the symptoms associated with a kidney disease in a subject.

In one embodiment, the kidney disease or disorder is acute, or in another embodiment, chronic In one embodiment, the methods of this invention are useful in subjects predisposed to kidney diseases or disorders. In one embodiment, the phrase "predisposed to a kidney disease or disorder" with respect to a subject is synonymous with the phrase "subject at risk", and includes a subject at risk of acute or chronic renal failure, or at risk of the need for renal replacement therapy, if the subject is reasonably expected to suffer a progressive loss of renal function associated with progressive loss of functioning nephron units. Whether a particular subject is at risk is a determination which may routinely be made by one of ordinary skill in the relevant medical or veterinary art.

In one embodiment, subjects with kidney disease, in particular male subjects with end-stage renal disease (ESRD) suffer from hypogonadism, with some having concomitant moderate to severe protein-energy malnutrition (PEM), which leads to higher required doses of EPO, lower QOL scores, and higher mortality.

In one embodiment, diabetic nephropathy is a complication of diabetes that evolves early, typically before clinical diagnosis of diabetes is made.

Hypertension is another comorbid factor for renal disease. In some embodiments, treatment of renal disease according to the present invention may comprise concomitant treatment with a SARM compound metabolite/s as herein described and an agent which treats hypertension.

In some embodiments, the present invention provides a method for treating, reducing the incidence, delaying the onset or progression, or reducing and/or abrogating the symptoms associated with a hypogonadal state in a subject. In one embodiment, the present invention provides a method for treating, reducing the incidence, delaying the onset or progression, or reducing and/or abrogating the symptoms associated with a pharmacotherapy induced hypogonadal state in a subject. In some embodiments, hypogonadism is caused by treatments which alter the secretion of hormones from the sex glands in both women and men. In some embodiments, hypogonadism may be "primary" or "central." In primary hypogonadism, the ovaries or testes themselves do not function properly. In some embodiments, hypogonadism may be induced by surgery, radiation, genetic and developmental disorders, liver and kidney disease, infection, or certain autoimmune disorders. In some embodiments, menopause is a form of hypogonadism. Menopause may cause, in some embodiments, hot flashes, vaginal dryness, or irritability due to woman's estrogen levels fall.

In some embodiments, the present invention provides a method for treating, reducing the incidence, delaying the onset or progression, or reducing and/or abrogating the symptoms associated with osteopenic state in a subject.

In some embodiments, the present invention provides a method for enhanced production such as milk, sperm, or egg. In some embodiments, the present invention provides a method for enhanced production of lean meats or eggs. In some embodiments, the present invention provides a method for increased productivity of feeds or stud livestock, for example, increased sperm count, improved morphology of sperm, etc. In some embodiments, the present invention provides a method for expanding the productive life of farm animals, for example, egg-laying hens, milk-producing cows, etc, and/or enhanced herd health, for example, improved immune clearance, stronger animals.

In another embodiment, this invention provides a method of treating Opioid Induced Androgen Deficiency (OPIAD), the method comprising administering to the subject a SARM as herein described, and optionally opiates, opioids, narcotics, etc. methadone, long-acting opiates/opioids such as Kadian, extended release morphines, all opiates/opioids/narcotics agents approved by FDA, opiates/opioids used in treatment of heroin addiction, opiates/opioids used in the treatment of chronic pain of malignancy, opiates/opioids used in the treatment non-malignant of chronic pain syndromes.

In another embodiment, this invention provides a method of treating a nervous system disease, disorder or condition, the method comprising administering to the subject a SARM as herein described, and optionally anti-psychotics, such as, for example, zotepine, haloperidol, amisulpride, risperidone, other D2 dopamine receptor antagonists; anti-epileptics, such as valproic acid, carbamazepine, oxcarbamazepine, etc. or combinations thereof.

In another embodiment, this invention provides a method of treating a hormone dependent disease, disorder or condition, the method comprising administering to the subject a SARM metabolite/s as herein described, and optionally chemotherapeutics agents and therapies (methotrexate, cyclophosphamide, ifosfamide, adriamycin, doxorubicin, glucocorticoids, cyclosporine, L-thyroxine, selective estrogen receptor modulators (SERMs), aromatase inhibitors (AI), fulvestrant, gonadotropin releasing hormone (GnRH) agents, ADT, discontinuation of hormone replacement therapy, cranial irradiation, peripheral irradiation, etc.; prolactinemia-inducing pharmacotherapeutics (serotonergic antidepressants acting through $5HT_2$ receptors, selective serotonin reuptake inhibitors, monoamine oxidase inhibitors, tricyclic antidepressants, antihypertensives such as methyldopa, reserpine, clonidine, and verapamil; antidopaminergic anti-emetics such as metoclopramide, $H_2$ receptor antagonists such as cimetidine and ranitidine, estrogens, amphetamines, AR partial antagonists (ketoconazole, spironolactone, eplerenone) or combinations thereof.

In another embodiment, the SARMs and compositions as described herein are useful in promoting or speeding recovery following a surgical procedure.

In another embodiment, the subject has a hormonal imbalance, disorder, or disease. In another embodiment the subject has menopause.

In one embodiment, the SARM compounds and/or metabolite as herein described alter the levels of leptin in a subject. In another embodiment, the SARM compounds and/or metabolite as herein described decrease the levels of leptin. In another embodiment, the SARM compounds and/or metabolite as herein described increase the levels of leptin in a subject.

The SARM compounds and/or metabolite as herein described, in one embodiment, affect circulating, or in another embodiment, tissue levels of leptin. In one embodiment, the term 'level/s of leptin' refers to the serum level of leptin. As contemplated herein, the SARM compounds and/or metabolite as herein described have an effect on leptin in vitro and in vivo.

The term "obesity" is defined, in one embodiment, as an increase in body weight beyond the limitation of skeletal and physical requirement, as the result of excessive accumulation of fat in the body.

The term "obesity-associated metabolic disorder" refers, in one embodiment, to a disorder which results from, is a consequence of, is exacerbated by or is secondary to obesity. Non-limiting examples of such a disorder are osteoarthritis, Type II diabetes mellitus, increased blood pressure, stroke, and heart disease.

Cholesterol, triacylglycerol and other lipids are transported in body fluids by lipoproteins which may be classified according to their density, for example, the very low density lipoproteins (VLDL), intermediate density lipoproteins (IDL), low density lipoproteins (LDL) and high density lipoproteins (HDL).

In one embodiment, this invention provides methods of use of the SARM compounds metabolite/s as herein described for improving the lipid profile and/or reducing the circulating lipid levels in a subject. In some embodiments, according to this aspect of the invention, the subject suffers from one or more conditions selected from the group consisting of: atherosclerosis and its associated diseases, premature aging, peripheral vascular insufficiency, and the invention provides for the administration of a metabolite of a SARM compound or composition comprising the same, as herein described, which in some embodiments positively affects a lipid profile in the subject, which is one means by which the method is useful in treating the indicated diseases, disorders and conditions.

In one embodiment, the invention provides a method of treating, preventing, reducing the risk of mortality from cardiovascular and/or cerebrovascular disease in a subject, comprising administering a compound of formula (I-IV) metabolite/s as herein described or its prodrug, ester, analog, isomer, derivative, pharmaceutically acceptable salt, pharmaceutical product, polymorph, crystal, impurity, N-oxide, hydrate or any combination thereof, or a pharmaceutical composition comprising the same. In another embodiment, the metabolite is the glucuronide metabolite of the SARM compound of formula I-IV. In another embodiment, the metabolite is the glucuronide metabolite of compound of formula I. In another embodiment, the metabolite is the glucuronide metabolite of the compound of formula II.

In one embodiment, compounds of formulae I-IV reduce LDL and total cholesterol levels. In one embodiment, compound of formulae I reduce LDL and total cholesterol levels. In another embodiment, compound of formulae II reduce LDL and total cholesterol levels. In another embodiment, the metabolites of this invention of SARM compounds of formula I-IV reduce LDL and total cholesterol levels in a subject. In another embodiment, the glucuronide metabolite of the SARM compound of formula I-IV reduces LDL and total cholesterol levels in a subject. In another embodiment, the glucuronide metabolite of compound of formula I reduces LDL and total cholesterol levels in a subject. In another embodiment, the glucuronide metabolite of compound of formula II reduces LDL and total cholesterol levels in a subject.

In another embodiment, compounds of formulae I-IV and/or a metabolite as herein described are co-administered with HDL-elevating agents. In another embodiment, a compound of formula I is co-administered with an HDL-elevating agents. In another embodiment, a compound of formula II is co-administered with an HDL-elevating agents. In another embodiment, the metabolites of this invention of compounds of formulae I-IV are co-administered with HDL-elevating agents. In another embodiment, a glucuronide metabolite of compound of formula I-IV is co-administered with an HDL-elevating agents. In another embodiment, a glucuronide metabolite of compound of formula I is co-administered with an HDL-elevating agents. In another embodiment, a glucuronide metabolite of compound of formula II is co-administered with an HDL-elevating agents. In another embodiment the HDL-elevating agents include fibrates, niacin, statins, 1-hydroxyalkyl-3-phenylthiourea, and analogs thereof.

In one embodiment, this invention provides a method of treating atherosclerosis and its associated diseases, such as, for example, cardiovascular disorders, cerebrovascular disorders, peripheral vascular disorders, or intestinal vascular disorders in a subject, the method comprising the step of administering to the subject a metabolite of a selective androgen receptor modulator (SARM) compound of formula I-IV as herein described or its pharmaceutically acceptable salt, hydrate, N-oxide, metabolite or any combination thereof, or a composition comprising the same. In another embodiment, the metabolites of this invention of compounds of formulae I-IV treat atherosclerosis and its associated diseases.

In one embodiment, this invention provides a method of improving the dexterity and movement in a subject, for example, by treating arthritis in the subject.

The term "arthritis" refers, in another embodiment, to a non-inflammatory degenerative joint disease occurring chiefly in older people, characterized by degeneration of the articular cartilage, hypertrophy of bones and the margins, changes in the synovial membrane, etc. It is accompanied, in other embodiments, by pain and stiffness, particularly after prolonged activity.

The term "diabetes", in one embodiment, refers to a relative or absolute lack of insulin leading to uncontrolled carbohydrate metabolism. Most patients can be clinically classified as having either insulin-dependent diabetes mellitus (IDDM or Type-I diabetes) or non-insulin-dependent diabetes mellitus (NIDDM or Type-II diabetes).

The term "increased blood pressure" or "hypertension" refers, in other embodiments, to a repeatedly high blood pressure above 140 over 90 mmHg. Chronically-elevated blood pressure can cause blood vessel changes in the back of the eye, thickening of the heart muscle, kidney failure, and brain damage.

The term "stroke" refers, in other embodiments, to damage to nerve cells in the brain due to insufficient blood supply often caused by a bursting blood vessel or a blood clot. The term "heart disease", in other embodiments, refers to a malfunction in the heart normal function and activity, including heart failure.

In addition, androgens have recently been shown to be involved in commitment of mesenchymal pluripotent cells into myogenic lineage and to block differentiation into adipogenic lineage (Singh et al., Endocrinology, 2003, Jul. 24). Accordingly, SARM compounds metabolites as herein described can be useful in methods of blocking adipogenesis, and/or altering stem cell differentiation, as described herein.

In another embodiment, this invention relates to a method of decreasing, suppressing, inhibiting or reducing adipogenesis in a subject, comprising the step of administering to the subject a SARM metabolite/s as herein described and/or its analog, derivative, isomer, pharmaceutically acceptable salt, pharmaceutical product, hydrate, N-oxide, prodrug, polymorph, crystal, or any combination thereof.

In one embodiment, the SARM metabolite/s as herein described are useful in a) treating, preventing, suppressing, inhibiting, or reducing obesity; b) promoting, increasing or facilitating weight loss; c) decreasing, suppressing, inhibiting or reducing appetite; d) altering the body composition; e) altering lean body mass or fat free body mass; f) converting fat to lean muscle; g) treating, preventing, suppressing, inhibiting, or reducing an obesity-associated metabolic disorder, for example hypertension, osteoarthritis, diabetes mellitus, maturity onset diabetes of the young (MODY), increased blood pressure, stroke, or heart disease; h) decreasing, suppressing, inhibiting or reducing adipogenesis; i) altering stem cell differentiation; and/or j) altering the level of leptin.

In one embodiment, the SARMs metabolite/s as herein described find utility in treating or halting the progression of, or treating symptoms of diabetes. In another embodiment, the SARMs as herein described are useful in treating co-morbidities related to diabetes. These conditions include: hypertension, cerebrovascular disease, atherosclerotic coronary artery disease, macular degeneration, diabetic retinopathy (eye disease) and blindness, cataracts—systemic inflammation (characterized by elevation of inflammatory markers such as erythrocyte sedimentation rate or C-reactive protein), birth defects, pregnancy related diabetes, pre-eclampsia and hypertension in pregnancy, kidney disease (renal insufficiency, renal failure etc.), nerve disease (diabetic neuropathy), superficial and systemic fungal infections, congestive heart failure, gout/hyperuricemia, obesity, hypertriglyceridemia, hypercholesterolemia, fatty liver disease (non-alcoholic steatohepatitis, or NASH), and diabetes-related skin diseases such as Necrobiosis Lipoidica Diabeticorum (NLD), Blisters of diabetes (Bullosis Diabeticorum), Eruptive Xanthomatosis, Digital Sclerosis, Disseminated Granuloma Annulare, and Acanthosis Nigricans.

In one embodiment this invention provides a method of treating, suppressing, inhibiting or reducing the incidence of (a) diabetes type I; (b) diabetes type II; (c) glucose intolerance; (d) hyperinsulinemia; (e) insulin resistance (f) nephropathy; (g) diabetic neuropathy; (h) diabetic retinopathy (i) fatty liver conditions (j) MODY and (k) cardiovascular disease in a human subject, comprising the step of administering to said subject a metabolite of a selective androgen receptor modulator compound of formula I-IV as herein described.

In one embodiment, this invention provides a method of treating diabetes type II. Most individuals with type II diabetes exhibit intra abdominal (visceral) obesity, fatty liver, which is closely related to the presence of insulin resistance, with accompanying uncontrolled glycogen breakdown, uncontrolled liver generated cholesterol and VLDL particles with dyslipidemia (high triglyceride and low HDL-cholesterol levels; postprandial hyperlipemia), hypertension, and elevated PAI-1 levels. This clustering of abnormalities is referred to as the "insulin resistance syndrome", or the "metabolic syndrome" or obesity related disorders.

In one embodiment, this invention provides a method of treating diabetic nephropathy, with or with out associated micralbuninuria.

In one embodiment, this invention provides a method of treating diabetic neuropathy.

In one embodiment, this invention provides a method of treating diabetic retinopathy. The effect of diabetes on the eye is called diabetic retinopathy. Patients with diabetes are more likely to develop eye problems such as cataracts and glaucoma. The affect of diabetic retinopathy on vision varies widely, depending on the stage of the disease. Some common symptoms of diabetic retinopathy are blurred vision (this is often linked to blood sugar levels), floaters and flashes and sudden loss of vision.

In one embodiment, the subject for whom treatment is sought via the methods of this invention is one with glucose intolerance. Glucose intolerance is a pre-diabetic state in which the blood glucose is higher than normal but not high enough to warrant the diagnosis of diabetes.

In one embodiment, the subject for whom treatment is sought via the methods of this invention is one with hyperinsulinemia. Hyperinsulinemia is a sign of an underlying problem that is causing the pancreas to secrete excessive amounts of insulin.

In one embodiment, the subject for whom treatment is sought via the methods of this invention is one with insulin resistance. Insulin resistance is a condition in which normal amounts of insulin are inadequate to produce a normal insulin response from fat, muscle and liver cells.

Diabetes and the liver obesity is typically associated with elevated levels of free fatty acid (FFAs) that promote lipid accumulation and insulin resistance in target tissues, i.e. reduced action of insulin primarily in skeletal muscle and liver.

In one embodiment, this invention provides methods that inhibit (improve) the fatty liver, resulting in that the insulin resistance in the liver is inhibited (improved) and thereby solving the basic problem in type II diabetes.

In one embodiment, this invention provides a method of treating suppressing, inhibiting or reducing the incidence of diabetes is a human subject, comprising the step of administering to said subject a metabolite of selective androgen receptor modulator (SARM) compound of formulas I-IV, or its isomer, pharmaceutically acceptable salt, pharmaceutical product, hydrate, N-oxide, or any combination thereof.

In another embodiment, the diabetes is a Type I diabetes. In another embodiment, the diabetes is a type II diabetes.

In one embodiment, this invention provides a method of treating a human subject having glucose intolerance, comprising the step of administering to said subject a metabolite of selective androgen receptor modulator (SARM) compound of formulas I-IV or its isomer, pharmaceutically acceptable salt, pharmaceutical product, hydrate, N-oxide, or any combination thereof.

In one embodiment, this invention provides a method of treating a hyperinsulinemia in a human subject, comprising the step of administering to said subject a metabolite of selective androgen receptor modulator compound of formulas I-IV or its isomer, pharmaceutically acceptable salt, pharmaceutical product, hydrate, N-oxide, or any combination thereof.

In one embodiment, this invention provides a method of treating insulin resistance in a human subject, comprising the step of administering to said subject a metabolite of the selective androgen receptor modulator compound of formulas I-IV or its isomer, pharmaceutically acceptable salt, pharmaceutical product, hydrate, N-oxide, or any combination thereof.

In one embodiment, this invention provides a method of treating diabetic nephropathy in a human subject, comprising the step of administering to said subject a metabolite of the selective androgen receptor modulator compound of formulas I-IV or its isomer, pharmaceutically acceptable salt, pharmaceutical product, hydrate, N-oxide, or any combination thereof.

In one embodiment, this invention provides a method of treating diabetic neuropathy in a human subject, comprising the step of administering to said subject a metabolite of selective androgen receptor modulator compound of formulas I-IV or its isomer, pharmaceutically acceptable salt, pharmaceutical product, hydrate, N-oxide, or any combination thereof.

In one embodiment, this invention provides a method of treating diabetic retinopathy in a human subject, comprising the step of administering to said subject a metabolite of selective androgen receptor modulator compound of formulas I-IV or its isomer, pharmaceutically acceptable salt, pharmaceutical product, hydrate, N-oxide, or any combination thereof.

In one embodiment, this invention provides a method of treating fatty liver conditions in a human subject, comprising the step of administering to said subject a metabolite of selective androgen receptor modulator compound of formulas I-IV or its isomer, pharmaceutically acceptable salt, pharmaceutical product, hydrate, N-oxide, or any combination thereof.

In one embodiment, this invention provides a method of treating cardiovascular disease in a human subject, comprising the step of administering to said subject a metabolite of selective androgen receptor modulator compound of formulas I-IV or its isomer, pharmaceutically acceptable salt, pharmaceutical product, hydrate, N-oxide, or any combination thereof.

Thus, in one embodiment, the methods of the present invention comprise administering the SARM compound metabolite/s as herein described, in combination with diabetes drug such as troglitazone, rosiglitazone, and pioglitazone. In another embodiment, the methods of the present invention comprise administering a SARM compound metabolite/s as herein described in combination with an LHRH analog, a reversible antiandrogen, an antiestrogen, selective estrogen receptor modulators (SERM), a 5-alpha reductase inhibitor, an aromatase inhibitor, a progestin, a progesterone, an estrogen, an agent acting through other nuclear hormone receptors, a PDE5 inhibitor, apomorphine or combinations thereof.

Pharmaceutical Composition

In some embodiments, this invention provides methods of use which comprise administering a composition comprising the described compounds. As used herein, "pharmaceutical composition" means a "therapeutically effective amount" of the active ingredient, i.e. the metabolite of the SARM compound, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a metabolite of a SARM compound of the present invention. As used herein, administration can be accomplished in vitro, i.e. in a test tube, or in vivo, i.e. in cells or tissues of living organisms, for example humans. In one embodiment, the present invention encompasses administering the metabolites of the compounds of the present invention to a subject.

The pharmaceutical compositions containing the metabolite of a SARM agent can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the metabolites of the SARM compounds are formulated in a capsule. In accordance with this embodiment, the compositions of the present invention comprise in addition to the metabolite active compound and the inert carrier or diluent, a hard gelatin capsule.

In one embodiment, the micronized capsules comprise particles containing a metabolite of this invention, wherein the term "micronized" used herein refers to particles having a particle size is of less than about 100 microns, or in another embodiment, less than about 50 microns, or in another embodiment, less than about 35 microns, or in another embodiment, less than about 15 microns, or in another embodiment, less than about 10 microns, or in another embodiment, less than about 5 microns.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the metabolite agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of metabolite of a SARM agent over a period of time. In a further embodiment, the pharmaceutical compositions are administered intravaginally.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formuations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In one embodiment, the compositions of this invention may include, a metabolite of a SARM of this invention or any combination thereof, together with one or more pharmaceutically acceptable excipients.

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sobitan esters, stearic acids), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), coloring agents, lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the metabolite compound is released over a period of time after administration. Controlled or sustained release compositions include formulation in lipophilic depots (e.g. fatty acids, waxes, oils). In another embodiment, the composition is an immediate release composition, i.e. a composition in which all of the metabolite of the compound is released immediately after administration.

In another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions, which contain an active component is well understood in the art, for example by mixing, granulating, or tablet-forming processes. The active therapeutic ingredient is often mixed with excipients which are pharmaceutically acceptable and compatible with the active ingredient. For oral administration, the metabolites of SARM agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the metabolites of SARM agents or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the metabolites of compounds of formula I-IV will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

The invention includes "pharmaceutically acceptable salts" of the compounds of this invention, which may be produced, in one embodiment, to form alkali metal salts and to form addition salts of free acids or free bases. Suitable pharmaceutically-acceptable acid addition salts of compounds of Formula I-IV may be prepared from an inorganic acid or from an organic acid. In one embodiment, examples of inorganic acids are hydrochloric, hydrobromic, hydroiodic, nitric, carbonic, sulfuric and phosphoric acid. In one embodiment, organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, oxalic, p-toluenesulphonic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. In one embodiment, suitable pharmaceutically-acceptable base addition salts of compounds of Formula I-IV include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compounds.

Pharmaceutically acceptable salts can be prepared, from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters.

In one embodiment, this invention provides pharmaceutical compositions comprising a metabolite of compound I-IV of this invention. In one embodiment, such compositions are useful for oral testosterone replacement therapy.

In one embodiment, this invention also provides a composition comprising two or more metabolites of compounds of I-IV of this invention, or polymorphs, isomers, hydrates, salts, N-oxides, etc., thereof. The present invention also relates to compositions and a pharmaceutical composition, which comprises a metabolite alone or in combination with a progestin or estrogen, or in another embodiment, chemotherapeutic compound, osteogenic or myogenic compound, or other agents suitable for the applications as herein described. In one embodiment, the compositions of this invention will comprise a suitable carrier, diluent or salt.

In one embodiment, the methods of this invention may comprise administration of a metabolite of compound of formula I-IV of this invention at various dosages. In one embodiment, the metabolite of compound of formula I-IV is administered at a dosage of about 0.01-1 mg per day. In one embodiment, metabolite of compound of formula I-IV is administered at a dosage of about 0.1-200 mg per day. In one embodiment, metabolite of compound of formula I-IV is administered at a dose of about 0.1-10 mg per day, or in another embodiment about 0.1-25 mg per day, or in another embodiment about 0.1-50 mg per day, or in another embodiment about 0.3-15 mg per day, or in another embodiment about 0.3-30 mg per day, or in another embodiment about 0.5-25 mg per day, or in another embodiment about 0.5-50 mg per day, or in another embodiment about 0.75-15 mg per day, or in another embodiment about 0.75-60 mg per day, or in another embodiment about 1-5 mg per day, or in another embodiment about 1-20 mg per day, or in another embodiment about 3-15 mg per day, or in another embodimentabout 30-50 mg, or in another embodiment about 30-75 mg per day, or in another embodiment about 100-2000 mg per day.

In one embodiment, the methods of this invention may comprise administration of a metabolite of compound of formula I at various dosages. In one embodiment, metabolite of compound of formula I is administered at a dosage of 1 mg. In another embodiment the metabolite of compound of formula I is administered at a dosage of 0.01 mg, 0.03 mg, 0.1 mg, 0.3 mg, 0.75 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg.

In one embodiment, the metabolite of compound of formulas I-IV of this invention may be administered at various dosages. In one embodiment, metabolite of compound of formula I is administered at a dosage of 0.01-1 mg per day. In one embodiment, metabolite of compound of formula I is administered at a dosage of 0.1-200 mg per day. In one embodiment, metabolite of compound of formula I is administered at a dose of 0.1-10 mg per day, or in another embodiment, 0.1-25 mg per day, or in another embodiment, 0.1-50 mg per day, or in another embodiment, 0.3-15 mg per day, or in another embodiment, 0.3-30 mg per day, or in another embodiment, 0.5-25 mg per day, or in another embodiment, 0.5-50 mg per day, or in another embodiment, 0.75-15 mg per day, or in another embodiment, 0.75-60 mg per day, or in another embodiment, 1-5 mg per day, or in another embodiment, 1-20 mg per day, or in another embodiment, 3-15 mg per day, or in another embodiment, 30-50 mg, or in another embodiment, 30-75 mg per day, or in another embodiment, 100-2000 mg per day.

In one embodiment, the present invention provides methods of use comprising the administration of a pharmaceutical composition comprising a) any embodiment of a metabolite compound as described herein; and b) a pharmaceutically acceptable carrier or diluent; which is to be understood to include an analog, isomer, metabolite, derivative, pharmaceutically acceptable salt, N-oxide, hydrate or any combination thereof of a compound as herein described, and may comprise metabolites of compounds of formulas I-IV.

In some embodiments, the term "comprise" or grammatical forms thereof, refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components, which exert a therapeutic effect via a mechanism distinct from that of the indicated active ingredient. In some embodiments, the term "consisting essentially of" may refer to components, which exert a therapeutic effect and belong to a class of compounds distinct from that of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In some embodiments, the present invention provides methods of use of a pharmaceutical composition comprising a) any embodiment of the compounds as described herein, including an analog, isomer, metabolite, derivative, pharmaceutically acceptable salt, pharmaceutical product, N-oxide, hydrate thereof or any combination thereof; b) a pharmaceutically acceptable carrier or diluent; c) a flow-aid; and d) a lubricant.

In another embodiment, the present invention provides methods of use of a pharmaceutical composition comprising a) any embodiment of the compounds as described herein, including an analog, isomer, metabolite, derivative, pharmaceutically acceptable salt, pharmaceutical product, N-oxide, hydrate thereof or any combination thereof; b) lactose monohydrate; c) microcrystalline cellulose; d) magnesium stearate; and e) colloidal silicon dioxide.

In some embodiments, the methods of this invention make use of compositions comprising metabolites of SARM compounds, which offer the advantage that the compounds are nonsteroidal ligands for the androgen receptor, and exhibit anabolic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides metabolites of compounds and compositions, including any embodiment described herein, for use in any of the methods of this invention. In one embodiment, use of a metabolite SARM or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the metabolite SARM compound is being administered.

In some embodiments, the compositions will further comprise a 5a-Reductase Inhibitors, another SARM, a SERM, an aromatase inhibitor, such as but not limited to anastrozole, exemestane, or letrozole; a GnRH agonist or antagonist, a steroidal or nonsteroidal GR ligand, a steroidal or nonsterodial PR ligand, a steroidal or nonsteroidal AR antagonist, a 17-aldoketoreductase inhibitor or 17β-hydroxysteroid dehydrogenase inhibitor. Such compositions may be used, in some embodiments, for treating a hormone dependent condition, such as, for example, infertility, neoplasia of a hormone-responsive cancer, for example, a gonadal cancer, or a urogenital cancer.

In some embodiments, the composition will comprise the metabolites of SARMs as described herein, as well as another therapeutic compound, including inter alia, a 5ARI such as finasteride, dutasteride; SERMs, such as tamoxifene, 4-hydroxytamoxifene, idoxifene, toremifene, ospemifene, droloxifene, raloxifene, GnRH agonists or antagonists, such as, leuprolide, goserelin, triptorelin, alfaprostol, histrelin, detirelix, ganirelix, antide iturelix; LH agonist/antagonists, aromatase inhibitors, such as, letrozole, anastrazole, atamestane, fadrozole; Steroidal or nonsteroidal glucocorticoid receptor ligands, such as, ZK-216348, ZK-243149, ZK-243185, LGD-5552, mifepristone, RPR-106541, ORG-34517, GW-215864X; Steroidal or nonsterodial progesterone receptor ligands; Steroidal or nonsteroidal AR antagonists such as flutamide, hydroxyflutamide, bicalutamide, PPARα ligand such as bezafibrate, fenofibrate, gemfibrozil; PPARγ ligands such as darglitazone, pioglitazone, rosiglitazone; Dual acting PPAR ligands, such as naveglitazar, farglitazar; 17-ketoreductase inhibitors, 3'-DHΔ4,6-isomerase inhibitors, 3β-DHΔ4,5-isomerase inhibitors, 17,20 desmolase inhibitors, p450c17 inhibitors, p450ssc inhibitors, 17,20-lyase inhibitors, or combinations thereof.

In some embodiments, the compositions will further comprise Ghrelin receptor ligand or growth hormone analogues and secretagogues, IGF-1, IGF-1 analogues and secretagogues, myostatin analogues, proteasome inhibitors, androgenic/anabolic steroid, Enbrel, melanocortin 4 receptor agonist, insulins, or combinations thereof. Such compositions may be used, in some embodiments, for treating sarcopenia or a musculoskeletal condition.

In some embodiments, the composition will comprise the metabolite of SARMs as described herein, as well as another therapeutic compound, including inter alia, ghrelin receptor ligand or growth hormone analogues and secretagogues, an androgenic/anabolic steroid such as testosterone/oxandrolone; a melanocortin 4 receptor agonist, such as bremelanotide, a ghrelin or analogue thereof, such as human ghrelin, leptin (metreleptin, pegylated leptin; a leptin receptor agonist, such as LEP (116-130), OB3, [D-Leu4]-OB3, rAAV-leptin, AAV-hOB, rAAVhOB; an insulin; a cortisol or corticosteroid, or a combination thereof.

The invention contemplates, in some embodiments, administration of compositions comprising the individual agents, administered separately and by similar or alternative routes, formulated as appropriately for the route of administration. The invention contemplates, in some embodiments, administration of compositions comprising the individual agents, administered in the same formulation. The invention contemplates, in some embodiments, staggered administration, concurrent administration, of administration of the various agents over a course of time; however, their effects are synergistic in the subject.

It is to be understood that any of the above means, timings, routes, or combinations thereof, of administration of two or more agents is to be considered as being encompassed by the phrase "administered in combination", as described herein.

In one embodiment, the metabolite of the SARM compound is administered in combination with an anti-cancer agent. In one embodiment, the anti-cancer agent is a monoclonal antibody. In some embodiments, the monoclonal antibodies are used for diagnosis, monitoring, or treatment of cancer. In one embodiment, monoclonal antibodies react against specific antigens on cancer cells. In one embodiment, the monoclonal antibody acts as a cancer cell receptor antagonist. In one embodiment, monoclonal antibodies enhance the patient's immune response. In one embodiment, monoclonal antibodies act against cell growth factors, thus blocking cancer cell growth. In one embodiment, anti-cancer monoclonal antibodies are conjugated or linked to anti-cancer drugs, radioisotopes, other biologic response modifiers, other toxins, or a combination thereof. In one embodiment, anti-cancer monoclonal antibodies are conjugated or linked to a metabolite of a SARM compound as described hereinabove.

In another embodiment, the present invention includes metabolites of SARM compounds and compositions in which a compound of the invention is either combined with, or covalently bound to, an agent bound or to a targeting agent. The compounds of the invention may also be combined with monoclonal antibodies that have therapeutic activity against cancer.

In one embodiment, the metabolite of the SARM compound is administered in combination with a selective tyrosine kinase inhibitor. In some embodiments, the selective tyrosine kinase inhibitor inhibits catalytic sites of cancer promoting receptors thereby inhibiting tumor growth. In one embodiment, a selective tyrosine kinase inhibitor modulates growth factor signaling. In one embodiment, the selective tyrosine kinase inhibitor is a vascular endothelial growth factor tyrosine kinase inhibitor. In one embodiment, the selective tyrosine kinase inhibitor is a Platelet Derived Growth Factor (PDGF) inhibitor.

In one embodiment, the metabolite of the SARM compound is administered in combination with a cancer vaccine. In one embodiment, the cancer vaccine is a therapeutic vaccine thus, treating an existing cancer. In some embodiments, the cancer vaccine is a prophylactic vaccine thus, preventing the development of cancer. In one embodiment, the cancer vaccine is an antigen/adjuvant vaccine. In one embodiment, the cancer vaccine is a whole cell tumor vaccine. In one embodiment, the cancer vaccine is a dendritic cell vaccine. In one embodiment, the cancer vaccine comprises viral vectors and/or DNA vaccines. In one embodiment, the cancer vaccine is an idiotype vaccine.

In one embodiment, the metabolite of the SARM compound is administered in combination with an anti-cancer chemotherapeutic agent. In one embodiment, the anti-cancer chemotherapeutic agent is an alkylating agent, such as but not limited to cyclophosphamide. In one embodiment, the anti-cancer chemotherapeutic agent is a cytotoxic antibiotic such as but not limited to doxorubicin. In one embodiment, the anti-cancer chemotherapeutic agent is an antimetabolite, such as but not limited to methotrexate. In one embodiment, the anti-cancer chemotherapeutic agent is a vinca alkaloid, such as but not limited to vindesine. In some embodiments, the anti-cancer chemotherapeutic agents include platinum compounds such as but not limited to carboplatin, and taxanes such as docetaxel. In one embodiment, the anti-cancer chemotherapeutic agent is an aromatase inhibitor such as but not limited to anastrazole, exemestane, or letrozole.

In one embodiment, the metabolite of the SARM compound is administered in combination with a Bax activity modulator such as alisol B acetate. In one embodiment, the metabolite of the SARM compound is administered in combination with an angiotensin II receptor blocker such as losartan. In one embodiment, the metabolite of the SARM compound is administered in combination with selenium, green tea cachecins, saw palmetto, lycopene, vitamin D, dietary soy, genistein or isoflavone.

In one embodiment, the metabolite of the SARM compound is administered in combination with antineoplastic agents, such as alkylating agents, antibiotics, hormonal antineoplastics and antimetabolites. More such agents will be known to those having skill in the medicinal chemistry and oncology arts.

In some embodiments, other agents suitable for combination with metabolite/s of SARMs include protein synthesis inhibitors such as abrin, aurintricarboxylic acid, chloramphenicol, neomycin and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine; and RNA synthesis inhibitors including actinomycin D, α-amanitine and other fungal amatoxins, cordycepin (3'-deoxyadenosine), dichlororibofuranosyl benzimidazole, rifampicin, streptovaricin and streptolydigin also can be combined with the metabolite of the compounds of the invention to provide pharmaceutical compositions.

In one embodiment, the metabolite/s of the SARM compound is administered in combination with a vaccine for prostate cancer, Alisol B acetate, angiotensin II receptor blocker, or others known in the art. In one embodiment, the metabolite/s of the SARM compound is administered in combination with an agent to decrease prostate (benign or malignant) hypertrophy, such as, for example, Selenium, green tea cachecins, saw palmetto, lycopene, vitamin D, dietary soy, genistein and isoflavone food product and others.

In one embodiment, the metabolite/s of the SARM compound is administered in combination with an immunomodulating agent. In one embodiment, the immunomodulating agent is an immunosuppressive agent. In one embodiment, immunosuppressive agents comprise corticosteroids, cyclosporine, azathioprine, methotrexate, cyclophosphamide, tacrolimus-FK-506, anti-thymocyte globulin, mycophenylate moeftil, or a combination thereof. In one embodiment, the corticosteroid is a glucocorticoid.

In one embodiment, the immunomodulating agent is an immunostimulatory agent. In one embodiment, the immunostimulatory agent is a specific immunostimulator thus, provides antigenic specificity during an immune response, such as a vaccine or any antigen. In one embodiment, the immunostimulatory agent is a non-specific immunostimulator thus, acting irrespective of antigenic specificity to augment immune response of other antigen or stimulate components of the immune system without antigenic specificity. In one embodiment, the non-specific immunostimulator is Freund's complete adjuvant. In one embodiment, the non-specific immunostimulator is Freund's incomplete adjuvant. In one embodiment, the non-specific immunostimulator is a montanide ISA adjuvant. In one embodiment, the non-specific immunostimulator is a Ribi's adjuvant. In one embodiment, the non-specific immunostimulator is a Hunter's TiterMax. In one embodiment, the non-specific immunostimulator is an aluminum salt adjuvant. In one embodiment, the non-specific immunostimulator is a nitrocellulose-adsorbed protein. In one embodiment, the non-specific immunostimulator is a Gerbu Adjuvant.

The invention relates, inter alia to treatment of an SRE with the metabolite of compound of formula I in a subject with prostate cancer undergoing or having undergone androgen deprivation therapy (ADT).

In another embodiment, the methods and/or compositions provided herein, are effective in treatment, prevention, suppression, inhibition or reduction of the risk of skeletal-related events such as pathologic fractures, spinal cord compression, hypercalcemia, bone-related pain, or their combination.

In another embodiment, the skeletal-related events sought to be treated using the methods provided herein and/or utilizing the compositions provided herein, comprise the necessity for bone surgery and/or bone radiation, which in some embodiments, is for the treatment of pain resulting in one embodiment from bone damage, or nerve compression In one embodiment, the methods provided herein and/or utilizing the compositions provided herein, are effective in reducing metastases to the bone, such as in terms of number of foci, the size of foci, or a combination thereof. According to this aspect of the invention and in one embodiment, provided herein is a method of preventing or inhibiting cancer metastasis to bone in a subject, comprising the step of administering to the subject a composition comprising toremifene, raloxifene, tamoxifen or an analogue, functional derivative, metabolite or a combination thereof, or a pharmaceutically acceptable salt thereof. In one embodiment, such metabolites may comprise ospemifene, fispemifene or their combination. In one embodiment, the cancer is prostate cancer.

A person skilled in the art would readily recognize that changes in the antineoplastic therapy according to the methods provided herein, utilizing the compositions provided herein may be conducted as a function of, or adjusted or varied as a function of, inter alia, the severity of the underlying disease, the source of the underlying disease, the extent of the patients' pain and source of the patients' pain, as well as the stage of the disease.

In males, while the natural decline in sex-hormones at maturity (direct decline in androgens as well as lower levels of estrogens derived from peripheral aromatization of androgens) is associated with the frailty of bones, this effect is more pronounced in males who have undergone androgen deprivation therapy.

Such agents for combined use may comprise a SERM, as herein described, a bisphosphonate, for example, alendronate, pamidronate, etidronate, alendronate, zolendronate, ibandronate; a calcitonin, for example, salmon, a vitamin D or derivative (ZK-156979); a vitamin D receptor ligand or analogues thereof, such as calcitriol, topitriol, an estrogen, estrogen derivative, or conjugated estrogen; an antiestrogen, progestin, synthetic estrogen/progestin; a RANK ligand mAb, for example; an $\alpha v \beta 3$ integrin receptor antagonist; an osteoclast vacuolar ATPase inhibitor; an antagonist of VEGF binding to osteoclast receptors; a calcium receptor antagonist; PTh (parathyroid hormone) or analogues thereof, PTHrP analogues (parathyroid hormone-related peptide), cathepsin K inhibitors (AAE581); strontium ranelate; tibolone; HCT-1026, PSK3471; gallium maltolate; Nutropin AQ; prostaglandins, p38 protein kinase inhibitor; a bone morphogenetic protein; an inhibitor of BMP antagonism, an HMG-CoA reductase inhibitor, a vitamin K or derivative, an antiresorptive, an ipriflavone, a fluoride salt, dietary calcium supplement, osteoprotegerin, or any combination thereof. In one embodiment, the combined administration of a SARM and/or metabolite as herein described, osteoprotegerin and parathyroid hormone is contemplated for treating any disease, disorder or condition of the bone.

In one embodiment, the immunomodulating agent is an anti-inflammatory agent. In one embodiment, the anti-inflammatory agent is a non-steroidal anti-inflammatory agent. In one embodiment, the non-steroidal anti-inflammatory agent is a cox-1 inhibitor. In one embodiment, the non-steroidal anti-inflammatory agent is a cox-2 inhibitor. In one embodiment, the non-steroidal anti-inflammatory agent is a cox-1 and cox-2 inhibitor. In some embodiments, non-steroidal anti-inflammatory agents include but are not limited to aspirin, salsalate, diflunisal, ibuprofen, fenoprofen, flubiprofen, fenamate, ketoprofen, or celecoxib. In one embodiment, the anti-inflammatory agent is a steroidal anti-inflammatory agent. In one embodiment, the steroidal anti-inflammatory agent is a corticosteroid.

In one embodiment, the immunomodulating agent is an anti-rheumatic agent. In one embodiment, the anti-rheumatic agent is a non-steroidal anti-inflammatory agent. In one embodiment, the anti-rheumatic agent is a corticosteroid. In one embodiment, the corticosteroid is prednisone or dexamethasone. In one embodiment, the anti-rheumatic agent is a disease modifying anti-rheumatic drug. In one embodiment, the disease modifying anti-rheumatic drug is a slow-acting anti-rheumatic drug. In one embodiment, the disease modifying anti-rheumatic drug is an antimalarial agent. In one embodiment, disease modifying anti-rheumatic drugs include but are not limited to chloroquine, hydroxychloroquine, methotrexate, sulfasalazine, cyclosporine, azathioprine, cyclophosphamide, azathioprine, sulfasalazine, penicillamine, aurothioglucose, gold sodium thiomalate, or auranofin or combinations thereof. In one embodiment, the anti-rheumatic agent is an immunosuppressive cytotoxic drug. In one embodiment, immunosuppressive cytotoxic drugs include but are not limited to methotrexate, mechlorethamine, cyclophosphamide, chlorambucil, or azathioprine.

In one embodiment, the metabolite of the SARM compound is administered in combination with an antidiabetic agent. In one embodiment, the antidiabetic agent is a sulfonylurea. In one embodiment, the antidiabetic agent is a meglitinide. In one embodiment, meglitinides include but are not limited to prandin or nateglinide. In one embodiment, the antidiabetic agent is a biguanide. In one embodiment, biguanides include but are not limited to metformin. In one embodiment, the antidiabetic agent is a thiazolidinedione. In one embodiment, thiazolidinediones include but are not limited to rosiglitazone, pioglitazone, or troglitazone. In one embodiment, the antidiabetic agent is an alpha glucosidase inhibitor. In one embodiment, alpha glucosidase inhibitors include but are not limited to miglitol or acarbose. In one embodiment, the antidiabetic agent is PPAR$\alpha$/$\gamma$ ligand, dipeptidylpeptidase 4 (DPP-4) inhibitor, SGLT (sodium-dependent glucose transporter 1) inhibitor, or FBPase (fructose 1,6-bisphosphatase) inhibitor. In one embodiment, the antidiabetic agent is insulin. In one embodiment, the insulin is rapid-acting insulin. In one embodiment, the insulin is short-acting insulin. In one embodiment, the insulin is intermediate-acting insulin. In one embodiment, the insulin is intermediate- and short-acting insulin mixtures. In one embodiment, the insulin is long-acting insulin. In one embodiment, the antidiabetic agents are inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DPP4) inhibitors such as those disclosed in WO 0168603, which are incorporated by reference.

In one embodiment, the metabolite of the SARM compound is administered in combination with an agent treating the nervous system. In one embodiment, the agent treating the nervous system is an agent treating the autonomic nervous system. In one embodiment, the agent treating the autonomic nervous system is an adrenomimetic drug. In one embodiment, the adrenomimetic drug is a beta-adrenoceptor agonist, alpha-adrenoceptor agonist, or a combination thereof. In one embodiment, the adrenomimetic drug is a catecholamine. In one embodiment, adrenomimetic drugs include but are not limited to isoproterenol, norepinephrine, epinephrine, amphetamine, ephedrine, or dopamine. In one embodiment, the adrenomimetic drug is a directly acting adrenomimetic drug. In some embodiments, directly acting adrenomimetic drugs include but are not limited to phenylephrine, metaraminol, or methoxamine.

In one embodiment, the agent treating the autonomic nervous system is an adrenoceptor antagonist. In one embodiment, the adrenoceptor antagonist is a haloalkylamine, imidazoline, or quinazoline. In one embodiment, haloalkylamines include but are not limited to phenoxybenzamine. In one embodiment, imidazolines include but are not limited to phentolamine or tolazoline. In one embodiment, quinazolines include but are not limited to prazosine, terazosin, doxazosin, or trimazosin. In one embodiment, the adrenoceptor antagonist has a combined alpha and beta blocking activity. In one embodiment, the combined alpha and beta blocking agent is labetalol, bucindolol, carvedilol, or medroxalol.

In one embodiment, the agent treating the autonomic nervous system is a cholinomimetic agent. In one embodiment, the cholinomimetic agent is a direct-acting parasympathomimetic drug.

In one embodiment, direct-acting parasympathomimetic drugs include but are not limited to methacholine, pilocarpine, carbachol, or bethanechol.

In one embodiment, the agent treating the autonomic nervous system is a cholinesterase inhibitor. In one embodiment, the cholinesterase inhibitor is a quaternary ammonium agent. In one embodiment, quaternary ammonium agents include but are not limited to edrophonium or ambenonium. In one embodiment, the cholinesterase inhibitor is a carbamate such as physostigmine, pyridostigmine, neostigmine, or rivastigmine. In one embodiment, the cholinesterase inhibitor is an organophosphate agent. In one embodiment, the inhibitor targets acetylcholine in the central nervous system such as tacrine, donepezil, or galanthamine.

In one embodiment, the agent treating the autonomic nervous system is a muscarinic blocking agent. In one embodiment, the muscarinic blocking agent is a belladonna alkaloid such as atropine or scopolamine.

In one embodiment, the agent treating the autonomic nervous system is a ganglionic blocking agent. In one embodiment, ganglionic blocking agents include but are not limited to nicotine, trimethaphan, or mecamylamine.

In one embodiment, the agent treating the nervous system is an agent treating the central nervous system. In one embodiment, the agent treating the central nervous system is a local anesthetic agent. In one embodiment, local anesthetic agents include but are not limited to benzocaine, chloroprocaine, cocaine, procaine, bupivacaine, levobupivacaine, lidocaine, mepivacaine, prilocalne, or ropivacaine. In one embodiment, the agent treating the central nervous system is a general anaesthetic agent. In one embodiment, general anesthetic agents include but are not limited to esflurane, sevoflurane, isoflurane, halothane, enflurane, methoxyflurane, xenon, propofol, etomidate, methohexital, midazolam, diazepamor, ketamine, thiopentone/thiopental, or lidocaine/prilocalne.

In one embodiment, the agent treating the central nervous system is an analgesic agent. In some embodiments, analgesic agents include but are not limited to paracetamol or non-steroidal anti-inflammatory agent. In some embodiments, analgesic agents include opiates or morphinomimetics such as morphine, pethidine, oxycodone, hydrocodone, diamorphine, tramadol, or buprenorphine. In some embodiments, a combination of two or more analgesics is desired.

In one embodiment, the agent treating the central nervous system is a muscle relaxant or vasoconstrictor agent. In one embodiment, muscle relaxants include but are not limited to methocarbamol, baclofen, carisoprodol, chlorzoxazone, cyclobenzaprine, dantrolene, metaxalone, orphenadrine, amyl nitrite, pancuronium, tizanidine, clonidine, gabapentin or combinations thereof. In one embodiment, vasoconstrictor agents include but are not limited to antihistamines, adrenalin dimethylarginine, caffeine, cannabis, catecholamines, decongestants, pseudoephedrinse, norepinephrines, tetrahydrozoline, or thromboxane.

In one embodiment, the agent treating the central nervous system is an antiemetic drug. In one embodiment, the antiemetic drug is a 5-HT3 receptor antagonist such as dolasetron, granisetron, ondansetron, or tropisetron. In one embodiment, the antiemetic drug is a dopamine antagonist such as domperidone droperidol, haloperidol, chlorpromazine, promethazine, or metoclopramide. In one embodiment, the antiemetic drug is an antihistamine such as cyclizine, diphenhydramine, dimenhydrinate, or meclizine. In one embodiment, the antiemetic drug is a cannabinoid such as cannabis or marinol.

In one embodiment, the agent treating the central nervous system is a sedative agent. In one embodiment, the sedative agent is an antidepressant agent such as mirtazapine or trazodone. In one embodiment, the sedative agent is a barbiturate such as secobarbital, pentobarbital, or amobarbital. In one embodiment, the sedative agent is a benzodiazepine such as diazepam, clonazepam, alprazolam, temazepam, chlordiazepoxide, flunitrazepam, lorazepam, or clorazepate. In one embodiment, the sedative agent is an imidazopyridines such as zolpidem or alpidem. In one embodiment, the sedative agent is a pyrazolopyrimidine such as zaleplon. In one embodiment, the sedative agent is an antihistamine such as diphenhydramine, dimenhydrinate, or doxylamine. In one embodiment, the sedative agent is an antipsychotic agent such as ziprasidone, risperidone, quetiapine, clozapine, prochlorperazine, perphenazine, loxapine, trifluoperazine, thiothixene, haloperidol, fluphenazine or combinations thereof. In one embodiment, the sedative agent is an herbal sedative such as valerian plant mandrake, or kava. In some embodiments, the sedative agent is eszopiclone, ramelteon, methaqualone, ethchlorvynol, chloral hydrate, meprobamate, glutethimide, methyprylon, gamma-hydroxybutyrate, ethyl alcohol, methyl trichloride, zopiclone, or diethyl ether.

In one embodiment, the agent treating the central nervous system is a neurodegenerative disorder medication. In one embodiment, the neurodegenerative disorder medication is an acetylcholinesterase inhibitor such as tacrine, donepezil, galanthamine, or rivastigmine. In one embodiment, the neurodegenerative disorder medication is an N-methyl-D-aspartate (NMDA) antagonist such as memantine. In one embodiment, the neurodegenerative disorder medication reduces damage to motor neurons such as riluzole. In one embodiment, the neurodegenerative disorder medication silences the gene that causes the progression of the disease. In one embodiment, the agent treating the central nervous system is an antiepileptic drug (AED). In some embodiments, antiepileptic agents include sodium channel blockers, GABA receptor agonists, GABA reuptake inhibitors, GABA transaminase inhibitor, AEDs with a potential GABA mechanism of action, glutamate blockers, or AEDs with other mechanisms of action. In some embodiments, antiepileptic agents include but are not limited to carbamazepine, fosphenyloin, oxcarbazepine, lamotrigine, zonisamide, clobazam, clonazepam, phenobarbital, primidone, tiagabine, vigabatrin, gabapentin, valproate, felbamate, topiramate, levetiracetam, pregabalin or combinations thereof.

In one embodiment, the agent treating the central nervous system is an anti-addiction drug. In one embodiment, the anti-addiction is an anti-alcoholism drug such as disulfiram. In one embodiment, the anti-addiction drug is a serotonin uptake inhibitor, dopaminergic agonist, or opioid antagonist.

In one embodiment, the agent treating the central nervous system is an agent treating Alzheimer disease. In some embodiments, agents treating Alzheimer's disease include but are not limited to a cholinesterase inhibitor, gamma secreatse inhibitor, or a beta lowering drug.

In one embodiment, the agent treating the central nervous system is an agent treating mild cognitive impairment. In some embodiments, agents treating mild cognitive impairment include but are not limited to an AMPA regulator.

In one embodiment, the agent treating the central nervous system is an agent treating Parkinson's disease. In some embodiments, agents treating Parkinson's disease include but are not limited to a dopaminergic drugs, amantadine, benztropine, biperiden, bromocriptine, entacapone, carbidopa/levodopa, selegiline/deprenyl, iphenhydramine, pergolide, procyclidine, selegiline, trihexyphenidyl or combinations thereof.

In one embodiment, the metabolite of the SARM compound is administered with an agent, which treats Alzheimer's disease, such as cholinesterase inhibitors, gamma secreatse inhibitors, A-beta lowering drugs; or an agent, which treats mild cognitive impairment (MCI)—such as AMPA regulators, or an agent, which treats Parkinson's Disease, such as dopaminergic drugs, or an agent, which treats major depression, such as SSRI's, SNRI's, for example, duloxetine, or an agent, which treats sexual dysfunction, such as PDE5 inhibitors.

In one embodiment, the metabolite of the SARM compound is administered in combination with an agent treating the cardiovascular system. In one embodiment, the agent treating the cardiovascular system is treating a congestive heart failure. In one embodiment, the agent treating congestive heart failure is an angiotensin converting enzyme (ACE) inhibitor, with or without a diuretic. In one embodiment, the agent treating congestive heart failure is a beta-blocker, with or without a diuretic. In one embodiment, the agent treating congestive heart failure is digoxin. In one embodiment, the agent treating congestive heart failure is a diuretic such as thiazide diuretic, loop diuretic, potassium-sparing diuretic, or a combination thereof In one embodiment, the agent treating the cardiovascular system is an anti-arrhythmic agent. In one embodiment, the anti-arrhythmic agent is a sodium channel blocker, beta-adrenergic blocker, calcium channel blocker, or an agent that prolong repolarization, or combinations thereof. In one embodiment, the anti-arrhythmic agent is adenosine or digoxin.

In one embodiment, the agent treating the cardiovascular system is an anti-anginal agent. In one embodiment, the anti-anginal agent is an antiplatelet agent, adrenoceptor antagonist, calcium channel blocker, or a vasodilator. In one embodiment, the antiplatelet agent is a cyclooxygenase inhibitor, ADP inhibitor, phosphodiesterase III inhibitor, glycoprotein IIb/IIa inhibitor, or an adenosine reuptake inhibitor. In one embodiment, cardiac glycosides such as digitalis or ouabain may be used in combination with a metabolite of a SARM compound.

In one embodiment, the agent treating the cardiovascular system is a vasoactive agent or an inotrope.

In one embodiment, the agent treating the cardiovascular system is an anticoagulant agent. In one embodiment, the anticoagulant agent is a coumarin derivative or an unfractionated heparin. In one embodiment, the anticoagulant agent is fractionated heparin. In one embodiment, coumarin derivatives include but are not limited to warfarin.

In one embodiment, the agent treating the cardiovascular system is a fibrinolytic agent such as streptokinase, urokinase, alteplase, anistreplase, prourokinase, reteplase, tenecteplase, lanoteplase, staphylokinase, vampire, or alfimeprase.

In one embodiment, the agent treating the cardiovascular system is a hypercholesterolemic agent such as niacin-lovastatin, colestipol HCl, fluvastatin sodium, atorvastatin calcium, simvastatin, gemfibrozil, lovastatin, pravastatin sodium, cholestyramine, cholestyramine light, fenofibrate, colesevelam HCl, or ezetimibe.

In one embodiment, the metabolite of the SARM compound is administered in combination with an agent treating the gastrointestinal system. In one embodiment, the agent treating the gastrointestinal (GI) system is enhancing GI motility such as metoclopramide or cissapride. In one embodiment, the agent decreasing GI motility is an opioid such as morphine, diphenoxylate, loperamide hydrochloride, or opium.

In one embodiment, the agent treating the GI system is an adsorbent or a bulking agent. In one embodiment, the adsorbent is kaolin or other hydrated aluminum silicate clays. In one embodiment, the hydrated aluminum silicate clay is further combined with pectin. In one embodiment, adsorbents or bulking agents comprise bismuth subsalicylate, methylcellulose, psyllium derivative, or calcium polycarbophil.

In one embodiment, the agent treating the GI system is a stool softener.

In one embodiment, the agent treating the GI system is a laxative. In one embodiment, the agent treating the GI system is a bulk forming laxative as described hereinabove. In one embodiment, the laxative is an osmotic laxative such as lactulose, sorbitol, or polyethylene glycol. In one embodiment, the laxative is a saline laxative such as milk of magnesia, magnesium citrate, sodium phosphate, docusate potassium, sorbitol, sodium phosphate-biphosphate, or visicol.

In one embodiment, the agent treating the GI system is a cathartic stimulant. In one embodiment, the cathartic stimulant is an anthraquinone dervative such as cascara, aloe, senna, or rhubarb. In one embodiment, the cathartic stimulant is phenolphthalein, castor oil, or bisacodyl.

In one embodiment, the agent treating the GI system is an emetic agent. In one embodiment, the emetic agent is ipecac or apomorphine. In one embodiment, the agent treating the GI system is an anti-emetic agent such as antihistamine, anticholinergic agent, benzodiazepine, cannabinoid, dopamine antagonist, phenothiazine derivative, or 5-HT3 antagonist such as ondansetron or granisetron.

In one embodiment, the agent treating the GI system is an antacid. In one embodiment the antacid pharmaceutical preparation comprises buffering agents such as sodium bicarbonate, calcium carbonate, magnesium hydroxide, or aluminum hydroxide.

In one embodiment, the agent treating the GI system is an $H_2$-receptor antagonist. In some embodiments, the $H_2$-receptor antagonist is cimetidine, ranitidine, famotidine, or nizatidine.

In one embodiment, the agent treating the GI system is a proton pump inhibitor. In some embodiments, the proton pump inhibitor is omeprazole, lansoprazole, pantoprazole, rebeprazole, or esomeprazole In one embodiment, the agent treating the GI system is an agent treating inflammation. In one embodiment, the agent treating inflammation is 5-amino-salicylate, corticosteroid, metronidazole, ciprofloxacin, infiximab, budesonide, or anti-TNF alpha antibody.

In one embodiment, the metabolite of the SARM compound is administered in combination with an agent treating a dermatological disorder. In one embodiment, the agent treating a dermatological disorder is a corticosteroid or glucocorticosteroid such as betamethasone dipropionate, clobetasol, diflorasone, amcinonide, desoximetasone, fluocinonide, aclometasone, desonide triamcinolone, fluticasone, halobetasol, mometasone, or hydrocortisone. In one embodiment, the agent treating a dermatological disorder is a retinoid such as isotretinoin, acitretin, tretinoin, adapalene, tazarotene, bexarotene, alitretinoin, or beta-carotene.

In one embodiment, the agent treating a dermatological disorder is photochemotherapy agent. In one embodiment, the photochemotherapy agent is PUVA or psoralen such as oxsoralen. In one embodiment, the agent treating a dermatological disorder is a photodynamic agent such as porphyrin.

In one embodiment, the agent treating a dermatological disorder is daspone, thalidomide, anti-malarial agent, antimicrobial agent, or antifungal agent. In one embodiment, the anti-malarial agent is chloroquine or hydroxychloroquine; an antibiotic such as griseofulvin, ketoconazole, fluconazole, itraconazole, terbinafine, or potassium iodide; a topical antifungal agent, including but are not limited to ciclopirox, clotrimazole, econazole, ketoconazole, fluconazole, miconazole, naftifine, oxiconazole, terbinafine, or tolnaftate.

In one embodiment, the metabolite of the SARM compound is administered in combination with an anti-infective agent. In one embodiment, the anti-infective agent is an antibiotic agent. In one embodiment the antibiotic is a beta-lactam antibiotic. In one embodiment beta-lactam antibiotics include but are not limited to penicillin, benzathine penicillin, benzylpenicillin, amoxicillin, procaine penicillin, dicloxacillin, amoxicillin, flucloxacillin, ampicillin, methicillin, azlocillin, carbenicillin, ticarcillin, mezlocillin, piperacillin, phenoxymethylpenicillin, co-amoxiclav, cephalosporin, cefalexin, cephalothin, cefazolin, cefaclor, cefuroxime, cefamandole, cefotetan, cefoxitin, ceftriaxone, cefotaxime, ceftazidime, cefepime, cefpirome, imipenem, meropenem, ertapenem, faropenem, monobactam, aztreonam, or carbapenem.

In one embodiment the antibiotic is a tetracycline antibiotic. In one embodiment tetracycline antibiotics include but are not limited to tetracycline, chlortetracycline, demeclocycline, doxycycline, lymecycline, minocycline, or oxytetracycline.

In one embodiment the antibiotic is a macrolide antibiotic. In one embodiment macrolide antibiotics include but are not limited to erythromycin, azithromycin, oxithromycin, dirithromycin, clarithromycin, josamycin, oleandomycin, kitasamycin, spiramycin, tylosin/tylocine, troleandomycin, carbomycin, cethromycin, or telithromycin.

In one embodiment the antibiotic is an aminoglycoside antibiotic. In one embodiment, aminoglycoside antibiotics include but are not limited to gentamicin, tobramycin, kanamycin, neomycin, apramycin, paromomycin sulfate, streptomycin, or amikacin; or a quinolone antibiotic such as ciprofloxacin, norfloxacin, lomefloxacin, enoxacin, ofloxacin, ciprofloxacin, levofloxacin, sparfloxacin, gatifloxacin, moxifloxacin, trovafloxacin, or alatrofloxacin.

In one embodiment the antibiotic is a cyclic peptide antibiotic. In one embodiment cyclic peptide antibiotics include but are not limited to vancomycin, streptogramins, Microcin J25, Bacteriocin AS-48, RTD-1, or polymyxins.

In one embodiment the antibiotic is a lincosamide antibiotic. In one embodiment lincosamide antibiotics include but are not limited to clindamycin.

In one embodiment, the antibiotic is an oxazolidinone antibiotic. In one embodiment oxazolidinone antibiotics include but are not limited to linezolid, U-100592, DA-7867, AZD2563, or U-100766.

In one embodiment, the antibiotic is a sulfa antibiotic. In one embodiment, sulfa antibiotics include but are not limited to sulfisoxazole.

In one embodiment, the antibiotic is an antiseptic agent. In one embodiment, antiseptic agents include but are not limited to alcohols, chlorhexidine, chlorine, hexachlorophene, iodophors, chloroxylenol (PCMX), quaternary ammonium compounds, or triclosan.

In one embodiment, the antibiotic is an anti-tuberculosis agent. In one embodiment an anti-tuberculosis agents include but are not limited to ethambutol, rifabutin, isoniazid, rifampicin, pyrazinamide, or rifampin.

In one embodiment, the antibiotic is an antifungal agent. In one embodiment, antifungal agents include but are not limited to terbinafine, flucytosine, fluconazole, itraconazole, ketoconazole, ravuconazole, posaconazole, voriconazole, caspofungin, micafungin, v-echinocandin, amphotericin B, amphotericin B lipid complex (ABLC), amphotericin B colloidal dispersion (ABCD), liposomal amphotericin b (1-Amb), liposomal nystatin, or griseofulvin.

In one embodiment, the antibiotic is an antiprotozoal agent. In one embodiment the antiprotozoal agent is an antimalarial agent. In one embodiment, antimalarial agents include but are not limited to chloroquine, mefloquine, proguanil, pyrimethamine with dapsone, pyrimethamine with sulfadoxine, quinine, or primaquine. In one embodiment, the antiprotozoal agent is an amoebicide.

In one embodiment, amoebicides include but are not limited to metronidazole, tinidazole, or diloxanide furoate. In one embodiment, the antiprotozoal agent is an antigiadial agent. In one embodiment, antigiadial agents include but are not limited to metronidazole, tinidazole, or mepacrine. In one embodiment, the antiprotozoal agent is a leishmanicide. In one embodiment, leishmanicides include but are not limited to sodium stibogluconate. In one embodiment, the antibiotic is an antihelmintic agent.

In one embodiment, the antibiotic is an antiviral agent. In one embodiment, antiviral agents include but are not limited to abacavir, acyclovir, amantadine, didanosine, emtricitabine, enfuvirtide, entecavir, lamivudine, nevirapine, oseltamivir, ribavirin, rimantadine, stavudine, valaciclovir, vidarabine, zalcitabine, or zidovudine. In one embodiment, the antiviral agent is a nucleotide analog reverse transcriptase inhibitor. In one embodiment, nucleotide analog reverse transcriptase inhibitors include but are not limited totenofovir or adefovir. In one embodiment, the antiviral agent is a protease inhibitor. In one embodiment, protease inhibitors include but are not limited to saquinavir, ritonavir, indinavir, nelfinavir, amprenavir, lopinavir, fosamprenavir, or tipranavir. In one embodiment, the antiviral agent is a fusion inhibitor such as enfuvirtide. In one embodiment, a combination of antiviral or antiretroviral agents is desired. In one embodiment, antiviral or antiretroviral agents or a combination thereof, further comprise hydroxyurea, resveratrol, grapefruit, ritonavir, leflunomide, or a combination thereof.

In one embodiment, the metabolite of the SARM compound is administered in combination with an agent treating the liver. In one embodiment, the metabolite of the SARM compound is administered in combination with a statin. In some embodiment, statins include but are not limited to atorvastatin, fluvastatin, lovastatin, pravastatin, simvastatin, or rosuvastatin.

In one embodiment, the metabolite of the SARM compound is administered in combination with a bile acid sequestrant. In some embodiment, bile acid sequestrants include but are not limited to cholestyramine, colestipol, or colesevelam.

In one embodiment, the metabolite of the SARM compound is administered in combination with a cholesterol absorption inhibitor. In some embodiment, cholesterol absorption inhibitors include but are not limited to ezetimibe.

In one embodiment, the metabolite of the SARM compound is administered in combination with a nicotinic acid agent. In some embodiments, nicotinic acid agents include but are not limited to niacin, niacor, or slo-niacin.

In one embodiment, the metabolite of the SARM compound is administered in combination with a fibrate. In some embodiments, fibrates include but are not limited to gemfibrozil, or fenofibrate.

In one embodiment, the agent treating the liver is cortisone, cortisol or corticosterone. In some embodiments, the agent treating the liver is colchicine, methotrexate, ursodeoxycholic acid, or penicillamine.

In one embodiment, the metabolite of the SARM compound is administered in with an agent treating the kidney. In one embodiment, the agent treating the kidney is a diuretic. In some embodiments, diuretics include but are not limited to organomercurial, ethacrynic acid, furosemide, bumetanide, piretanide, muzolimine, chlorothiazide and thiazide, phthalimidine, chlorthalidone, clorexolone, quinazolinone, quinethazone, metolazone ilenzenesulphonamide, mefruside, chlorobenzamide, clopamidesalicylamide, xipamide, xanthine, aminophylline, carbonic anhydrase inhibitor, acetazolamide, mannitol, potassium-sparing compound, aldosterone antagonist, spironolactone and canrenoate, pteridines, pyrazine, carboxamide-triamterene, or amiloride. In one embodiment, the agent treating the kidney is a steroid.

In one embodiment, the agent treating the kidney is erythropoietin. In one embodiment, erythropoietin is obtained by natural sources (e.g., urinary erythropoietin; See U.S. Pat. No. 3,865,801), or is a recombinantly produced protein and analogs thereof, for example, as described in U.S. Pat. Nos. 5,441,868, 5,547,933, 5,618,698 and 5,621,080 as well as human erythropoietin analogs with increased glycosylation and/or changes in the amino acid sequence as those described in European Patent Publication No. EP 668351 and the hyperglycosylated analogs having 1-14 sialic acid groups and changes in the amino acid sequence described in PCT Publication No. WO 91/05867. In one embodiment, erythropoietin-like polypeptides are administered in combination with SARM compounds. In some embodiments, erythropoietin-like polypeptides comprise darbepoietin (from Amgen; also known as Aranesp and novel erthyropoiesis stimulating protein (NESP)).

In one embodiment, the metabolite of the SARM compound is administered in with an agent treating a metabolic disease. In some embodiments, agents treating a metabolic disease include but are not limited to a vitamin, Coenzyme Q10, glucosidase alfa, sodium bicarbonate, bisphosphonate, biotin, allopurinol, levodopa, diazepam, phenobarbital, haloperidol, folic acid, antioxidants, activators of cation channels haptoglobin, or carnitine.

In one embodiment, the agent treating a metabolic disease is a pancreatic lipase inhibitor such as orlistat or cetilistat, Serotonin or norepinephrine reuptake inhibitor such as sibutramine, insulin-sensitizers such as biguanide, PPAR agonist, dual-acting PPAR agonist such as muraglitazar, tesaglitazar, or naveglitazar, PPAR-delta agonist such as GW-501516, DPP-IV Inhibitor such as vildagliptin or sitagliptin, alpha glucosidase inhibitor such as acarbose, antidiabetic combination such as ActoPlusMet, AvandaMet, metformin/pioglitazone, metformin/rosiglitazone, or Glucovance, glucagon-like peptide-1 analogue such as exenatide or liraglutide, Amylin analogue such as pramlintide, statin such as atorvastatin, simvastatin, rosuvastatin, pravastatin, fluvastatin, lovastatin, or pitavastatin, cholesterol absorption inhibitor such as ezetimibe, nicotinic acid derivative such as niacin or Niaslo, antidyslipidemic fixed combination such as simvastatin/ezetimibe, lovastatin/nicotinic acid, atorvastatin/amlodipine, or atorvastatin/torcetrapib, simvastatin/nicotinic acid, ACE inhibitor such as ramipril, captopril, or lisinopril, AT-II receptor antagonist such as valsartan or telmisartan, cannabinoid receptor antagonist such as rimonabant, cholesteryl ester transfer protein or CETP Inhibitor such as JTT-705, CETi-1, or beta-3 adrenergic agonist.

In one embodiment, the metabolite of the SARM compound is administered with an agent treating a wasting disease. In some embodiments, agents treating a wasting disease include but are not limited to corticosteroids, anabolic steroids, cannabinoids, metoclopramid, cisapride, medroxyprogesterone acetate, megestrol acetate, cyproheptadine, hydrazine sulfate, pentoxifylline, thalidomide, anticytokine antibodies, cytokine inhibitors, eicosapentaenoic acid, indomethacin, ibuprofen, melatonin, insulin, growth hormone, clenbuterol, porcine pancreas extract, IGF-1, IGF-1 analogue and secretagogue, myostatin analogue, proteasome inhibitor, testosterone, oxandrolone, enbrel, melanocortin 4 receptor agonist, or a combination thereof.

In one embodiment, the agent treating a wasting disease is a ghrelin receptor ligand, growth hormone analogue, or a secretagogue. In some embodiments, ghrelin receptor ligands, growth hormone analogues, or secretagogues include but are not limited to pralmorelin, examorelin, tabimorelin, capimorelin, capromorelin, ipamorelin, EP-01572, EP-1572, or JMV-1843.

In one embodiment, growth promoting agents such as but not limited to TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890 are utilized as agents treating a wasting disease.

In other embodiments, agents treating a wasting disease may comprise growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or, in other embodiments, with growth hormone releasing factor and its analogs or growth hormone and its analogs, or with alpha-adrenergic agonists, such as clonidine or serotinin 5-HTD agonists, such as sumatriptan, or agents which inhibit somatostatin or its release, such as physostigmine and pyridostigmine. In some embodiments, agents treating a wasting disease may comprise parathyroid hormone, PTH(1-34) or bisphosphonates, such as MK-217 (alendronate). In other embodiments, agents treating wasting disease may further comprise estrogen, a selective estrogen receptor modulator, such as tamoxifene or raloxifene, or other androgen receptor modulators, such as those disclosed in Edwards, J. P. et. al., Bio. Med. Chem. Let., 9, 1003-1008 (1999) and Hamann, L. G. et. al., J. Med. Chem., 42, 210-212 (1999). In some embodiments, agents treating a wasting disease may further comprise a progesterone receptor agonists ("PRA"), such as levonorgestrel, medroxyprogesterone acetate (MPA). In some embodiments, agents treating a wasting disease may include nutritional supplements, such as those described in U.S. Pat. No. 5,179,080, which, in other embodiments are in combination with whey protein or casein, amino acids (such as leucine, branched amino acids and hydroxymethylbutyrate), triglycerides, vitamins (e.g., A, B6, B 12, folate, C, D and E), minerals (e.g., selenium, magnesium, zinc, chromium, calcium and potassium), camitine, lipoic acid, creatinine, B-hydroxy-B-methylbutyriate (Juven) and coenzyme Q. In one embodiment, agents treating a wasting disease may further comprise antiresorptive agents, vitamin D analogues, elemental calcium and calcium supplements, cathepsin K inhibitors, MMP inhibitors, vitronectin receptor antagonists, Src SH2 antagonists, vacular-$H^+$-ATPase inhibitors, ipriflavone, fluoride, tibolone, prostanoids, 17-beta hydroxysteroid dehydrogenase inhibitors and Src kinase inhibitors.

In one embodiment, the metabolite of the SARM compound is administered in with an agent treating the endocrine system. In some embodiments, agents treating the endocrine system include but are not limited to radioactive iodine, antithyroid agent, thyroid hormone supplement, growth hormone, cabergoline, bromocriptine, thyroxine, gonadotropin, glucocorticoid, glucocorticoid analogue, corticotrophin, metyrapone, aminoglutethimide, mitotane, ketoconazole, mifepristone, dexamethasone somatostatin analogue, gonadotropin-releasing hormone analogue, leuprolide, goserelin, antidiuretic hormone, antidiuretic hormone analogue, oxytocin, calcium supplement, vitamin D, or a combination thereof.

In one embodiment, the agent treating the endocrine system is a SARM compound. In some embodiments, SARMs include but are not limited to RU-58642, RU-56279, WS9761 A and B, RU-59063, RU-58841, bexlosteride, LG-2293, L-245976, LG-121071, LG-121091, LG-121104, LGD-2226, LGD-2941, YM-92088, YM-175735, LGD-1331, BMS-357597, BMS-391197, S-40503, BMS-482-404, EM-4283, EM-4977, BMS-564929, BMS-391197, BMS-434588, BMS-487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, or ACP-105.

In one embodiment, the additional agent treating the endocrine system is a SERM compound. In some embodiments, SERMs include but are not limited to tamoxifene, 4-hydroxytamoxifene, idoxifene, toremifene, ospemifene, droloxifene, raloxifene, arzoxifene, bazedoxifene, PPT (1,3,5-tris (4-hydroxyphenyl)-4-propyl-1H-pyrazole), diarylpropionitrile (DPN), lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstibestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, Ban zhi lian, CT-101, CT-102, or VG-101.

In one embodiment, the agent treating the endocrine system is a gonadotropin-releasing hormone agonist or antagonist. In some embodiments, gonadotropin-releasing hormone agonists or antagonists include but are not limited to leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, or acyline.

In one embodiment, the agent treating the endocrine system is a luteinizing hormone agonist or antagonist. In some embodiments, luteinizing hormone agonists or antagonists include but are not limited to letrozole, anastrazole, atamestane, fadrozole, or rogletimide. In one embodiment, the agent treating the endocrine system is a follicle stimulating hormone agonist or antagonist. In one embodiment, the agent treating the endocrine system is a luteinizing hormone releasing hormone (LHRH) or a LHRH analog.

In one embodiment, the agent treating the endocrine system is a steroidal or nonsteroidal glucocorticoid receptor ligand. In some embodiments, nonsteroidal glucocorticoid receptor ligands include but are not limited to ZK-216348, ZK-243149, ZK-243185, LGD-5552, mifepristone, RPR-106541, ORG-34517, GW-215864X, Sesquicillin, CP-472555, CP-394531, A-222977, AL-438, A-216054, A-276575, CP-394531, CP-409069, or UGR-07.

In one embodiment, the agent treating the endocrine system is a steroidal or non-steroidal progesterone receptor ligand. In one embodiment, the agent treating the endocrine system is a steroidal or nonsteroidal androgen receptor antagonist. In some embodiments, steroidal or nonsteroidal androgen receptor antagonists include but are not limited to flutamide, hydroxyflutamide, bicalutamide, nilutamide, or hydroxysteroid dehydrogenase inhibitor.

In one embodiment, the agent treating the endocrine system is a peroxisome proliferator-activated receptor ligand. In some embodiments, peroxisome proliferator-activated receptor ligands include but are not limited to bezafibrate, fenofibrate, gemfibrozil, darglitazone, pioglitazone, rosiglitazone, isaglitazone, rivoglitazone, netoglitazone, naveglitazar, farglitazar, tesaglitazar, ragaglitazar, oxeglitazar, or PN-2034.

In one embodiment, an agent treating the endocrine system is a human growth hormone. In some embodiments, human growth hormones include but are not limited to somatotropin or analogues.

In one embodiment, the agent treating the endocrine system is a ghrelin. In some embodiments, ghrelins include but are not limited to human ghrelin, CYT-009-GhrQb, L-692429, GHRP-6, SK&F-110679, or U-75799E.

In one embodiment, the agent treating the endocrine system is a leptin. In some embodiments, leptins include but are not limited to metreleptin or pegylated leptin. In one embodiment, an agent treating the endocrine system is a leptin receptor agonist. In some embodiments, leptin receptor agonists include but are not limited to LEP (116-130), OB3, [D-Leu4]-OB3, rAAV-leptin, AAV-hOB, or rAAVhOB.

In one embodiment, the metabolite of the SARM compound is administered with an inhibitor of an enzyme involved in the androgen biosynthetic pathway. In some embodiments, inhibitors of enzymes involved in the androgen biosynthetic pathway include but are not limited to 17-ketoreductase inhibitor, 3-$\Delta$H4,6-isomerase inhibitor, 3-$\Delta$H4,5-isomerase inhibitor, 17,20 desmolase inhibitor, p450c17 inhibitor, p450ssc inhibitor, or 17,20-lyase inhibitor.

In one embodiment, the SARM compound and/or metabolite as herein described is administered with an agent treating an ophthalmic disease. In some embodiments, agents treating an ophthalmic disease include but are not limited to Betagan, Betimol, Timoptic, Betoptic, Betoptic, Ocupress, Optipranolol, Xalatan, Alphagan, Azopt, Trusopt, Cospot, Pilocar, Pilagan, Propine, Opticrom, Acular, Livostin, Alomide, Emadine, Patanol, Alrex, Poly-Pred, Pred-G, Dexacidin, erythromycin, Maxitrol, Tobradex, Blephamide, FML, Ocufen, Voltaren, Profenal, Pred Forte, Econpred Plus, Eflone, Flarex, Inflamase Forte, betadine, gramicidin, prednisolone, betaxolol, humorsol, proparacaine, Betoptic, Hylartin, Inflamase Mild, Lotemax, flurbiprofen, chloramphenicol, methazolamide, timolol, Ciloxan, terramycin, ciprofloxacin, Miostat, triamcinolone, miconazole, tobramycin, physostimine, gentamicin, pilocarpine, bacitracin, goniosol, polymyxin, oxytetracycline, viroptic, Vexol, Suprofen, Celluvisc, Polytrim, Illotycin, Ciloxan, Ocuflox, Brinzolamide, Cefazolin, Tobrex, latanoprost, indocycanine, trifluridine, phenylephrine, demecarium, neomycin, tropicamide, dexamethasone, neptazane, dipivefrin, Ocuflox, vidarabine, dorzolamide, ofloxacin, epinephrine, acyclovir, carbonic anhydrase inhibitor, antihistamine, vitamin A, vitamin C, vitamin E, zinc, copper, atropine, or garamycin.

In one embodiment, the SARM compound and/or metabolite as herein described is administered in with a gene therapy agent. In some embodiments, gene therapy agents include but are not limited to an antisense agent, or a replacement gene.

In some embodiments, any of the compositions of this invention will comprise a metabolite of compound of formula I-IV, in any form or embodiment as described herein. In some embodiments, any of the compositions of this invention will consist of a compound of formula I-IV, in any form or embodiment as described herein. In some embodiments, of the compositions of this invention will consist essentially of a compound of I-IV, in any form or embodiment as described herein. In some embodiments, the term "comprise" refers to the inclusion of the indicated active agent, such as the compound of formula I-IV, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts.

The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

It is to be understood that this invention is directed to compositions and combined therapies as described herein, for any disease, disorder or condition, as appropriate, as will be appreciated by one skilled in the art. Any reference to a SARM or compound of this invention is to be understood as referring as well to a metabolite thereof, as herein described, and uses of the same in compositions and methods as herein described are to be considered as embodiments of this invention.

Certain applications of such compositions and combined therapies have been described hereinabove, for specific diseases, disorders and conditions, representing embodiments of this invention, and methods of treating such diseases, disorders and conditions in a subject by administering a SARM and/or metabolite as herein described, alone or as part of the combined therapy or using the compositions of this invention represent additional embodiments of this invention.

The following examples are presented in order to more fully illustrate the preferred embodiments of the invention. They should in no way be construed, however, as limiting the broad scope of the invention.

EXPERIMENTAL DETAILS SECTION

Example 1A

Synthesis of Compound I (2R)-1-Methacryloylpyrrolidin-2-carboxylic Acid. D-Proline, 14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The pH of the mixture was kept at 10-11° C. during the addition of the methacryloyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite, and evaporated in vacuo to give the crude product as a colorless oil. Recrystallization of the oil from ethyl ether and hexanes afforded 16.2 (68%) of the desired compound as colorless crystals: mp 102-103° C. (lit. [214] mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral center), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[α]_D^{26}$+80.8° (c=1, MeOH); Anal. Calcd. for $C_9H_{13}NO_3$: C, 59.00; H, 7.15; N, 7.65. Found: C, 59.13; H, 7.19; N, 7.61.

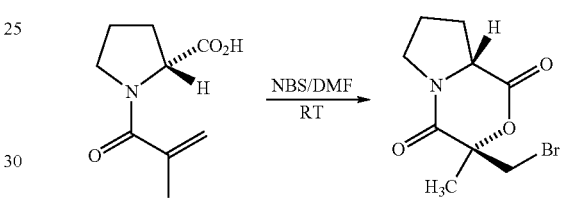

(3R,8aR)-3-Bromomethyl-3-methyl-tetrahydro-pyrrolo [2,1-c][1,4]oxazine-1,4-dione. A solution of NBS (23.5 g, 0.132 mol) in 100 mL of DMF was added dropwise to a stirred solution of the (methyl-acryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 (81%) (smaller weight when dried ~34%) of the title compound as a yellow solid: mp 152-154° C. (lit. [214] mp 107-109° C. for the S-isomer); $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[α]_D^{26}$+124.5° (c=1.3, chloroform); Anal. Calcd. for $C_9H_{12}BrNO_3$: C, 41.24; H, 4.61; N, 5.34. Found: C, 41.46; H, 4.64; N, 5.32.

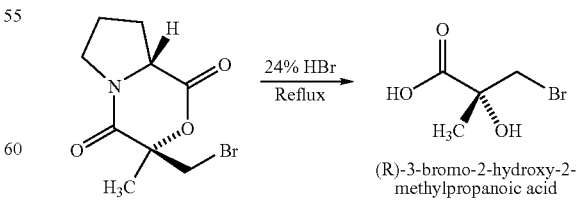

(2R)-3-Bromo-2-hydroxy-2-methylpropanoic Acid. A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite, and evaporated in vacuo to dryness. Recrystallization from toluene afforded 10.2 g (86%) of the desired compound as colorless crystals: mp 107-109° C. (lit. [214] mp 109-113° C. for the S-isomer); $^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[\alpha]_D^{26}$+10.5° (c=2.6, MeOH); Anal. Calcd. for C$_4$H$_7$BrO$_3$: C, 26.25, H, 3.86. Found: C, 26.28, H, 3.75.

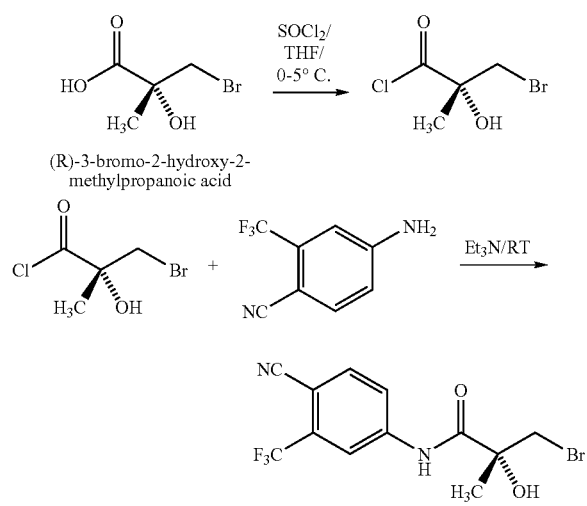

Synthesis of (2R)-3-Bromo-N-[4-cyano-3-(trifluoromethyl)phenyl]-2-hydroxy-2-methylpropanamide. Thionyl chloride (46.02 g, 0.39 mol) was added dropwise to a cooled solution (less than 4° C.) of (R)-3-bromo-2-hydroxy-2-methylpropanoic acid (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80: 20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M−H]-349.0. M.p.: 124-126° C.

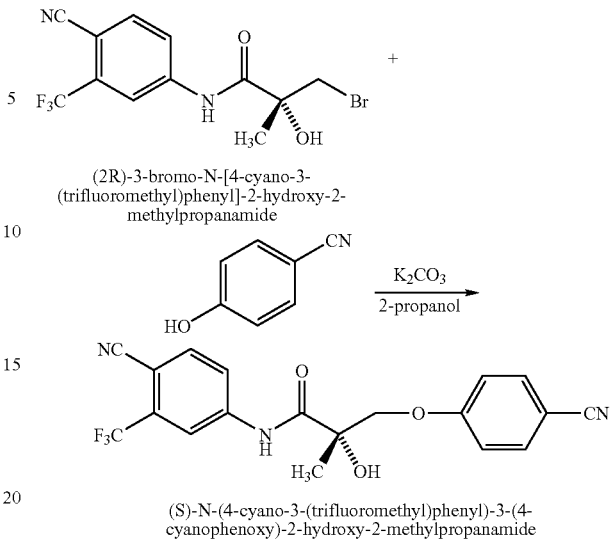

Synthesis of (S)—N-(4-cyano-3-(trifluoromethyl)phenyl)-3-(4-cyanophenoxy)-2-hydroxy-2-methylpropanamide. A mixture of bromoamide ((2R)-3-bromo-N-[4-cyano-3-(trifluoromethyl)phenyl]-2-hydroxy-2-methylpropanamide, 50 g, 0.14 mol), anhydrous K$_2$CO$_3$ (59.04 g, 0.43 mol), 4-cyanophenol (25.44 g, 0.21 mol) in 500 mL of 2-propanol was heated to reflux for 3 h and then concentrated under reduced pressure to give a solid. The resulting residue was treated with 500 mL of H$_2$O and then extracted with EtOAc (2×300 mL). The combined EtOAc extracts were washed with 10% NaOH (4×200 mL) and brine. The organic layer was dried over MgSO$_4$ and then concentrated under reduced pressure to give an oil which was treated with 300 mL of ethanol and an activated carbon. The reaction mixture was heated to reflux for 1 h and then the hot mixture was filtered through Celite. The filtrate was concentrated under reduced pressure to give an oil. This oil was purified by column chromatography using CH$_2$Cl$_2$/EtOAc (80:20) to give an oil which was crystallized from CH$_2$Cl$_2$/hexane to give 33.2 g (59.9%) of (S)—N-(4-cyano-3-(trifluoromethyl)phenyl)-3-(4-cyanophenoxy)-2-hydroxy-2-methylpropanamide as a colorless solid (a cotton type).

$^1$H NMR (CDCl$_3$/TMS) δ 1.63 (s, 3H, CH$_3$), 3.35 (s, 1H, OH), 4.07 (d, J=9.04 Hz, 1H, CH), 4.51 (d, J=9.04 Hz, 1H, CH), 6.97-6.99 (m, 2H, ArH), 7.57-7.60 (m, 2H, ArH), 7.81 (d, J=8.55 Hz, 1H, ArH), 7.97 (dd, J=1.95, 8.55 Hz, 1H, ArH), 8.12 (d, J=1.95 Hz, 1H, ArH), 9.13 (bs, 1H, NH). Calculated Mass: 389.10, [M−H]-388.1. Mp: 92-94° C.

Thus a compound of formula I was synthesized in one embodiment, according to the method hereinabove.

Example 1B

Synthesis of (S) Enantiomer of Compound of Formula (II)

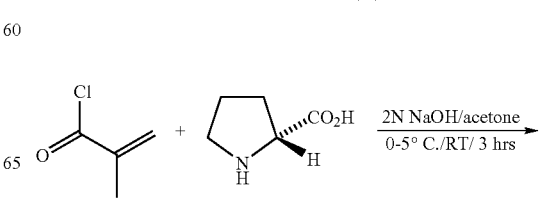

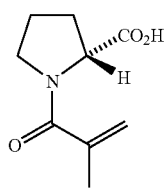

(2R)-1-Methacryloylpyrrolidin-2-carboxylic Acid. D-Proline, 14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The pH of the mixture was kept at 10-11° C. during the addition of the methacryloyl chloride. After stirring (3 h, room temperature), the mixture was evaporated in vacuo at a temperature of 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite, and evaporated in vacuo to give the crude product as a colorless oil. Recrystallization of the oil from ethyl ether and hexanes afforded 16.2 g (68%) of the desired compound as colorless crystals: mp 102-103° C. (lit. [214] mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[α]_D^{26}$+80.8° (c=1, MeOH); Anal. Calcd. for $C_9H_{13}NO_3$: C, 59.00; H, 7.15; N, 7.65. Found: C, 59.13; H, 7.19; N, 7.61.

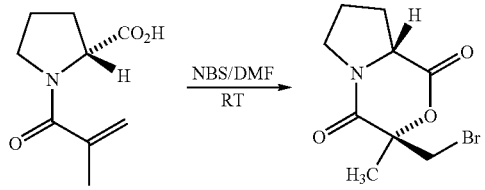

(3R,8aR)-3-Bromomethyl-3-methyl-tetrahydro-pyrrolo[2,1-c][1,4]oxazine-1,4-dione. A solution of NBS (23.5 g, 0.132 mol) in 100 mL of DMF was added dropwise to a stirred solution of the (methyl-acryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 g (81%) (smaller weight when dried ~34%) of the title compound as a yellow solid: mp 152-154° C. (lit. [214] mp 107-109° C. for the S-isomer); $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[α]_D^{26}$+124.5° (c=1.3, chloroform); Anal. Calcd. for $C_9H_{12}BrNO_3$: C, 41.24; H, 4.61; N, 5.34. Found: C, 41.46; H, 4.64; N, 5.32.

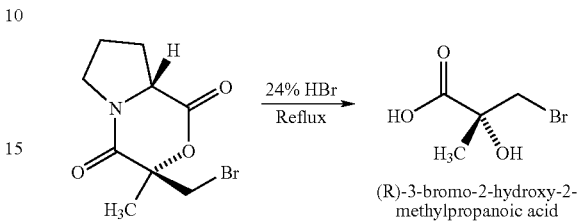

(2R)-3-Bromo-2-hydroxy-2-methylpropanoic Acid. A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts with concentrated HCl to pH=1, which, in turn, was extracted with ethyl acetate (100 mL×4). The combined organic solution was dried over $Na_2SO_4$, filtered through Celite, and evaporated in vacuo to dryness. Recrystallization from toluene afforded 10.2 g (86%) of the desired compound as colorless crystals: mp 107-109° C. (lit. [214] mp 109-113° C. for the S-isomer); $^1$H NMR (300 MHz, DMSO-$d_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[α]_D^{26}$+10.5° (c=2.6, MeOH); Anal. Calcd. for $C_4H_7BrO_3$: C, 26.25, H, 3.86. Found: C, 26.28, H, 3.75 were washed with saturated NaHCO$_3$ (100 mL×4). The aqueous solution was acidified

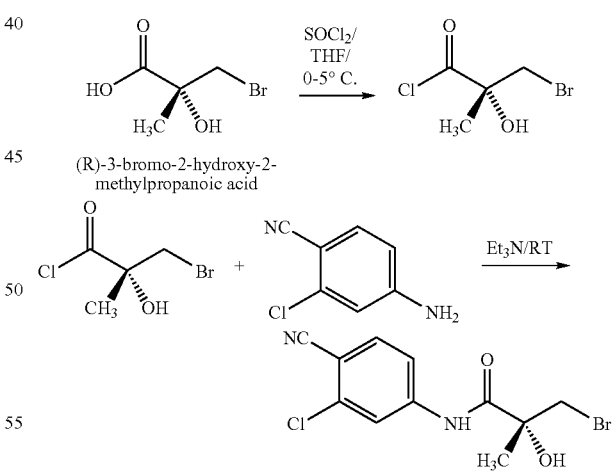

Synthesis of (2R)-3-bromo-N-(3-chloro-4-cyanophenyl)-2-hydroxy-2-methylpropanamide. Thionyl chloride (7.8 g, 65.5 mmol) was added dropwise to a cooled solution (less than 4° C.) of (R)-3-bromo-2-hydroxy-2-methylpropanoic acid (9.0 g, 49.2 mol) in 50 mL of THF under an argon atmosphere. The resulting mixture was stirred for 3 h under the same condition. To this was added Et$_3$N (6.6 g, 65.5 mol) and stirred for 20 min under the same condition. After 20 min, 4-amino-2-chlorobenzonitrile (5.0 g, 32.8 mmol) and 100 mL of THF were added and then the mixture was allowed to stir overnight at room temperature. The solvent was removed under reduced pressure to give a solid which was treated with 100 mL of H$_2$O, extracted with EtOAc (2×150 mL). The combined organic extracts were washed with saturated NaHCO$_3$ solution (2×100 mL) and brine (300 mL), successively. The organic layer was dried over MgSO$_4$ and concentrated under reduced pressure to give a solid which was purified from column chromatography using EtOAc/hexane (50:50) to give 7.7 g (49.4%) of target compound as a brown solid.

$^1$H NMR (CDCl$_3$/TMS) δ 1.7 (s, 3H, CH$_3$), 3.0 (s, 1H, OH), 3.7 (d, 1H, CH), 4.0 (d, 1H, CH), 7.5 (d, 1H, ArH), 7.7 (d, 1H, ArH), 8.0 (s, 1H, ArH), 8.8 (s, 1H, NH). MS:342.1 (M+23). Mp 129° C.

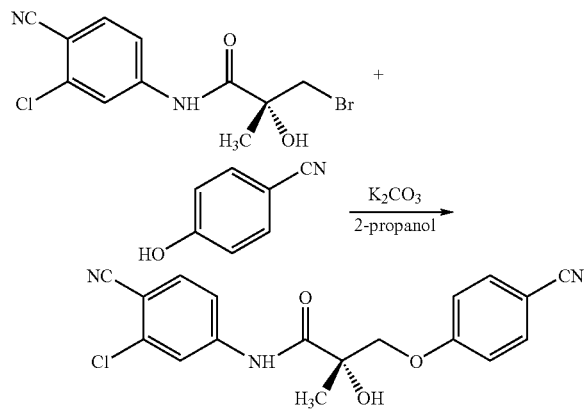

Synthesis of (S)—N-(3-chloro-4-cyanophenyl)-3-(4-cyanophenoxy)-2-hydroxy-2-methylpropanamide. A mixture of bromoamide (2.0 g, 6.3 mmol), anhydrous K$_2$CO$_3$ (2.6 g, 18.9 mmol) in 50 mL of acetone was heated to reflux for 2 h and then concentrated under reduced pressure to give a solid. The resulting solid was treated with 4-cyanophenol (1.1 g, 9.5 mmol) and anhydrous K$_2$CO$_3$ (1.7 g, 12.6 mmol) in 50 mL of 2-propanol was heated to reflux for 3 h and then concentrated under reduced pressure to give a solid. The residue was treated with 100 mL of H$_2$O and then extracted with EtOAc (2×100 mL). The combined EtOAc extracts were washed with 10% NaOH (4×100 mL) and brine, successively. The organic layer was dried over MgSO$_4$ and then concentrated under reduced pressure to give an oil which was purified by column chromatography using EtOAc/hexane (50:50) to give a solid. The solid was recrystallized from CH$_2$Cl$_2$/hexane to give 1.4 g (61.6%) of (S)—N-(3-chloro-4-cyanophenyl)-3-(4-cyanophenoxy)-2-hydroxy-2-methylpropanamide as a colorless solid.

$^1$H NMR (CDCl$_3$/TMS) δ 1.61 (s, 3H, CH$_3$), 3.25 (s, 1H, OH), 4.06 (d, J=9.15 Hz, 1H, CH), 4.50 (d, J=9.15 Hz, 1H, CH), 6.97-6.99 (m, 2H, ArH), 7.53-7.59 (m, 4H, ArH), 7.97 (d, J=2.01 Hz, 1H, ArH), 8.96 (s, 1H, NH). Calculated Mass: 355.1, [M+Na]$^+$ 378.0. Mp: 103-105° C.

Example 2

Metabolism of Compound I

Methods

Metabolism of Compound I in Human Liver, Dog liver, Monkey liver, Rat liver and Rat Hepatocytes:

Animals were fed ad libitum, and housed according to institutional and NIH guidelines. Sprague Dawley rats received from 10 to 300 mg/kg Compound I, dissolved in 10% Ethanol:90% PEG300 and administered by oral gavage; beagle dogs received a 100 mg/kg intravenous (IV) dose of Compound I. Informed consent was obtained from Human subjects enrolled in a clinical trial where subjects were administered 0.1 to 10 mg/drug per day for up to 90 days. The human oral doses were delivered as single once daily oral doses, or as a divided dose of 3 mg administered as 10 doses of 0.3 mg of drug in capsules over a 24 hour period.

Various sample preparations were performed for the experiments described herein. Generally, plasma and fecal samples were prepared using a liquid-liquid extraction method. Organ samples were weighed and minced with a scalpel. Aliquots of each organ sample was placed in 1 mL of ScintiGest® tissue solubilizer (Fisher Scientific Company, Fair Lawn, N.J.), and then homogenized using a Pro 200 homogenizer (Pro Scientific, Monroe, Conn.). The samples were incubated at 60° C. until tissue dissolved. The total radioactivity of the urine, and fecal samples were determined using a Beckman LS6000 IC liquid scintillation counter (Beckman-Coulter, Fullerton, Calif.). Radioactive urine and feces samples were also separated using a reversed phase column to identify the fractions of parent drug and metabolites. Eluent fractions from the HPLC were collected in 2 minute intervals and counted as described. Nonradioactive urine and feces samples were filtered and analyzed by LC/MS$^n$. The LC/MS system consisted of a Surveyor MS pump, Surveyor autosampler, and LCQ Deca MS (Thermo-Finnigan, San Jose, Calif.). Blank feces and urine samples were used to subtract the background spectra from that of the treated samples to identify drug related peaks. Metabolite ID software was used to identify metabolite peaks by comparing the MS and MS/MS of the metabolite spectra to that of authentic Compound I.

Liver microsome preparations from samples treated with test compound or vehicle were assessed by LC-MS and LC-MS/MS to determine the main metabolites of Compound I. Test compounds were incubated at a final concentration of 0.5 mM with the respective samples. Human liver microsomes and hepatocytes were utilized at a final concentration of 1.0 mg/ml and 1×10$^6$ cells/ml, respectively. Duplicate wells were used for each time point (0, 5, 10, 30, and 60 minutes). The concentrations of parent drug remaining in each well were analyzed on an MDS/Sciex API4000 Q Trap system with electrospray ionization (ESI) in the positive and/or negative SIM mode, depending on the test compound(s). The intrinsic clearance rates (CLint) were calculated from 0-60 minutes based on first order decay kinetics as a function of microsomal protein concentration, or (for hepatocyte assays) as a function of hepatocellularity and organ-to-body weight—expressed in units of mL/min/kg. For hepatocyte assays, cell viability was also monitored at each time point (from replicate wells) using the Trypan Blue exclusion method.

Cytochrome P450 enzyme inhibition was measured using human, cDNA-expressed CYP3A4, 2D6, 2C19, 2C9, and 1A2 enzymes. Analogues of the model substrate coumarin were utilized for each isozyme, at a concentration near the apparent Km of this substrate. Compound stocks were tested using an 8-point dose-response curve in duplicate (ranging from 0.15 mM-20.0 mM). IC$_{50}$ values were calculated as the point where 50% inhibition of the enzyme's catalytic activity occurs. For microsome-based CYP inhibition measurements, all substrates were utilized at the approximate Km value. For CYP induction assays, the procedure of Roymans et al. (D. Roymans et al. *Drug Metab. Dispos.* (2005), 33(7), 1004-

1016) was followed, using a 72-hour differentiation and 72-hour drug treatment time course. Duplicate wells in the induction assay were used to measure both functionality and expression of the CYP enzyme.

Permeability (and efflux potential) was measured in the Apical (pH 6.5) to Basolateral (pH 7.4) and Basolateral (pH 7.4) to Apical (pH 6.5) directions across polarized, Caco-2 epithelial monolayers. Compound stocks were tested at a final concentration of 10 mM. The concentration of drug in the receiver well was measured by LC/MS/MS using a standard curve. The apparent permeability (Papp) for each compound was calculated, and values (A-B) were classified as: Poor (Papp: <1), Low (Papp 1-2), Medium (Papp 2-10) or High (Papp>10).

Results

Compound I is a potent and efficacious selective androgen receptor modulator (SARM). In order to identify main phase I metabolites of compound I, liver samples (hepatocytes or microsomes) were assessed from various species. Toward this end, human liver microsomes (HLM), dog liver microsomes, monkey liver microsomes, rat liver microsomes and rat hepatocytes were evaluated after incubation of compound I. The in vitro half-life of the compound was assessed for each test compound, and the potential of the compound to inhibit or induce any of five major isoenzymes of the cytochrome P450 family was evaluated as well.

Figure 3:
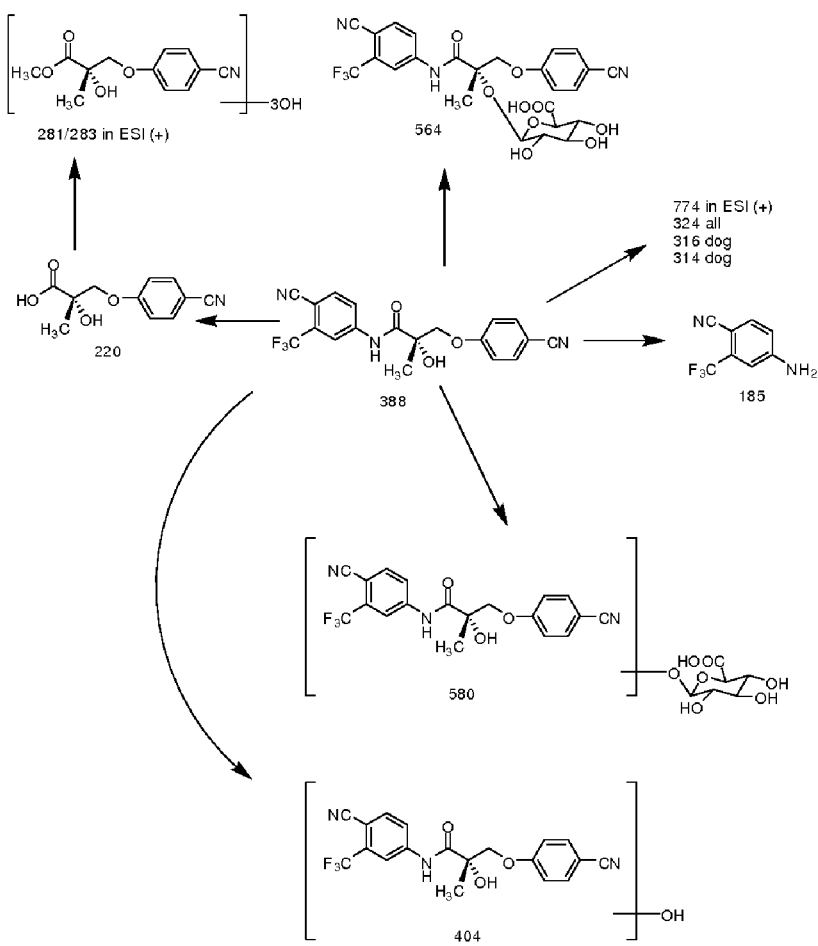
FIG. 3: schematically depicts a metabolic pathway of compound I.
Figure 4:
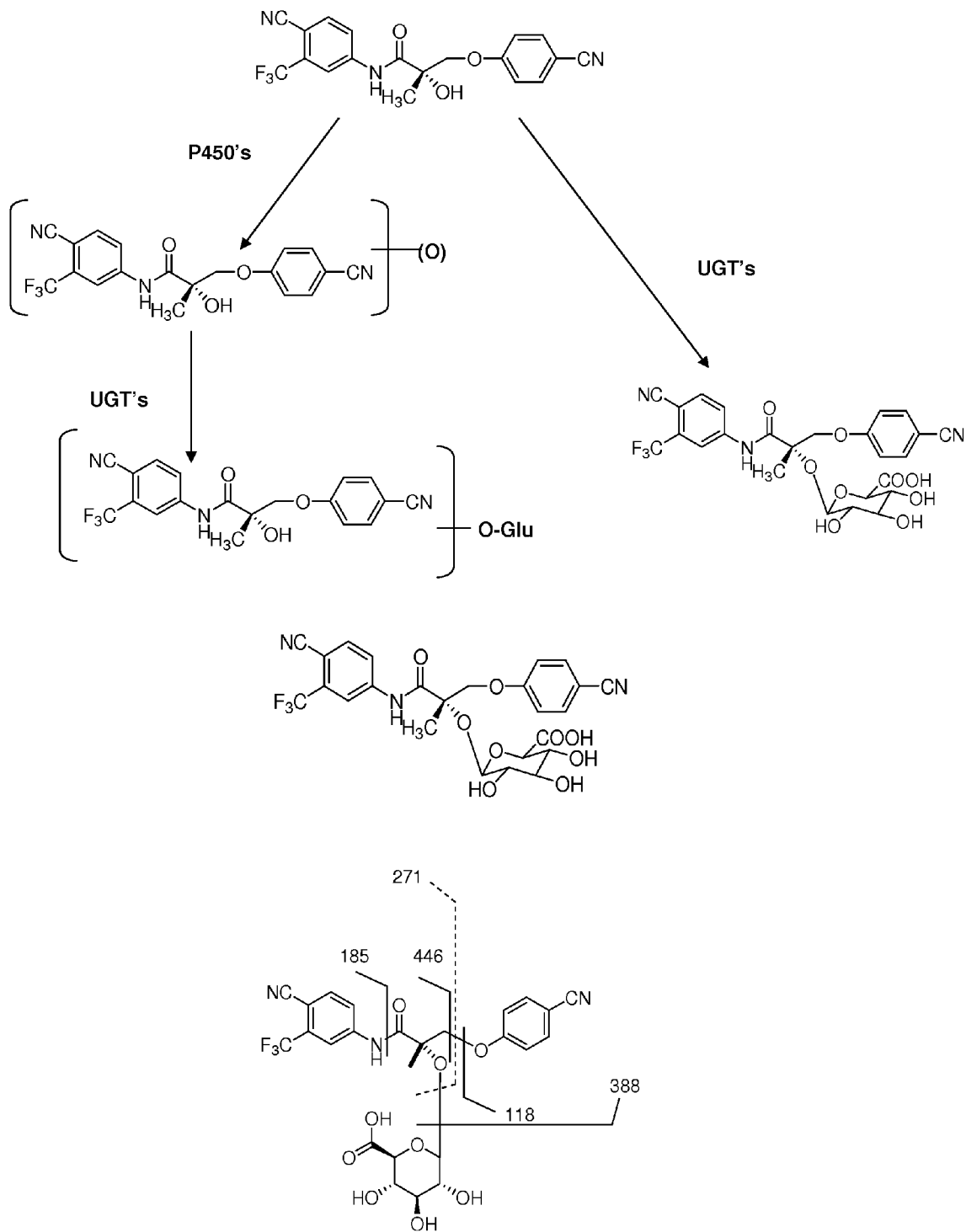
FIG. 4: schematically depicts another metabolic profile of compound I.

Incubations of Compound I (m/z 388) with liver microsomes or hepatocytes produced eight major metabolites (m/z 564, 580, 404, 281, 185, 314, 316 and 324) (FIGS. 3 and 4). Fragmentation patterns of the metabolites were compared to the parent compound to determine the sites of metabolic modification. The results are presented in Table 1, including structural information gathered by LC/MS/MS fragmentation.

TABLE 1

| Molecular Ion [M − H]− | Assigned Structures and Proposed Fragmentation Pattern |
|---|---|
| 564 | 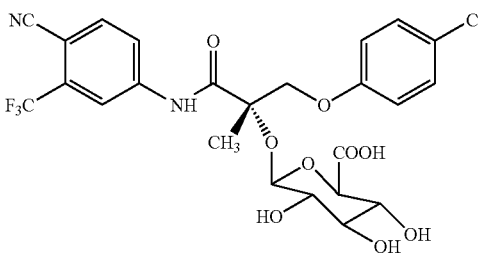 Glucuronidation: phase II |
| 580 | 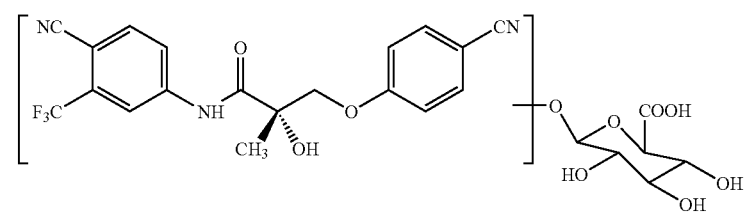 Mono hydroxylation and Glucuronidation: Phase I + II |
| 404 | 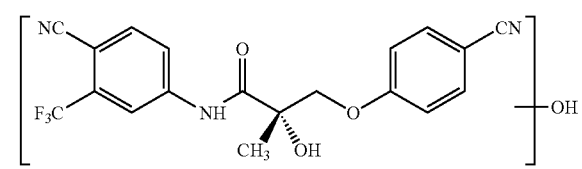 Mono hydroxylation: Phase I |
| 281 | 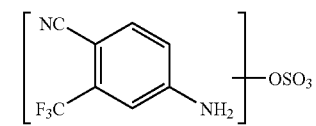 Amide hydrolysis and hydroxylation: Phase I |
| 220 | 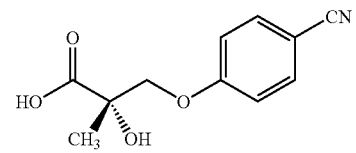 Amide hydrolysis (B ring): Phase I |

TABLE 1-continued

| Molecular Ion [M − H]− | Assigned Structures and Proposed Fragmentation Pattern |
|---|---|
| 185 | 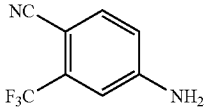<br>Amide hydrolysis (A ring): Phase I |

Figure 5:
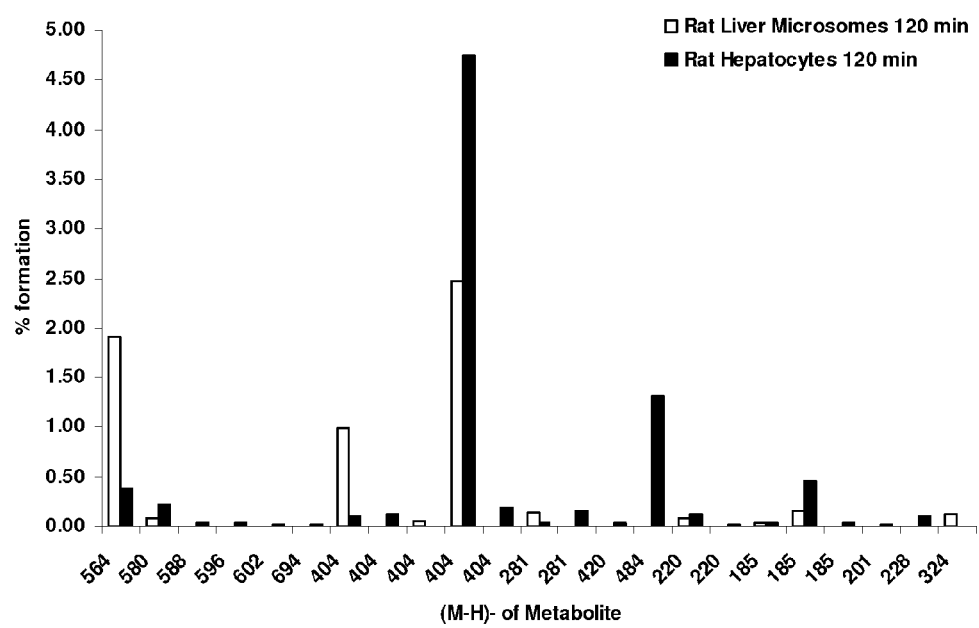
FIG. 5: plots the percent formation of specific metabolites of compound I.
Figure 6:
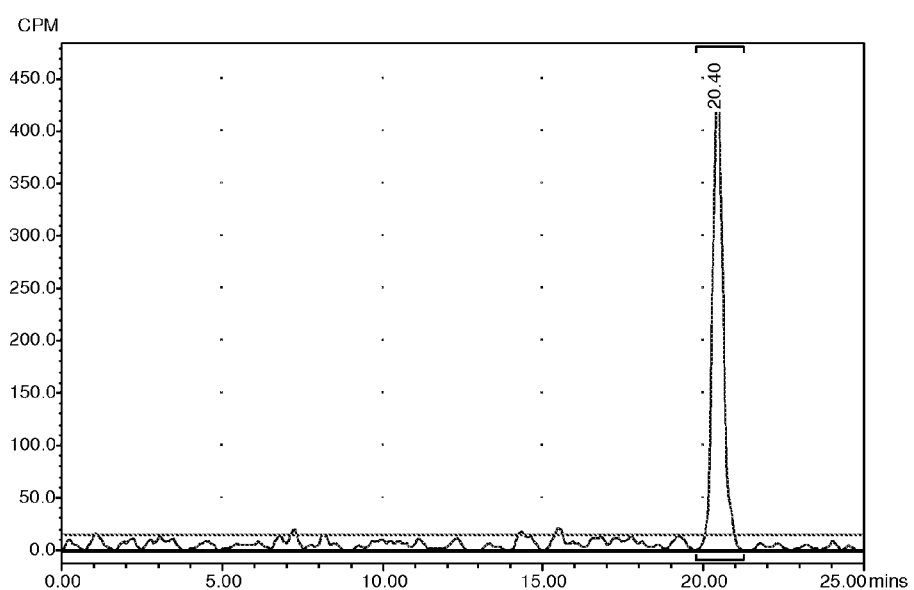
FIG. 6: depicts a radiochromatogram of sample from plasma-Pool 1 (JVC Male) following oral administration of Compound 1 to male Sprague Dawley rats.
Figure 7:
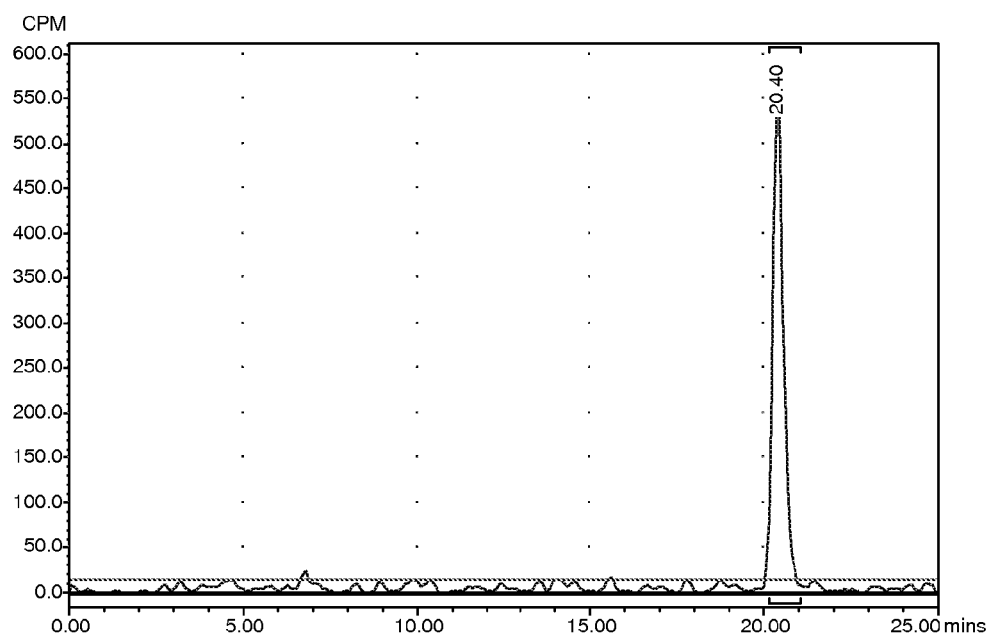
FIG. 7 depicts a radiochromatogram of sample from plasma-Pool 2 (JVC Female) following oral administration of Compound 1 to female Sprague Dawley rats.
Figure 8:
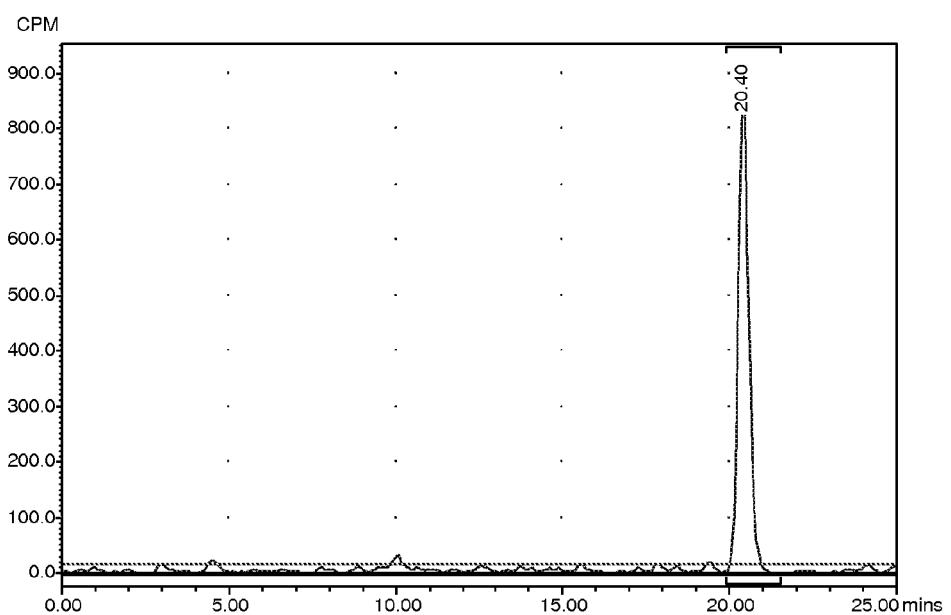
FIG. 8 depicts a radiochromatogram of sample from plasma-Pool 3 (FVC/JVC Male) following intravenous administration of Compound I to male Sprague Dawley rats.
Figure 9:
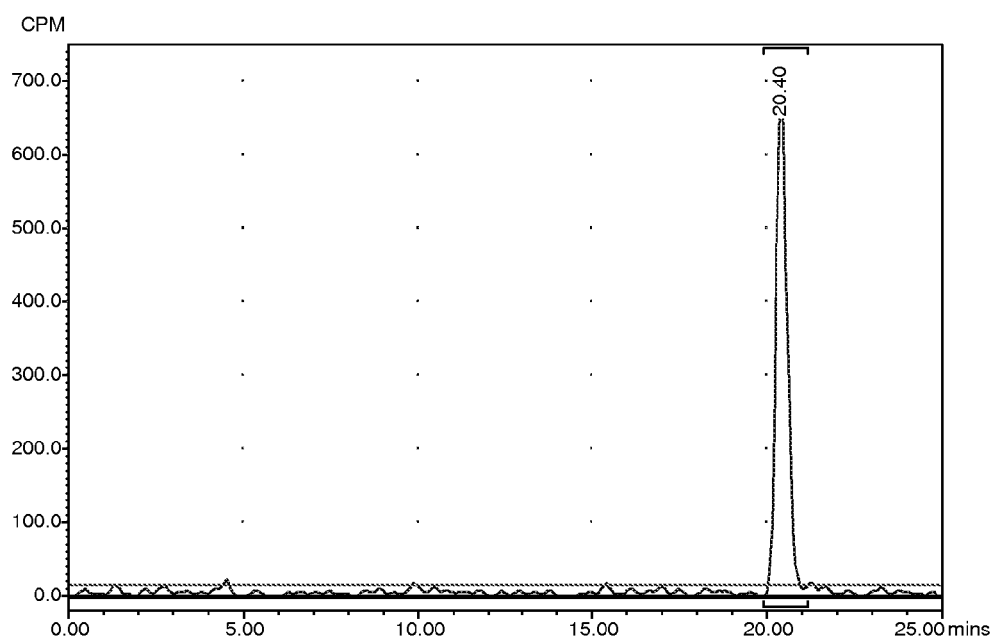
FIG. 9 depicts a radiochromatogram of sample from plasma-Pool 4 (FVC/JVC Female) following intravenous administration of Compound I to female Sprague Dawley rats.
Figure 10:
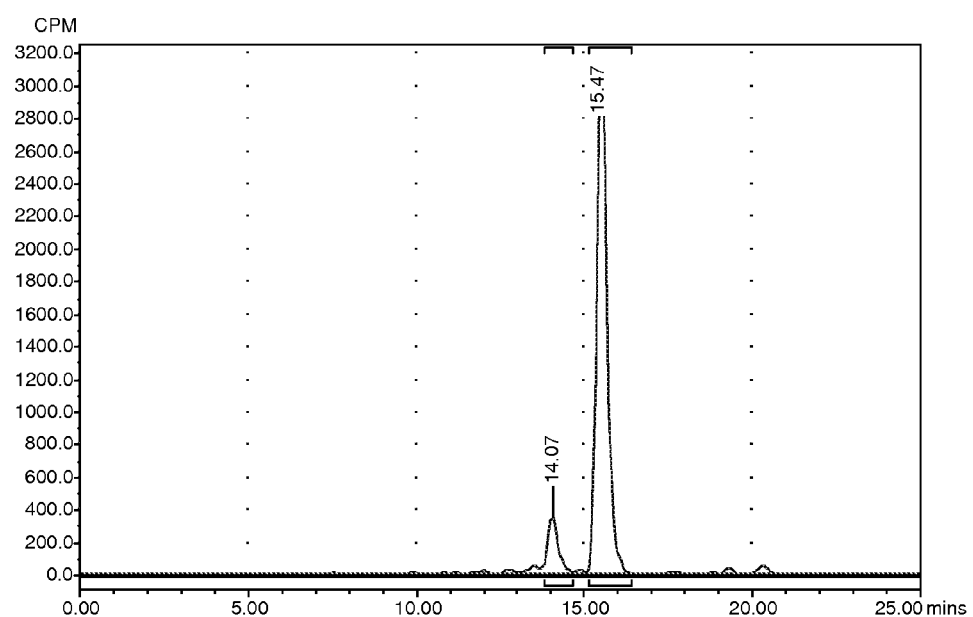
FIG. 10 depicts a radiochromatogram of sample from bile (BDC Male) following oral administration of Compound I to male Sprague Dawley rats.
Figure 11:
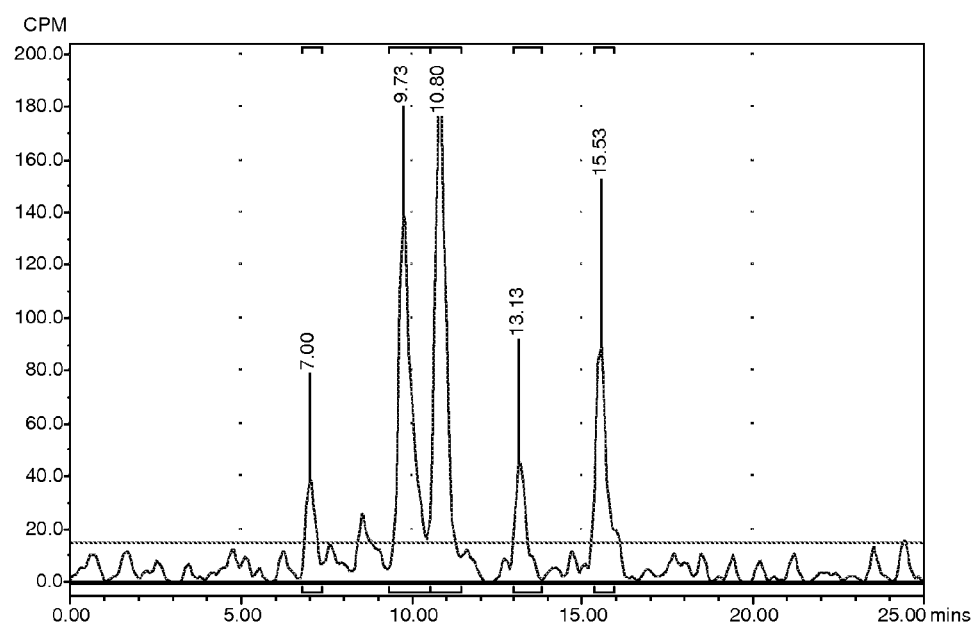
FIG. 11 depicts a radiochromatogram of sample from urine-Pool 1 (Intact Male) following oral administration of Compound I to male Sprague Dawley rats.
Figure 12:
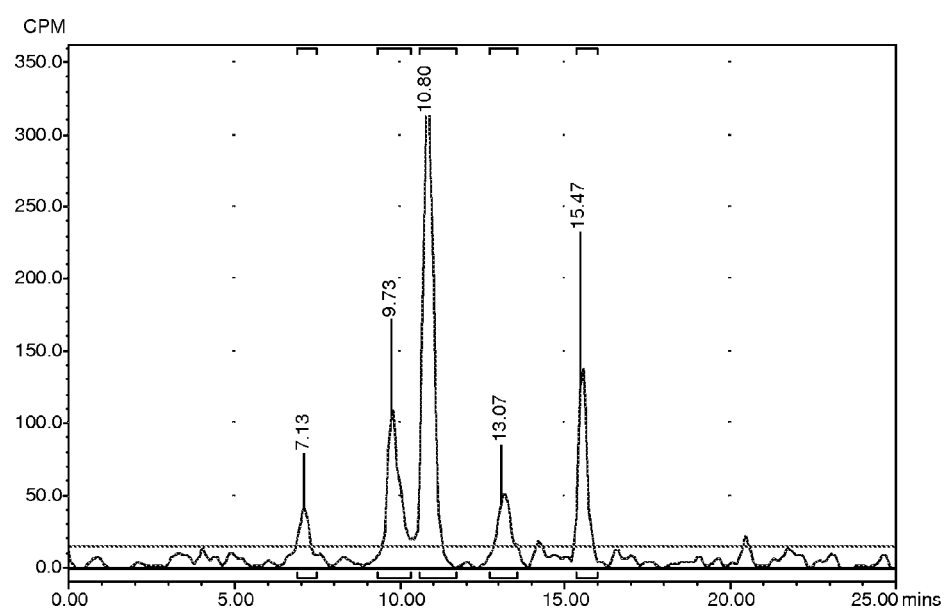
FIG. 12 depicts a radiochromatogram of sample from urine-Pool 2 (Intact Female) following oral administration of Compound I to female Sprague Dawley rats.
Figure 13:
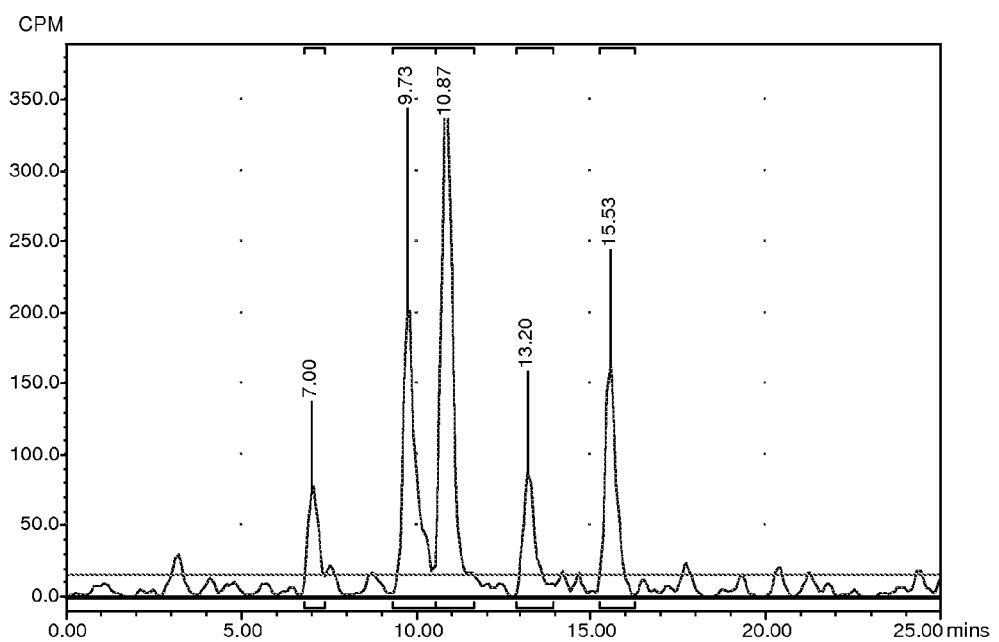
FIG. 13 depicts a radiochromatogram of sample from urine-Pool 3 (BDC Male) following oral administration of Compound I to male Sprague Dawley rats.

Comparison of the relative abundance of in vitro metabolites of Compound I (m/z 388) in Rat-Liver Microsomes and Rat Hepatocytes is presented in Table 2 and FIG. 5.

TABLE 2

| Metabolite (M − H)− | Metabolite ID | Rat Liver Microsomes | Rat Hepatocytes |
|---|---|---|---|
| 564 | Compound I Glucuronidation (gluc) | 1.92 | 0.37 |
| 580 | Mono Hydroxylation mono gluc | 0.08 | 0.22 |
| 588 | B ring Hydroxylation di gluc | 0.00 | 0.03 |
| 596 | Compound I tri hydroxy di sulfate | 0.00 | 0.03 |
| 602 | B ring hydroxy methyl di gluc | 0.00 | 0.02 |
| 404 | Mono Hydroxylation | 0.98 | 0.10 |
| 404 | Mono Hydroxylation | 0.00 | 0.13 |
| 404 | Mono Hydroxylation | 0.04 | 0.00 |
| 404 | Mono Hydroxylation | 2.47 | 4.75 |
| 404 | Mono Hydroxylation | 0.0 | 0.19 |
| 281 | Amide Hydrolysis (A ring) and hydroxylation plus mono sulfate | 0.13 | 0.03 |
| 281 | Amide Hydrolysis (A ring) and hydroxylation plus mono sulfate | 0.00 | 0.15 |
| 420 | Compound I dihydroxy | 0.00 | 0.03 |
| 484 | Compound I mono hydroxy mono sulfate | 0.00 | 1.31 |
| 220 | Amide Hydrolysis (B Ring) | 0.08 | 0.12 |
| 220 | Amide Hydrolysis (B Ring) | 0.00 | 0.02 |
| 185 | Amide Hydrolysis (A Ring) | 0.04 | 0.03 |
| 185 | Amide Hydrolysis (A Ring) | 0.15 | 0.46 |
| 185 | Amide Hydrolysis (A Ring) | 0.00 | 0.04 |
| 201 | A ring Hydrolysis and hydroxylation | 0.00 | 0.02 |
| 228 | B ring N-Oxide | 0.00 | 0.10 |
| 324 | unknown | 0.11 | 0 |

Metabolites observed in positive ionization mode are presented in Table 3.

Metabolic stability of Compound I and R-bicalumide are measured in human liver microsomes and primary monkey hepatocytes as presented in Table 4.

Efflux Potential and Permeability Profile of Compound I and R-bicalumide as measured in Caco-2 Monolayers is presented in Table 5.

TABLE 5

| Compound | A-B Papp ($10^{-6}$ cm/sec) | Permeability Classification | B-A Papp ($10^{-6}$ cm/sec) | Efflux Ratio (B-A/A-B) |
|---|---|---|---|---|
| I | 26.3 | High | 29.0 | 1.1 |
| R-Bicalutamide | 23.2 | High | 22.8 | 1.0 |

Screening for Potential Drug-Drug Interactions (DDI): In Vitro CYP Inhibition Profile of SARMs is presented in Table 6.

TABLE 6

| | CYP (P450) Inhibition, $IC_{50}$ (µM) | | | | |
|---|---|---|---|---|---|
| Compound | 3A4 | 2D6 | 2C19 | 2C9 | 1A2 |
| I | >20 | >20 | 8.9 | 1.6 | >20 |
| R-Bicalutamide | 2.4 | >20 | 5.6 | >20 | >20 |

Compound I does not induce CYP3A4 activity in primary human hepatocytes as presented in Table 7.

TABLE 7

| Compound | Concentration | Rate of Reaction Terfenadine C-hydroxylation (pmol/$10^6$ cells/min) | Fold Induction |
|---|---|---|---|
| Vehicle only | — | 1.1 | — |
| Compound I | 1 mM | 1.2 | none |
| Compound I | 10 mM | 1.2 | none |
| Rifampin (positive control) | 10 mM | 8.1 | 7.4 |

TABLE 4

| | Monkey Hepatocytes | | Human Liver Microsomes | | | |
|---|---|---|---|---|---|---|
| | | | Half-Life | | Half-Life | |
| Compound | Half-Life (minutes) | CLint (ml/min/kg) | (minutes) Phase I | CLint (ml/min/mg) Phase I | (minutes) Phase I + II | CLint (ml/min/mg) Phase I + II |
| I | Stable | <1 | Stable | <1 | Stable | <1 |
| R-Bicalutamid | Stable | <1 | Stable | <1 | Stable | <1 |

Compound I does not induce CYP2C9 activity in primary human hepatocytes as presented in Table 8.

TABLE 8

| Compound | Concentration | Rate of Reaction Terfenadine C-hydroxylation (pmol/$10^6$ cells/min) | Fold Induction |
|---|---|---|---|
| Vehicle only | — | 0.77 | — |
| Compound I | 1 mM | 0.62 | none |
| Compound I | 10 mM | 0.56 | none |
| Rifampin (positive control) | 10 mM | 1.46 | 1.9 |

Conclusions:

Compound I was directly converted to its glucuronide metabolite (m/z 564) without Phase I metabolism, with the glucuronide conjugate being the major metabolite observed in human liver microsome samples. A second major metabolite identified was the mono hydroxy glucuronidated compound (m/z 580) (Phase I+II). Following this, the next metabolite in terms of abundance was the mono hydroxylated (m/z 404) metabolite (Phase I). Amide hydrolysis products (m/z 281, 185) were observed, although in exceptionally low abundance, from microsomal samples of almost all species evaluated, with dogs showing the highest percentage of such products.

Monkey liver microsomes and human liver microsomes showed similar metabolite profiles.

Overall, inter-species metabolite profiles were relatively similar. However, under Phase I conditions only, dog liver microsomes generated a subtly different profile than the other microsomes evaluated (human, monkey, rat). Monohydroxy m/z 404 (Phase I) and amide hydrolysis products (m/z 281) were the primary metabolites observed in dog microsomes under Phase I conditions. The mono hydroxy metabolite (m/z 404) was observed at four different retention times indicating hydroxylation at four different places (aromatic hydroxylation on ring A, B and/or aliphatic hydroxylation).

The results of the in vitro half-life as determined from the microsomal and hepatocyte assays indicated that Compound I was mostly stable under both phase I and phase I/II metabolic conditions, suggesting a low metabolic conversion rate would be expected in vivo The results of the Caco-2 permeability assays indicated that compound I had a high permeability classification and low efflux potential, which correlates with good expected intestinal absorption after oral administration and low cellular clearance.

Example 3

Androgenic & Anabolic Activity of Compound I in Intact and ORX Subjects

Male Sprague-Dawley rats are administered Compound I and the glucuronide metabolite, as well as other metabolites identified in Example 2 to intact and orchidectomized (ORX) animals.

The compound and metabolites are administered via oral gavage at various doses, for example 0.01, 0.03, 0.1, 0.3, 0.75, and 1 mg/day to both intact and ORX groups. The animals are sacrificed under anesthesia (ketamine/xyalzine, 87:13 mg/kg) after a 14-day dosing regimen, and body weights are recorded. In addition, ventral prostate, seminal vesicles, and levator ani muscle are removed, individually weighed, normalized to body weight, and expressed as a percentage of intact control. Student's T-test is used to compare individual dose groups to the intact control group. As a measure of androgenic activity, ventral prostate and seminal vesicle weights are evaluated, whereas levator ani muscle weight is evaluated as a measure of anabolic activity. Blood is collected from the abdominal aorta, centrifuged, and sera were frozen at −80° C. prior to determination of serum hormone levels. Serum lutenizing hormone (LH) and follicle stimulating hormone (FSH) concentrations are determined.

Example 4

SARM Reduction of Cholesterol Levels

Sprague Dawley rats (male and female) are divided into groups administered vehicle only (PEG300: 40% Cavasol® [75/25 (v/v)]), and different dosages of Compound I, and the metabolites of Example 2. Animals are administered the compounds once daily by oral gavage. After 28 consecutive days of dosing, animals are fasted overnight, blood samples are collected and serum is obtained. Serum levels of total cholesterol are determined using an automated laboratory assay method.

Example 5

SARM Promotion of Lean Mass and Reduction of Fat Mass

Human clinical trials are conducted on elderly men (age>60) and postmenopausal women (not hypogonadal, not osteoporotic, no exercise program, no controlled diet) administered the compounds of Example 2, in solution or in experimental capsules for a 90 day treatment regimen. Total lean body mass (as DEXA=dual energy x-ray absorptiometry), fat mass, bone mass are determined by DEXA and performance effects are analyzed, for example effects on exercise. Adverse effects are determined, e.g. via measuring liver transaminase levels, such as ALT and AST. Circulating cholesterol, LDL, VLDL, triglyceride and HDL levels are analyzed, as well. SHBG, testosterone, FSH and LH effects are determined as well, by standard methodology.

Example 6

Reduction of Glucose and Insulin Levels

Similarly, human clinical trials are conducted on elderly men (age>60) and postmenopausal women in a randomized, double-blind study design. Each subject receives the compounds of Example 2 or placebo of equal volume in solution or in experimental capsules for 90 days treatment.

Total circulating insulin and glucose levels at baseline and post-administration are determined.

Example 7

Metabolism of Compounds I and II

Methods

A. Metabolism of Compound I in Rats:

In vivo metabolite identification was performed in intact and bile duct cannulated male and female Sprague Dawley rats which received a radiolabeled single oral or intravenous dose of Compound I at 10 mg/kg. Urine and feces were collected over nine time intervals from intact animals, including pre-dose and 168 hours post dose. Urine, feces and bile were collected over six intervals from bile duct cannulated animals from pre-dose and 96 hours post dose. In addition, plasma samples were collected in 2 groups with either jugular vein catheter or femoral and jugular vein cathethers, dosed oral and intravenously, respectively. Plasma samples were collected at eight time points from pre-dose to 24 hours post dose. Plasma, urine and fecal samples were prepared.

Sample Preparation for In Vivo Metabolite Identification

Plasma samples were prepared by protein precipitation using organic solvents. After centrifugation, the supernatant was transferred and evaporated under a nitrogen stream, and the residues were reconstituted in the HPLC mobile phase for analysis. Fecal samples were extracted with the appropriate organic solvent repeatedly until greater than 80% radioactivity was recovered by extraction. The supernatants were combined and evaporated under a nitrogen stream. The residues were reconstituted in HPLC mobile phase for analysis. Urine and bile samples were analyzed directly after centrifugation, or in some cases concentrated by lyophilization before being reconstituted in HPLC mobile phase for analysis.

Metabolite Profiling

Metabolite profiling was carried out using radio flow-through detector (RFD) in-line with HPLC/MS to separate the metabolites of Compound I present in plasma, urine, and feces. Within each group, individual samples of plasma, urine, and feces from different intervals or timepoints within the same matrix were pooled. One pooled sample was generated for each matrix and each pooled sample represented minimally 85% of the total radioactivity in that matrix. Metabolites were extracted from plasma and feces. Extraction efficiency of plasma and fecal samples was determined (80% extraction efficiency was deemed the minimum required to proceed with profiling). Pooled plasma, urine, bile and feces samples were analyzed using HPLC/MS/RFD. Representative HPLC/MS/RFD chromatograms are shown in FIGS. 6-16.

Metabolite Identification

Metabolite identification was carried out using LC-MS/MS for analysis. An initial MS/MS experiment was performed on an authentic reference standard (parent drug) and any available reference metabolite standards and analogues to check for possible common fragment ions. A representative sample from each matrix with the highest amount of radioactivity was used for metabolite identification. Where necessary, the individual sample was pooled appropriately for metabolite identification. The molecular weight of the major metabolites (representing ≧5% of the radioactivity in the sample) was determined using LC/MS with different ionization modes and scanning methods (precursor ion scan and neutral loss scan). When available, authentic standards of the metabolites were used to confirm the molecular weight of the metabolite. For all metabolites representing ≧5% of the radioactivity in the sample appropriate tandem MS experiments (MS/MS or MS/MS/MS) were performed. Product ion spectra of the metabolites were interpreted and the structure of the metabolites was proposed. Fragmentation patterns of the proposed metabolites were analyzed. Where available, identification of the metabolites based on LC/MS/MS analysis was confirmed by comparing the product ion spectra and retention times of authentic reference standards.

Results

Metabolites of Compound I identified in vivo in Rat plasma, urine, feces and bile is provided in Table 9.

TABLE 9

In vivo Metabolites of Compound Identified In Rat Plasma, Urine, Feces or Bile

| Metabolite | Modification | $[M - H]^-$ | Retention Time (min) | Type |
|---|---|---|---|---|
| n/a | none (parent drug) | 388 | 20.4 | plasma |
| I | glucuronide | 564 | 15.5 | Bile |
| II | hydroxyl + glucuronide | 580 | 14.1 | Bile |
| III | monohydroxylation | 404 | 19.3 | Urine |
| IV | hydroxyl + sulfate | 484 | 17.1 | Urine |

Figure 17:
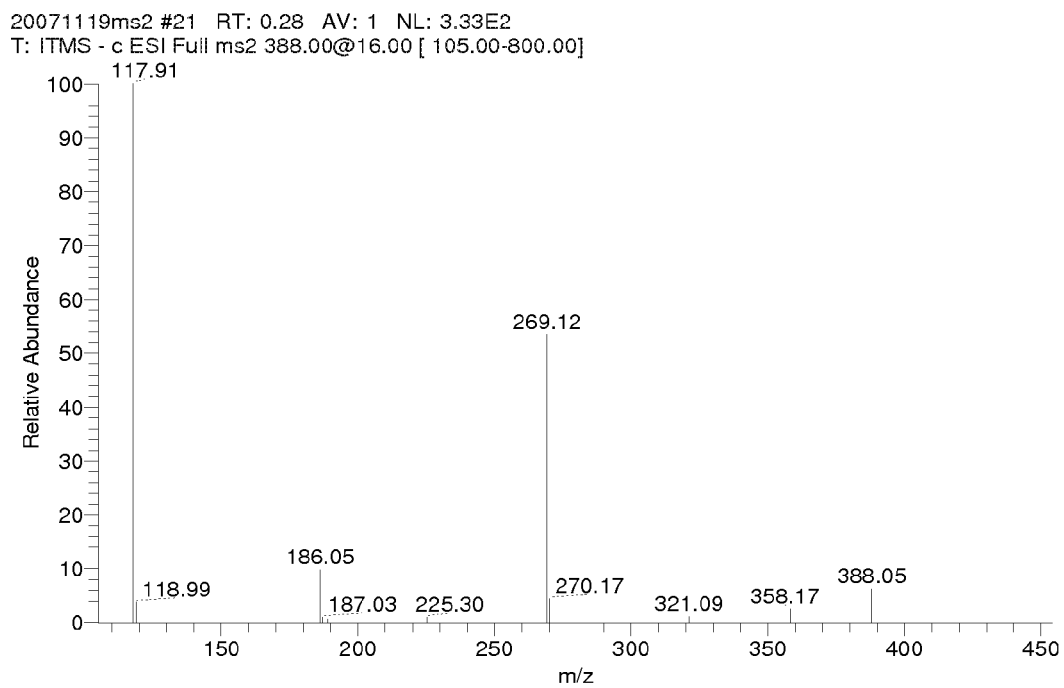
FIG. 17 depicts the product ion spectrum for Compound I authentic standard (m/z=388 in negative ion mode [M−H]⁻.
Figure 18:
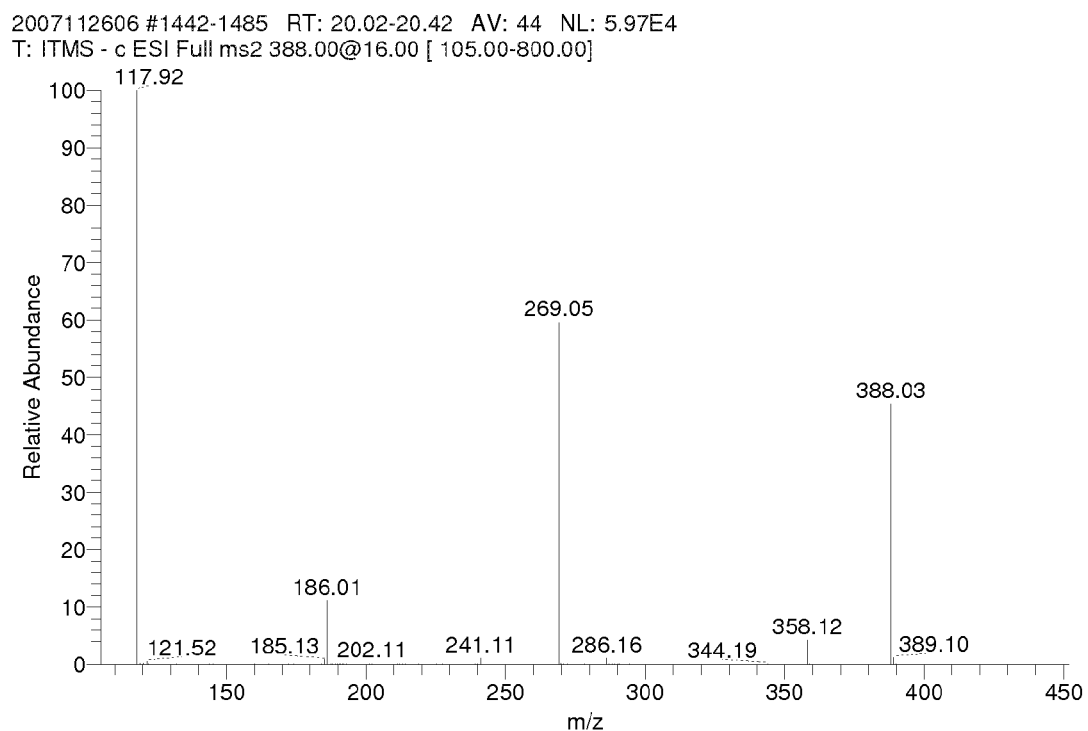
FIG. 18 depicts the product ion spectrum for Compound I in rat plasma. Peak at 20.4 min. retention time m/z=388 in negative ion mode [M−H]⁻.
Figure 24:
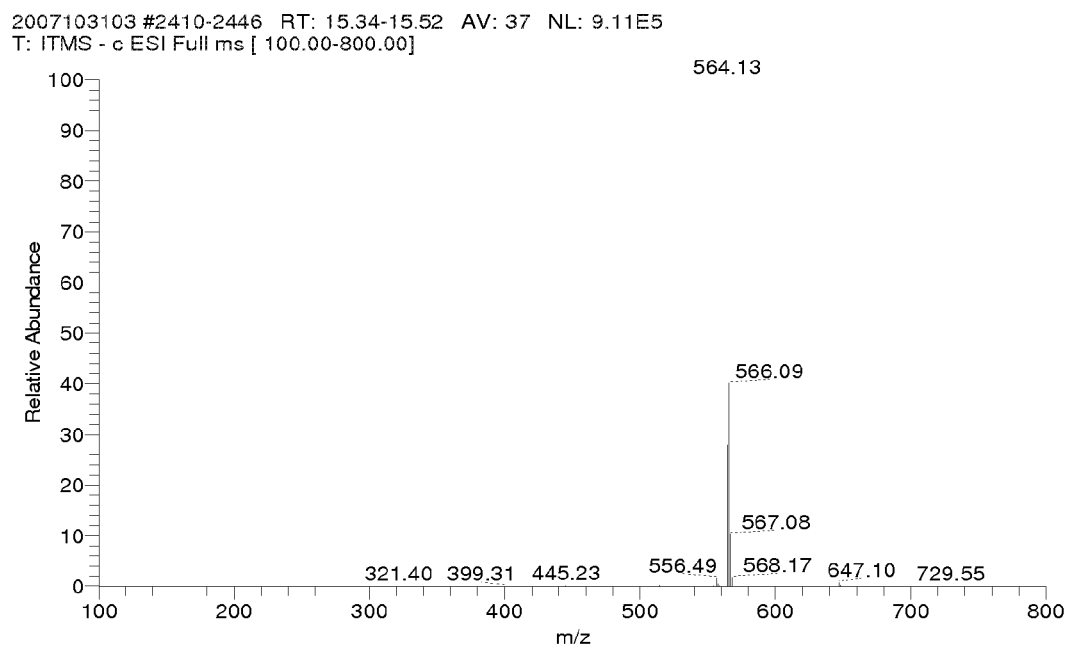
FIG. 24 depicts the mass spectrum of the peak at 15.5 min. retention time in rat urine and bile for Compound I metabolite I. m/z=564 in negative ion mode [M–H]⁻.
Figure 25:
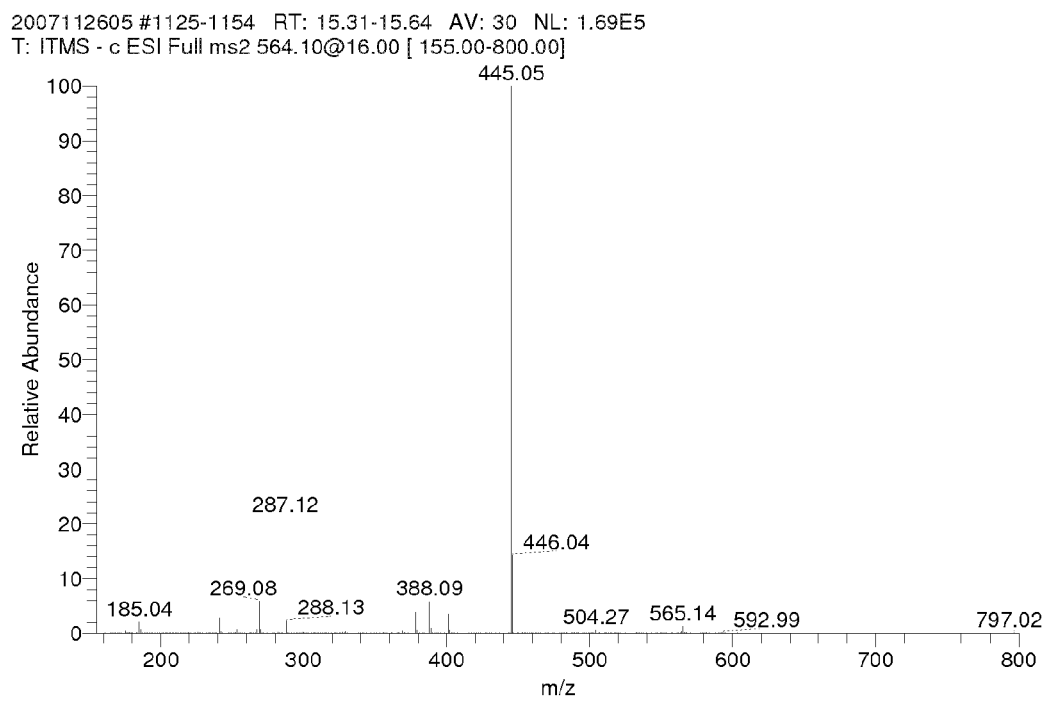
FIG. 25 depicts the product ion spectrum for Compound I metabolite I in rat urine and bile. m/z=564 in negative ion mode [M–H]⁻. Peak at 15.5 min. retention time.

Unchanged Compound I was identified in rat plasma as the major circulating component, as demonstrated in the radiochromatograms of FIGS. 6-9. The product ion spectra for Compound I as an authentic standard and in a rat plasma sample are shown in FIGS. 17 and 18, respectively. Compound I was apparently increased in plasma concentration with intravenous versus oral dose (increased CPM in FIGS. 8 and 9 versus 6 and 7). There were little or no detectable plasma metabolites of Compound I in the male or female rat after either an oral or intravenous dose of Compound I. Following oral administration of Compound I to male rats bearing a bile duct cannula, the major metabolites identified in the bile fraction were glucuronidated products. FIG. 24 demonstrates the mass spectrum for the peak with a retention time of ~15.5 minutes in the radiochromatogram from rat bile. FIG. 24 indicates a mass to charge ratio of 564 for this metabolite. FIG. 25 is consistent with the addition of 176 mass units where the product ion spectrum supports a glucuronide product of Compound I as Metabolite I.

Figure 26:
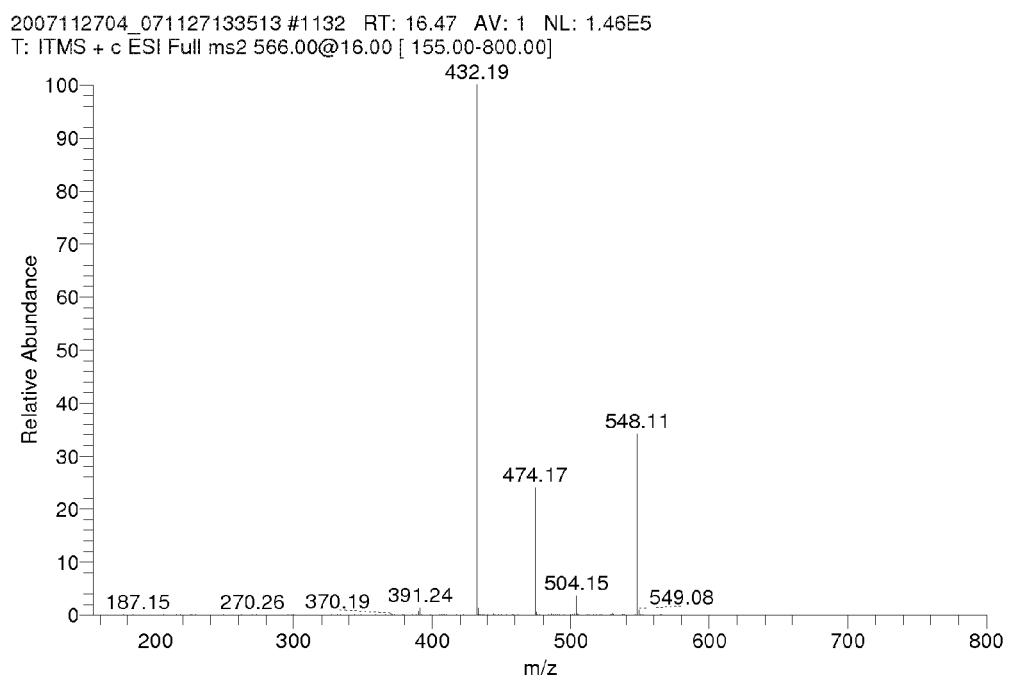
FIG. 26 depicts the product ion spectrum for Compound I metabolite I in rat urine and bile. m/z=566 in positive ion mode [M+H]⁺. Peak at 15.5 min. retention time.

Further analysis using MS/MS/MS suggests the glucuronide modification occurs on the hydroxyl group of the chiral center as demonstrated by FIG. 26.

Figure 27:
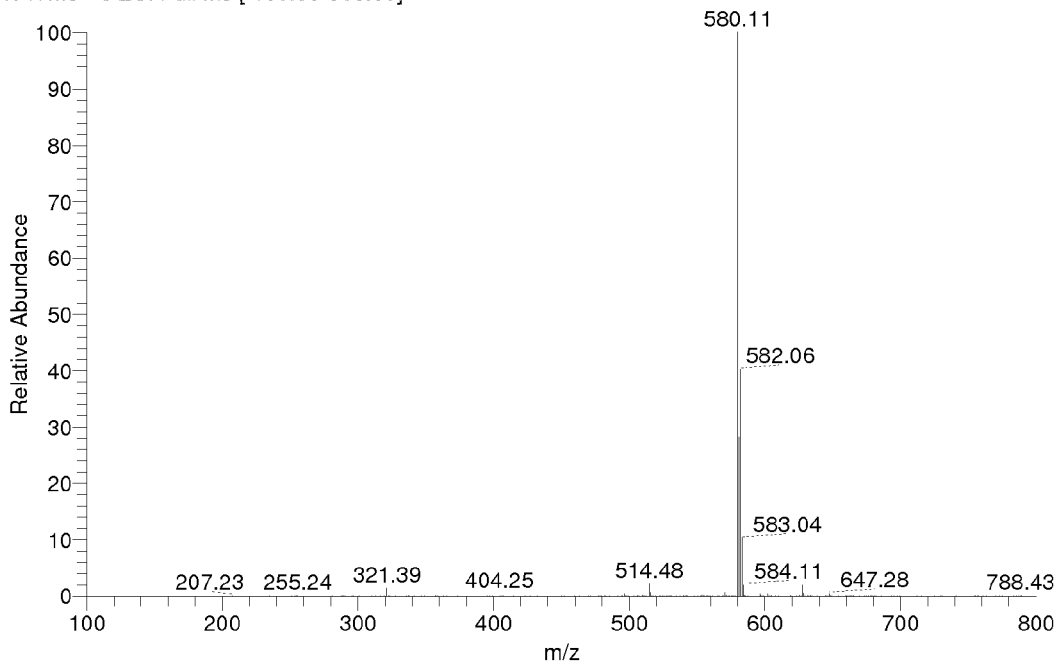
FIG. 27 depicts the mass spectrum of the peak retention time in rat bile for Compound I metabolite II. m/z=580 in negative ion mode [M–H]⁻. Peak at 14.1 min. retention time.
Figure 28:
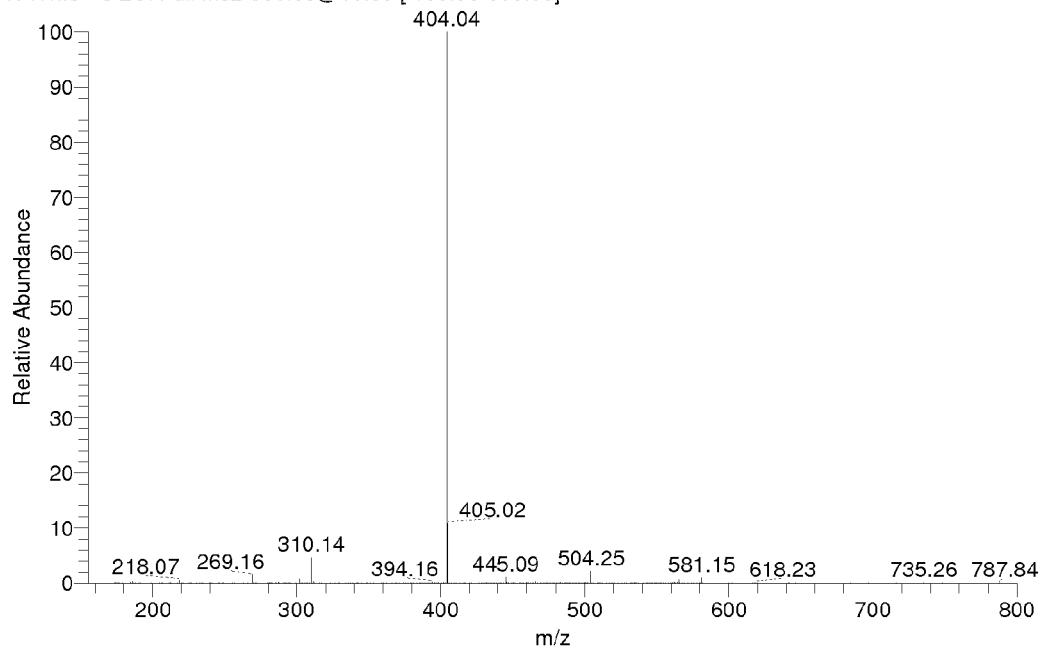
FIG. 28 depicts the product ion spectrum for Compound I metabolite II in rat bile. m/z=580 in negative ion mode [M–H]⁻. Peak at 14.1 min. retention time.
Figure 29:
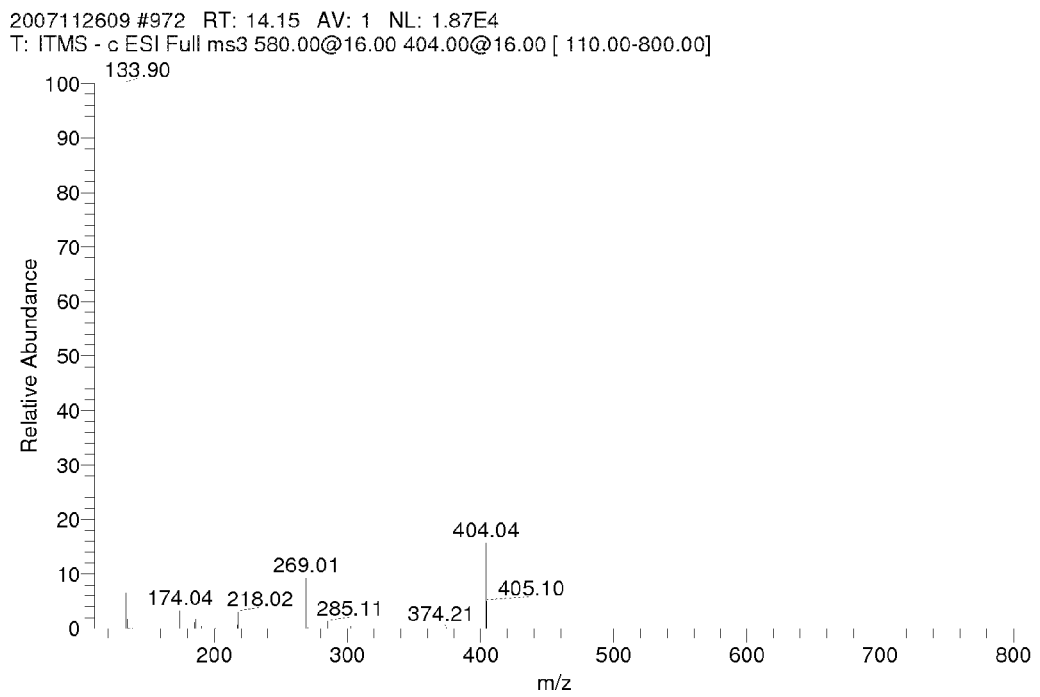
FIG. 29 depicts the product ion spectrum Compound I metabolite II in rat bile. m/z 580→404 in negative ion mode [M–H]⁻.
Figure 30:
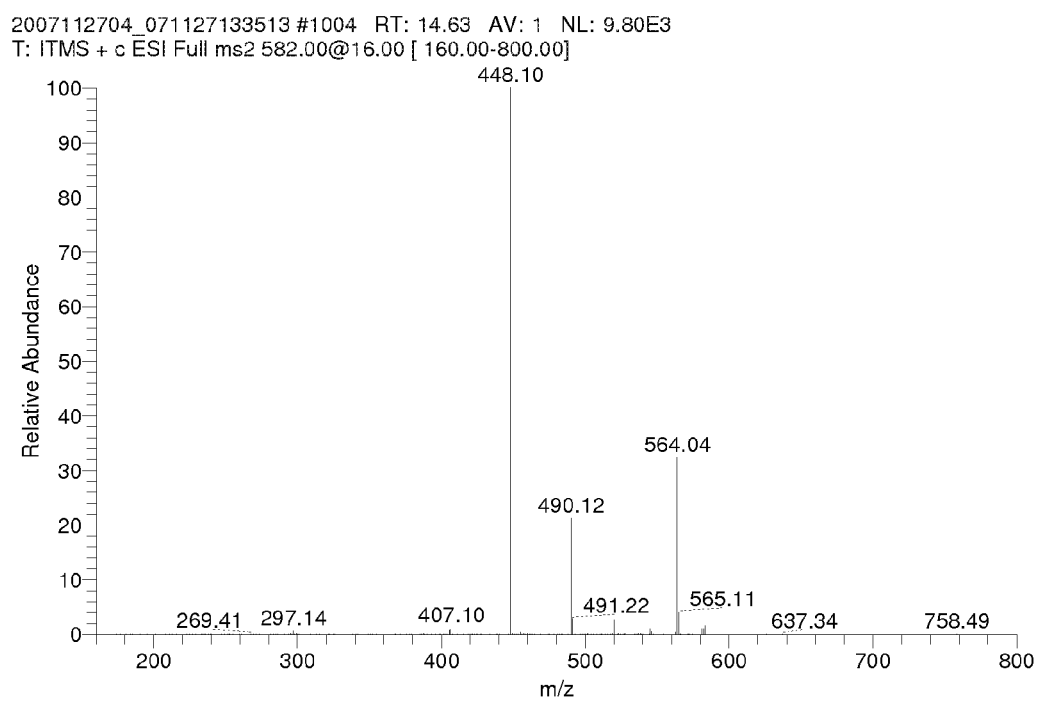
FIG. 30 depicts the product ion spectrum for Compound I metabolite II in rat bile. m/z=582 in positive ion mode [M+H]⁺. Peak at 14.1 min. retention time.

FIG. 27 demonstrates that another glucuronidated product was apparent in bile with a retention time of 14.1 minutes. FIG. 27 shows the mass spectrum of this metabolite as m/z 580, consistent with a glucuronide conjugate of a monohydroxylated Compound I metabolite. The product ion spectra demonstrated in FIGS. 28-30 suggest this modification occurs on the cyanophenol moiety (i.e. b-ring) of the Compound I structure.

Figure 21:
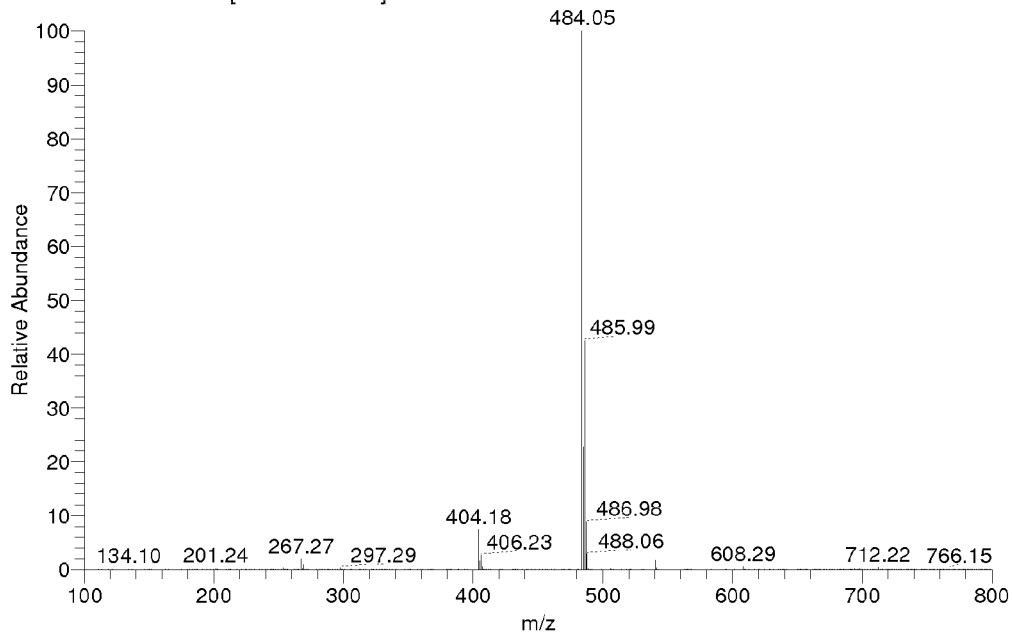
FIG. 21 depicts the mass spectrum of the (minor) peak at 17.7 min retention time in rat urine for Compound I metabolite IV. m/z=484 in negative ion mode [M–H]⁻.
Figure 22:
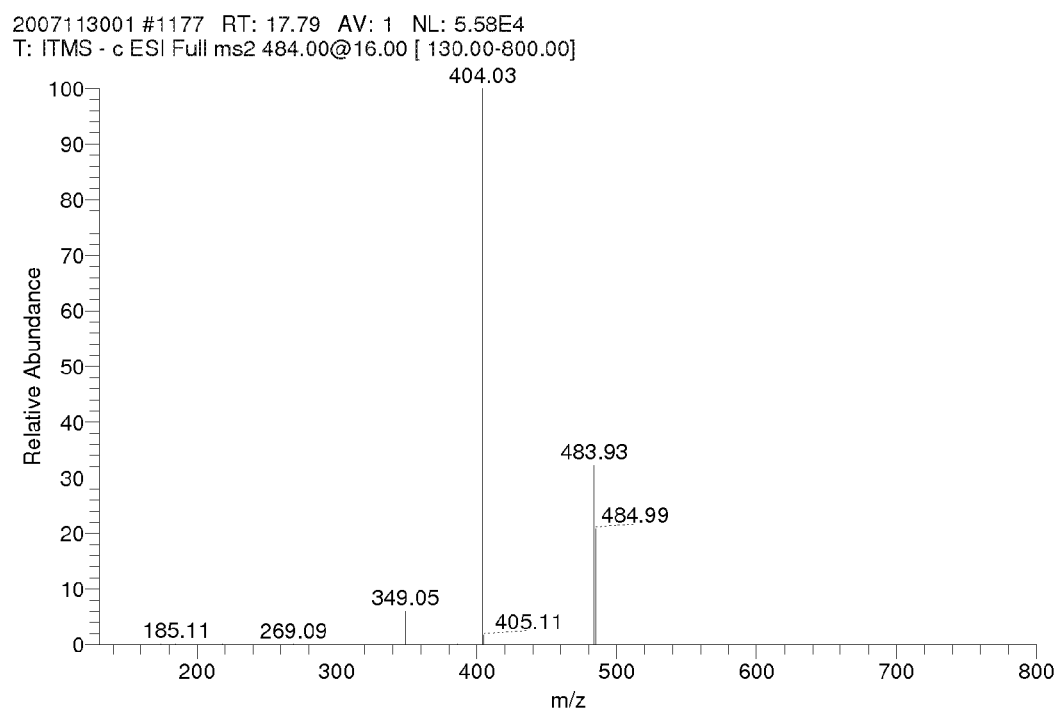
FIG. 22 depicts the product ion spectrum for Compound I metabolite IV in rat plasma. m/z=388 in negative ion mode [M–H]⁻.
Figure 23:
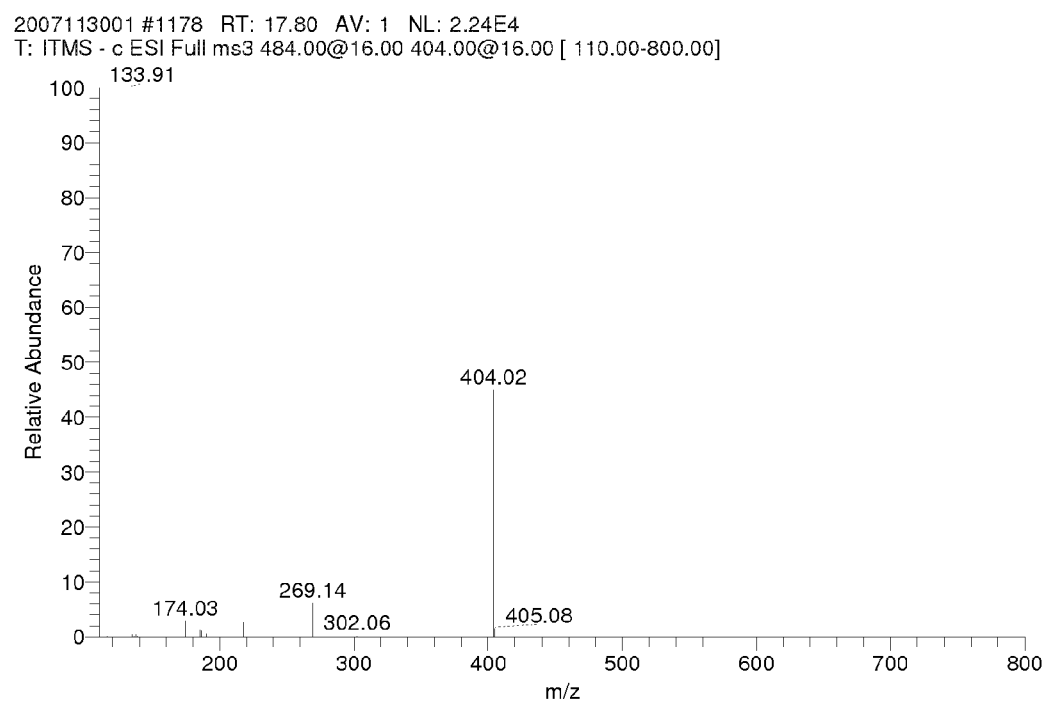
FIG. 23 depicts the product ion spectrum for Compound I metabolite IV in rat urine. m/z 484→404 in negative ion mode [M–H]⁻.

Several metabolites were apparent in the pooled urine of rats dosed orally with Compound I, however, since they were low in abundance (i.e., represented less than 1.5% of the administered oral dose by semi-quantitative analysis) most were not identified. Although it was not evident in the HPLC/MS/RFD chromatogram for the urine sample of rats, when the urine sample was concentrated prior to analysis, a very minor metabolite was identified in urine. FIG. 21 shows the mass spectrum which indicates the mass to charge ratio for Metabolite IV is 484. The product ion spectrum shows a fragment consistent with the monohydroxy Compound I (m/z 404) and the metabolite was tentatively identified as the sulfated conjugate of monohydroxyl Compound I. Further analysis by MS/MS/MS, performed in negative ion mode, demonstrates in FIG. 23 fragments of m/z 404, 270 and 134 which suggest the O-sulfate modification of Metabolite IV occurs on the cyanophenol moiety (i.e. b-ring) of Compound I.

Figure 14:
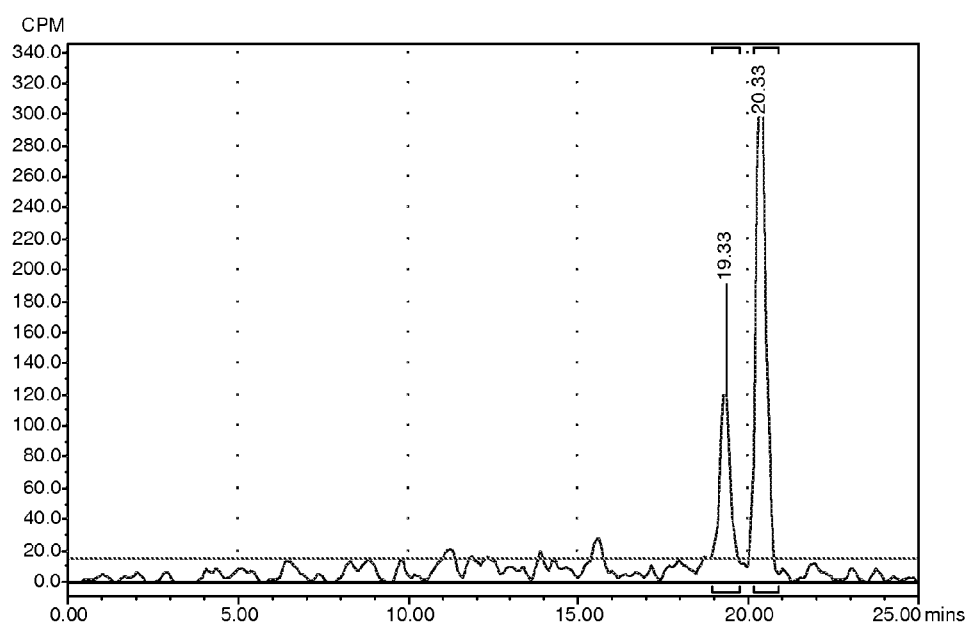
FIG. 14 depicts a radiochromatogram of sample from Fecal-Pool 1 (Intact Male) following oral administration of Compound I to male Sprague Dawley rats.
Figure 15:
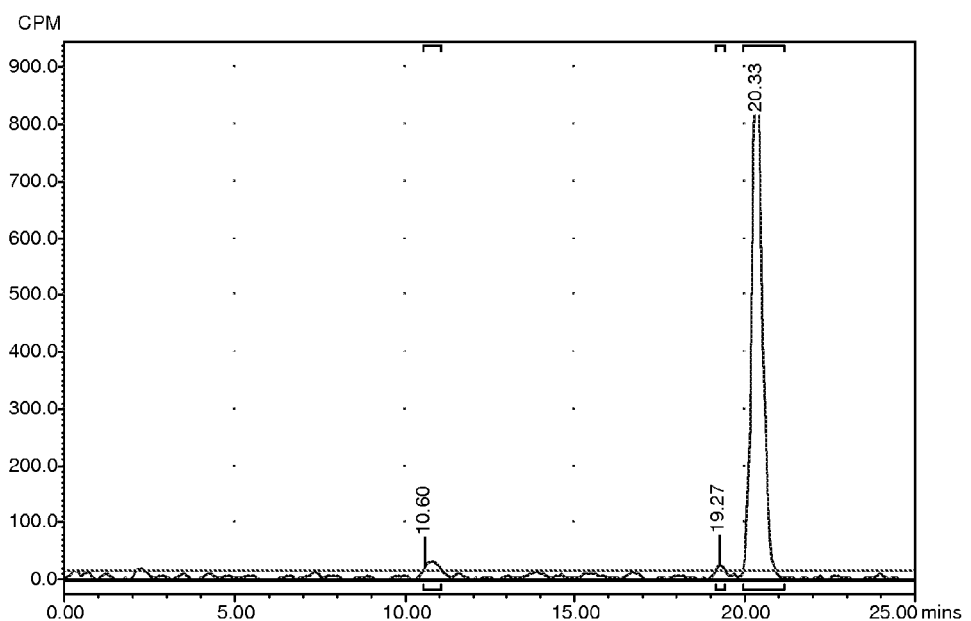
FIG. 15 depicts a radiochromatogram of sample from fecal-Pool 2 (Intact Female) following oral administration of Compound I to female Sprague Dawley rats.
Figure 19:
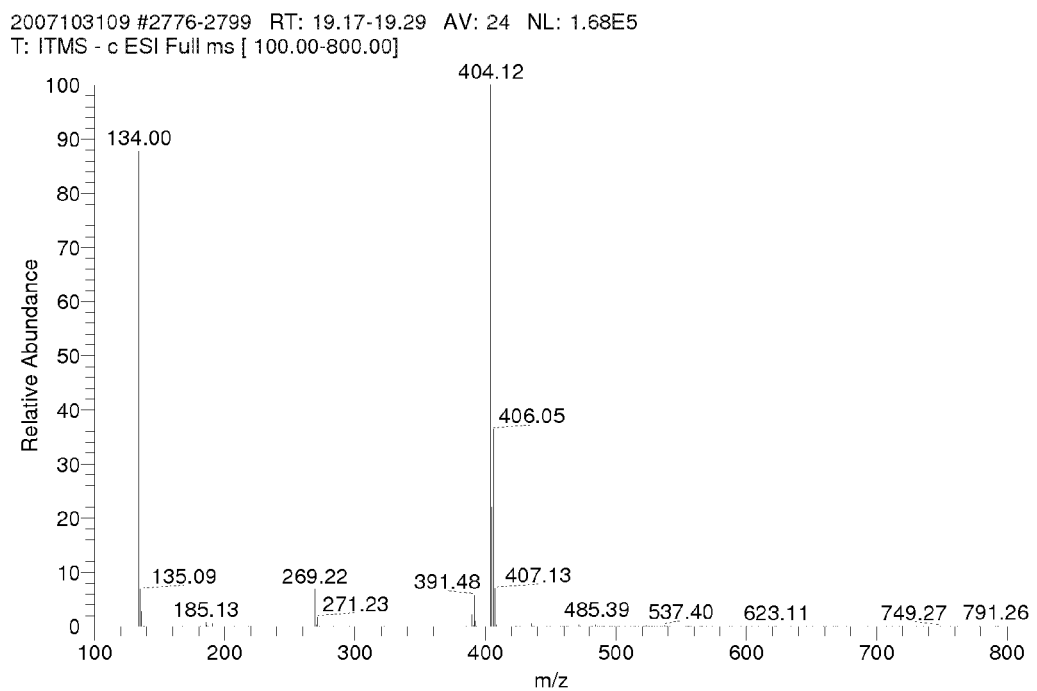
FIG. 19 depicts the mass spectrum of the peak at 19.3 min retention time in rat plasma for Compound I metabolite III. m/z=404 in negative ion mode [M−H]⁻.
Figure 20:
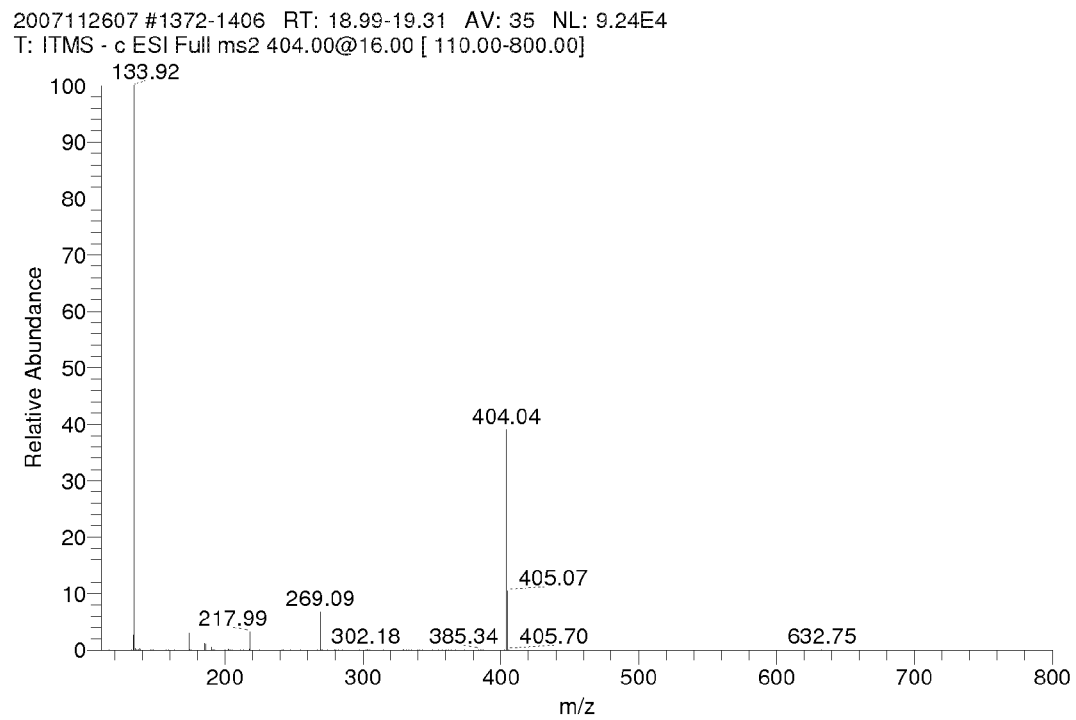
FIG. 20 depicts the product ion spectrum for Compound I metabolite III. m/z=404 in negative ion mode [M−H]⁻.

The major Compound I-related radioactivity in fecal samples of intact male and female rats was associated with excreted unchanged Compound I. There was an additional metabolite identified in feces of intact rats with retention time of 19.3 minutes (FIGS. 14 and 15). The mass spectrum of the peak at 19.3 minutes shows a molecular ion of m/z 404 for Metabolite III (FIG. 19). Further analysis reveals in FIG. 20, that this metabolite is a monohydroxy product of Compound I with the addition of OH group on the cyanophenol moiety of the compound.

Figure 16:
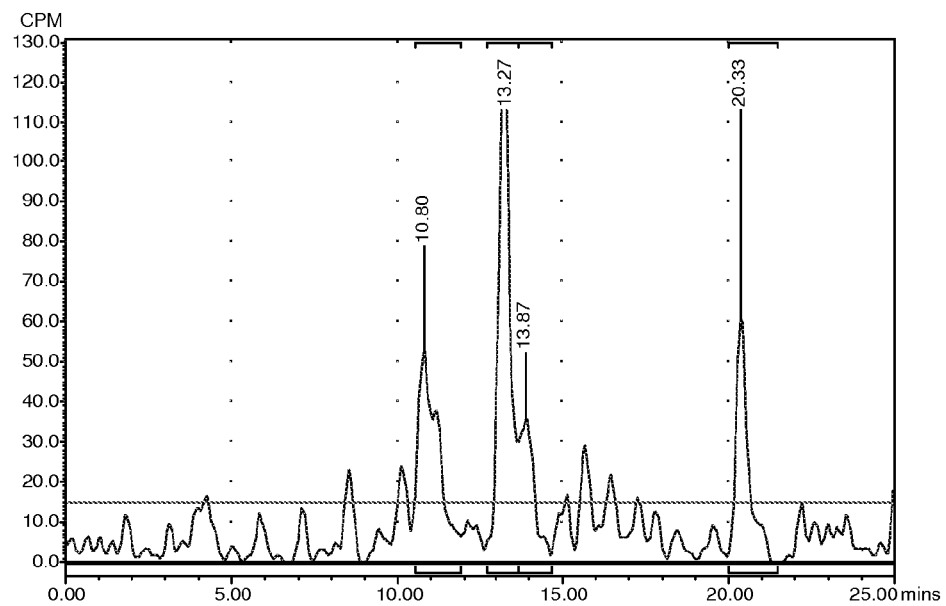
FIG. 16 depicts a radiochromatogram of sample from fecal-Pool 3 (BDC Male) following oral administration of Compound I to male Sprague Dawley rats.

FIG. 16 demonstrates that the analysis of fecal metabolites from bile duct cannulated rats revealed a different profile. In these rats, unchanged Compound I was present at a greatly reduced level and monohydroxy of Compound I was undetectable.

The other minor metabolites at retention time of 13.3 and 10.8 were proportionally more significant in the feces of bile duct cannulated rats, but generally they were not present at a higher level than intact rats.

The overall pattern of metabolites identified in rats is consistent with those predicted from in vitro incubations with rat liver microsomes and hepatocytes.

Figure 44:
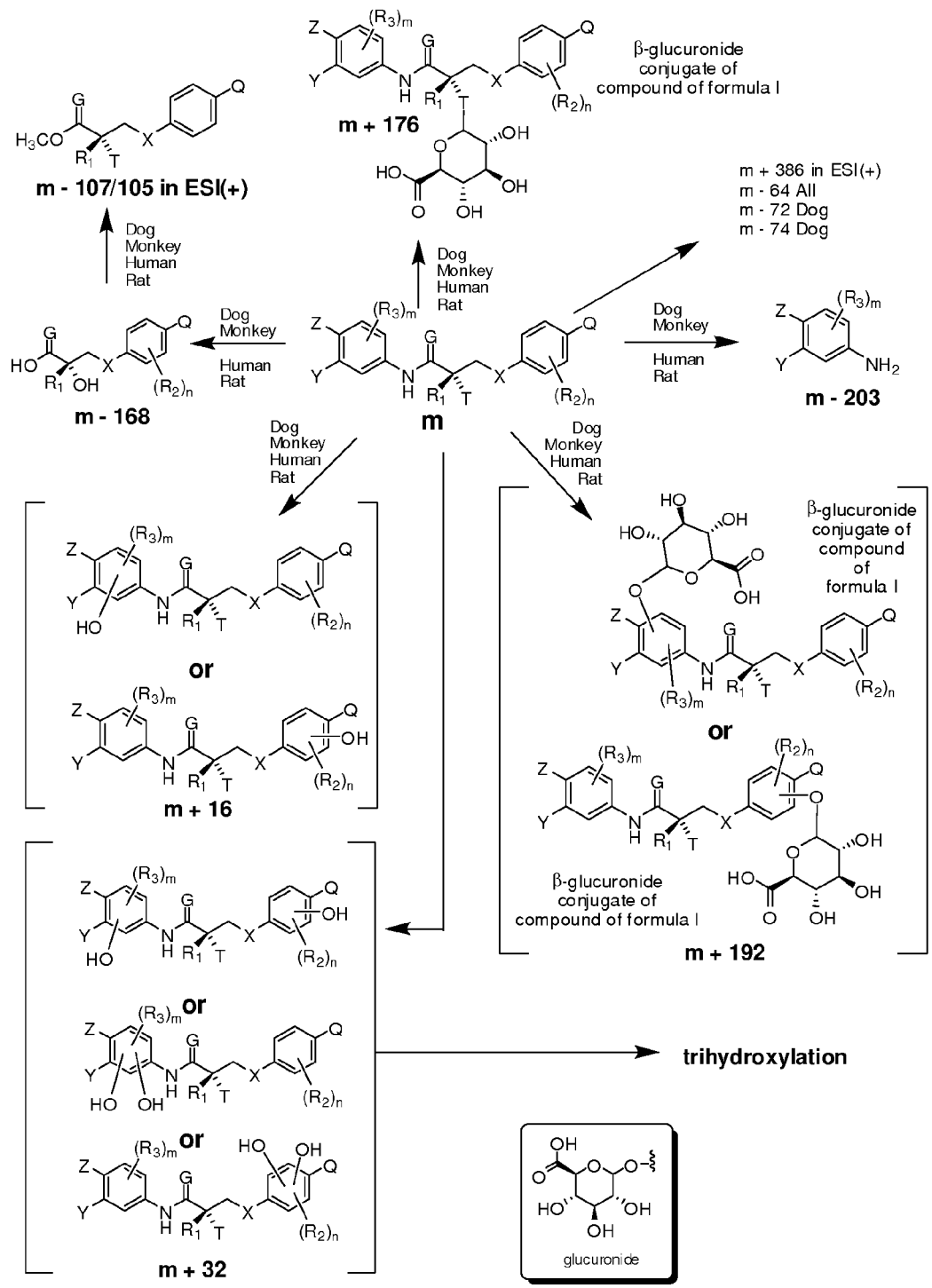
FIG. 44 schematically depicts a metabolic pathway of compounds I-IV from in vitro (rat, human, dog, monkey and mouse microsomes and hepatocytes) and in vivo (rat and dog) studies.
Figure 44:
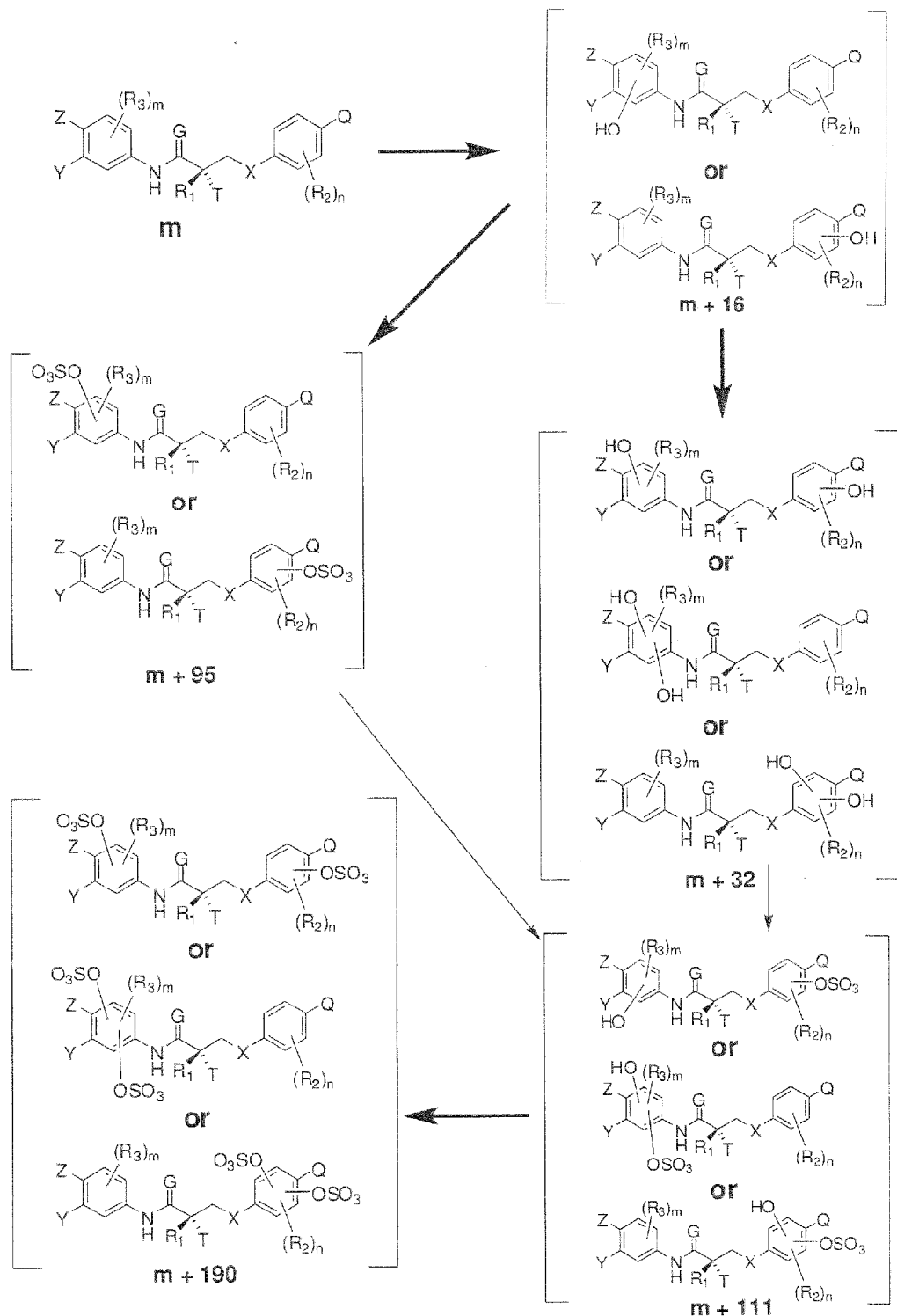
Figure 45A:
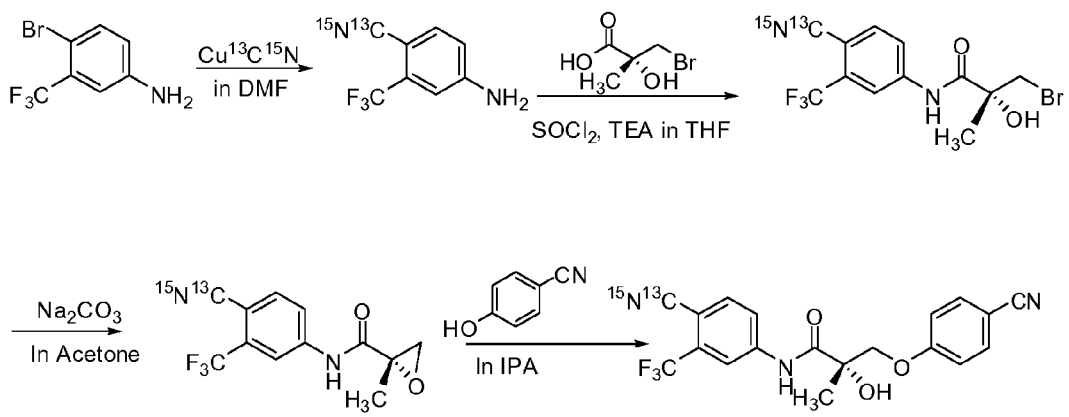
FIG. 45A depicts the synthesis of $^{15}N^{13}C$ labeled A-ring for Compound I.
Figure 45B:
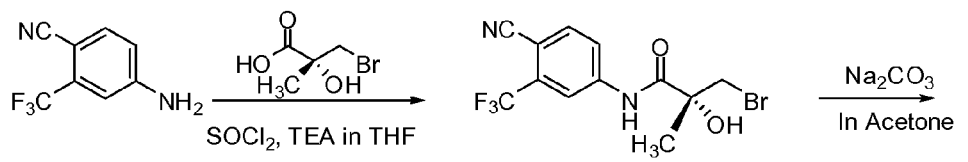
FIG. 45B depicts the synthesis of deuterium labeled B-ring for Compound I.
Figure 45C:
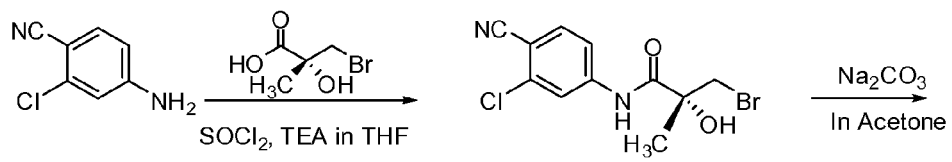
FIG. 45C depicts the synthesis of deuterium labeled B-ring for Compound II.
Figure 45D:
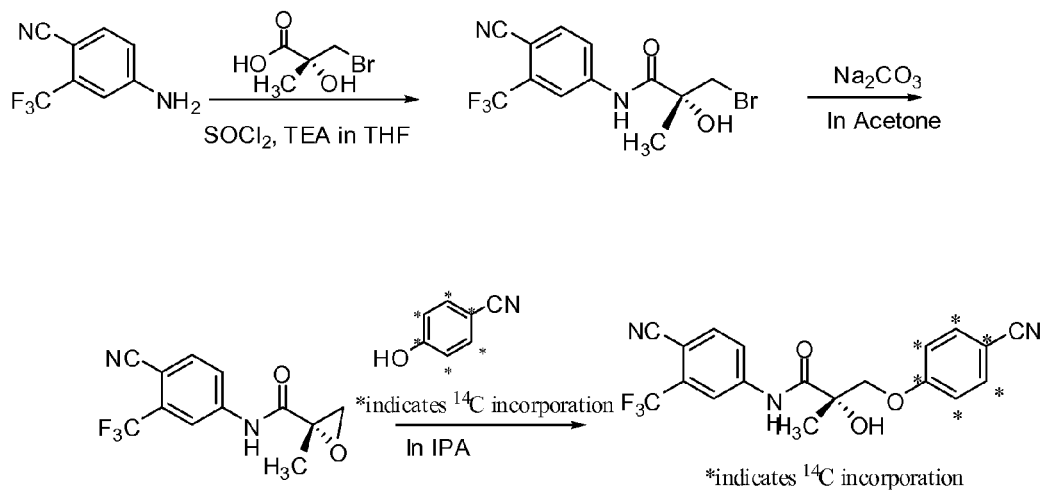
FIG. 45D depicts the synthesis of $^{14}C$ labeled B-ring for Compounds I.
Figure 45E:
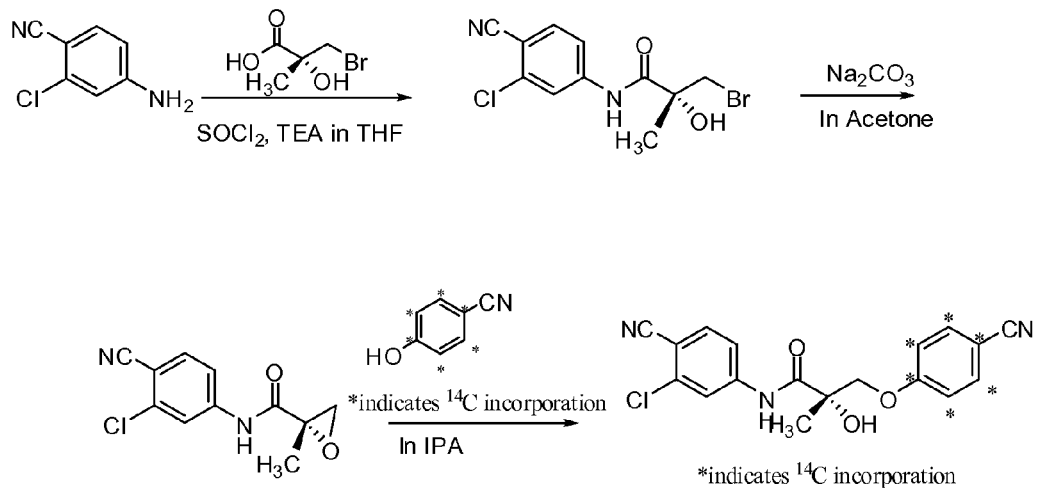
FIG. 45E depicts the synthesis of $^{14}C$ labeled B-ring for Compounds II.

The overview of possible biotransformations for SARMs is proposed in FIG. 44.

In Vitro Metabolite Identification from Human, Monkey, Dog, Rat and Mouse Liver Microsomes and Hepatocytes Methods Experiments were performed to analyze the Phase I and Phase II metabolites of SARMs generated by in vitro incubations with liver microsomes and hepatocytes from various species of interest. Generally, incubations were performed as described below and analyzed by LC-MS/MS and MS/MS/MS to determine the in vitro metabolic profile of SARMs and to identify metabolites likely to be formed in vivo after dosing humans or other species with SARMs.

Materials and Reagents

SARMs were synthesized at GTx, Inc. Human, monkey, dog, rat, and mouse liver microsomes (Lot # 0710091, 0610022, 0610048, 0510153, and 0710105, respectively) were purchased from Xenotech, LLC. Solution 'A' and 'B' for NADPH regenerating system (NRS) solution were obtained from BD Biosciences (Waltham, Mass.). Hepatocyte incubation media and supplemented DMEM with and without Percoll were purchased from Xenotech (Cat. # K2500). Verapamil, genistein, tamoxifen, and diclofenac, UDPGA, and saccharolactone were purchased from Sigma-Aldrich.

Phase I Microsome Reactions

Test compound stock solutions were prepared in acetonitrile at 10 mM, 200 times (200×) the final concentration. The stock solutions were added in incubation mixtures to obtain the final drug concentration of 50 μM, containing 0.5% acetonitrile. A concentration of 50 μM was utilized to allow for detection of possible minor metabolites (select studies were run at 10 μM for confirmatory purposes). Human, monkey, dog, rat, mouse microsomes were all utilized at a final concentration of 1.0 mg/ml. Duplicate wells were used for each time point (0 and 120 minutes). Incubation was conducted at 37° C. in a shaking water bath. The final volume for each reaction was 200 μl, composed of: 66 μl of 0.2 M $KPO_4$ buffer, (pH 7.4); 73 μl of $H_2O$, 10 μl of 20 mg/ml microsome stock; 1.0 μl of 10 mM compound stock, and 50 μl of NRS solution. The NRS solution consisting of glucose-6-phosphate dehydrogenase, NADP+, $MgCl_2$, and glucose-6-phosphate, was prepared as described in manufacturer's instructions.

Phase I and II Microsome Reactions

For microsome reactions performed under conditions allowing for both phase I and II metabolism, the initial procedure and reaction conditions were followed similarly as described above. Additional cofactors were also included in each reaction to maximize the potential for in vitro glucuronidation to occur. UDPGA was added at a final concentration of 5.0 mM. Saccharolactone (β-glucuronidase inhibitor) and alamethicin (pore forming peptide) were added to each reaction at a final concentration of 5.0 mM and 50 μg/ml, respectively.

Each 200 μl microsomal reaction solution was composed of: 66 μl of 0.2 M $KPO_4$ buffer, (pH 7.4); 50 μl of NRS solution (as described above); 66 μl of UDPGA (15 mM stock); 5.0 μl of saccharolactone (200 mM stock); 0.5 μl of alamethicin (20 mg/ml); 0.6 μl of $MgCl_2$ (1 M stock); and 10 μl of microsomes (20 mg/ml stock).

Termination of Phase I and II Microsome Reactions

At the end of incubation, 100 μl of reaction solution under incubation was transferred to a sample well containing 100 μl of ice cold acetonitrile to quench the reaction. The reaction from the positive control wells (verapamil, 0.5 μM) for phase I metabolism were stopped with ice cold acetonitrile containing 0.1 μM tamoxifen and 0.1 μM diclofenac. Samples were then centrifuged at 3,000 rpm for 10 minutes at 4° C. to precipitate protein. Approximately 150 μl of supernatant was subsequently transferred to a new sample block for LC/MS/MS analysis.

Hepatocyte Assay

The stock solutions (10 mM in acetonitrile) for the test compounds were diluted in the incubation media to a working concentration of 100 μM (2×). Thawing frozen hepatocytes was followed by performing Percoll purification as described in manufacturer's manual. Primary hepatocytes were resuspended in incubation media and viability was measured using trypan blue exclusion method. The initial viability score was registered as 'T0' (time point of 0 minute), and viability was required to be at least ~70% at this point for the experiment to continue. Cells were washed a second time (60 g for 5 minutes) with supplemented DMEM and the final concentration was adjusted to $2 \times 10^{-6}$ cells/ml (2×). Samples were set up in 48-well plates, using 2 wells per each time point. A trypan blue well was also set up for viability analysis at the end of study (T=120 min). 100 μl of the 2× drug solution was combined with 100 μl of the 2× hepatocyte suspension. Final concentration was $1 \times 10^{-6}$ cells/ml (200,000 cells/well) and 50 μM compound. Final concentration of acetonitrile was 0.5%. Incubations were initiated by placing the plates in a humidified incubator set at 37° C. with an atmosphere of 5% $CO_2$. Timed intervals of 0 and 120 minutes were carried out. Incubations were terminated by the addition of 200 μl of ice-cold acetonitrile. For sample analysis, quenched reactions were vortexed, and precipitated protein was removed by centrifugation (2100 g for 5 minutes at room temperature). The supernatant fraction was transferred to a new well plate and stored at −80° C. until LC/MS/MS analysis was performed. Slight modifications to the procedures above were made following standard protocols for incubation of SARMs with cryopreserved hepatocytes of monkey, rat, dog, mouse and human.

LC-MS/MS Analysis

The analysis of metabolites was performed using a LC/MS/MS system consisting of Agilent 1100 HPLC with an MDS/Sciex 4000 Q-Trap™ mass spectrometer. The separation was achieved using an YMC™ ODS-AQ column (5 μm, 120 Å, 150×2.0 mm ID). Mobile phase was consisting of channel A (95% acetonitrile+5% water+0.1% formic acid) and channel B (95% water+5% acetonitrile+0.1% formic acid) and was delivered at a flow rate of 0.3 mL/min. The linear gradient of mobile phases was as follows: 0 min, 0% A; 3 min, 0% A; 21 min, 65% A; 25 min, 100% A; 27 min, 100% A; 28 min, 0% A. Enhanced MS (EMS) scan were made in Electrospray Ionization (ESI) negative mode with curtain gas at 30, collision gas at high, ion spray voltage at −4500 V, source temperature 500° C., nebulizer gas at 30, and Auxiliary gas at 40. Declustering potential and collision energy were set at −55 and −20, respectively. Scanned mass range of 100-650 m/z was conducted at a scan rate of 1000 amu/s, and a step size of 0.08 amu. Dynamic Fill Time was used for trap scans to ensure optimal ion trap fill times.

The mass spectrometers were operated in EMS mode in order to detect all possible metabolites. The total ion chromatogram (TIC) of 2 hr incubation sample was compared to TIC at time zero quenched controls in order to eliminate matrix and sample background signals. In order to confirm the presence of metabolites, distinctive extracted ion chromatogram (XIC) of 2 hr incubation sample and unique isotopic pattern of Cl-containing compound were used. Possible structure of metabolites was identified based on the fragmentation pattern of metabolites. Intensity of putative metabolite was semi-quantitated using the peak area of the metabolites in XIC, which was subtracted with the peak area of time zero control at the same retention time with the metabolites.

Results

Mammalian Metabolites of Compound II Identified In Vitro

The incubation of Compound II with human liver microsomes generated several distinct Phase I metabolites which were separated chromatographically.

Figure 31:
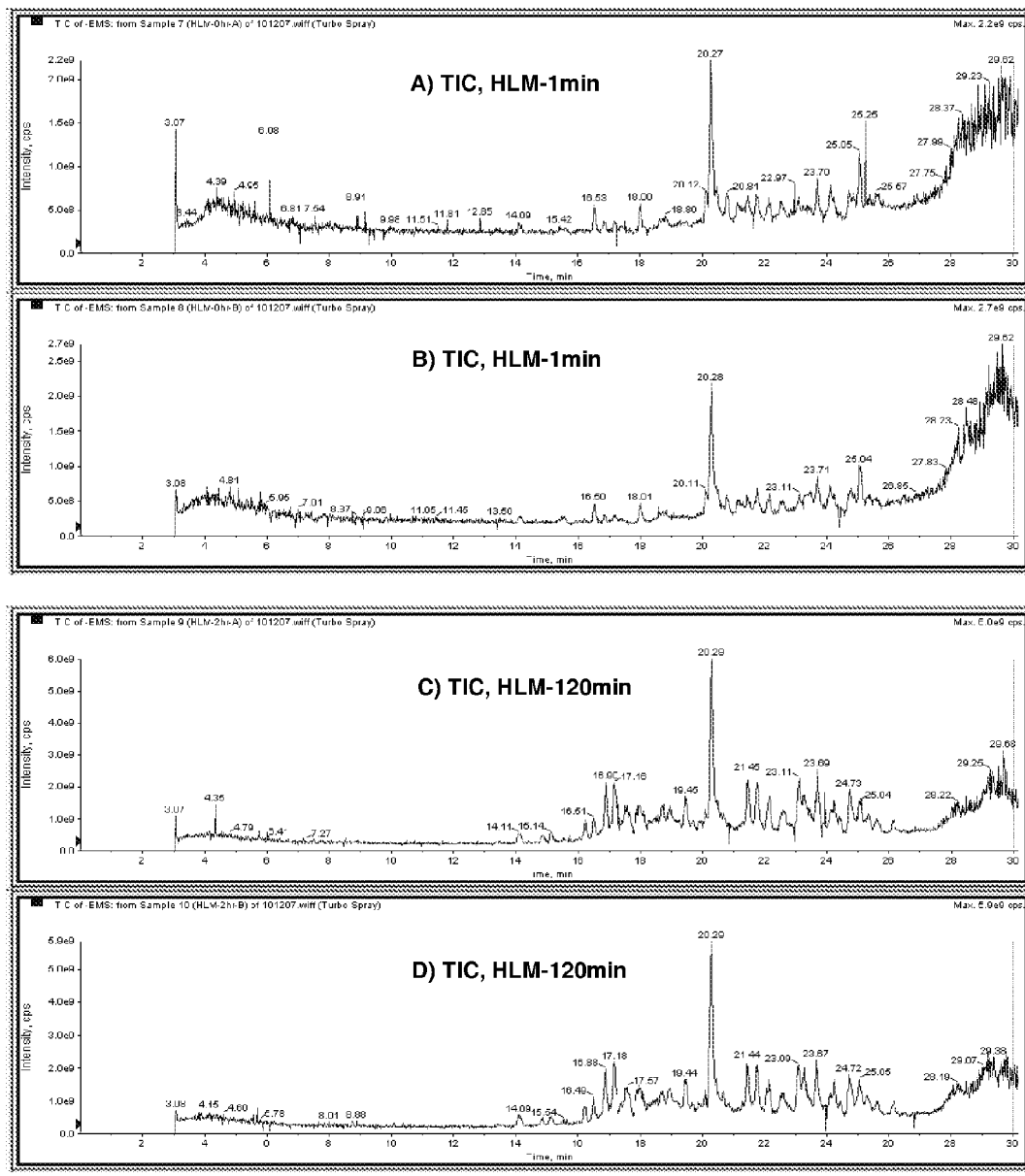
FIG. 31 depicts the total ion chromatogram (TIC) of (–) enhanced MS (EMS) of Compound II incubated in human liver microsomes (no UDPGA). The scale of the vertical axis is intensity (CPS). The scale of the horizontal axis is time (minutes).

FIG. 31 presents mass chromatograms for duplicate samples each from the incubation of human liver microsomes (HLM) with Compound II under conditions as stated previously. The top two panels, A and B, are total ion chromatograms (TIC) from the samples representing the initial incubation (HLM-1 min). The bottom panels, C and D, are TIC for samples after the 120 minute incubation was complete (HLM-120 min). Apparent in the TICs for the initial sample (i.e., HLM-1 min) as well as the final incubate (i.e., HLM-120 min), the peak with retention time of ~20.3 minutes is the unchanged fraction of Compound II. Metabolites of Compound II are indicated by the presence of new peaks or peaks of increased intensity in the mass chromatograms of the samples after 120 minute incubations compared to the initial samples.

Figure 32:
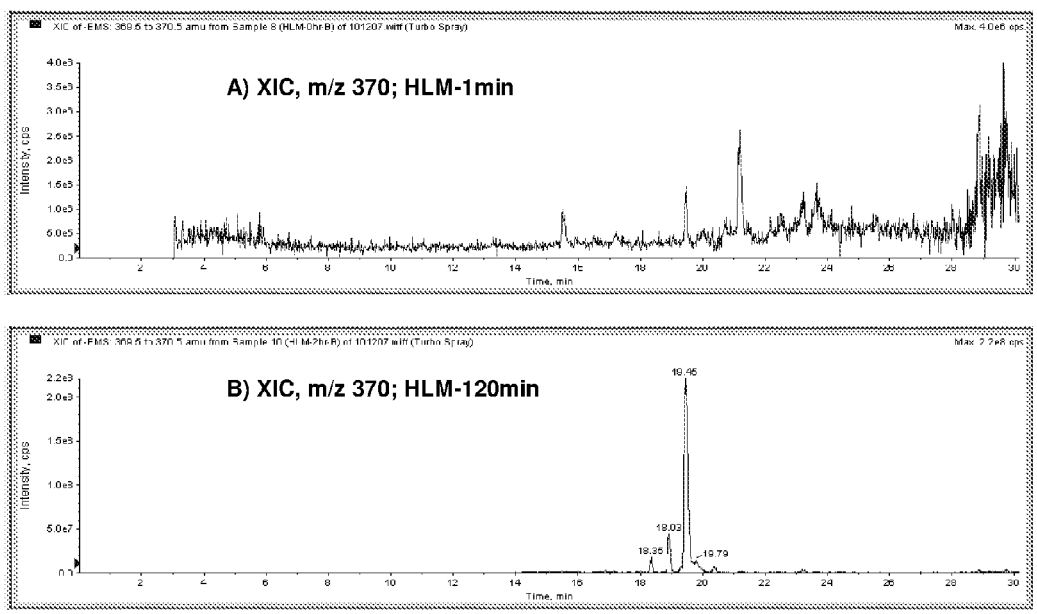
FIG. 32 depicts the extracted ion chromatogram (XIC) at m/z 370 of (–) enhanced MS (EMS) of Compound II incubated in human liver microsomes (no UDPGA). The scale of the vertical axis is intensity (CPS). The scale of the horizontal axis is time (minutes).

To select potential metabolites out of the total ion chromatograms, extracted ion chromatograms (XIC) were constructed from the TIC by plotting specific masses of interest for signal versus time. FIG. 32 displays the XIC for the ion at m/z 370 in the initial sample (panel A) versus the 120 min incubation (panel B). The m/z 370 ion represents [M−H]⁻ for the monohydroxylated metabolite of Compound II which is shown to be formed in the HLM incubation. FIG. 32 shows three distinct peaks in the XIC at retention time of ~18.4, 18.9 and 19.5 minutes, suggesting that at least three species of the monohydroxyl Compound II are formed.

Figure 33:
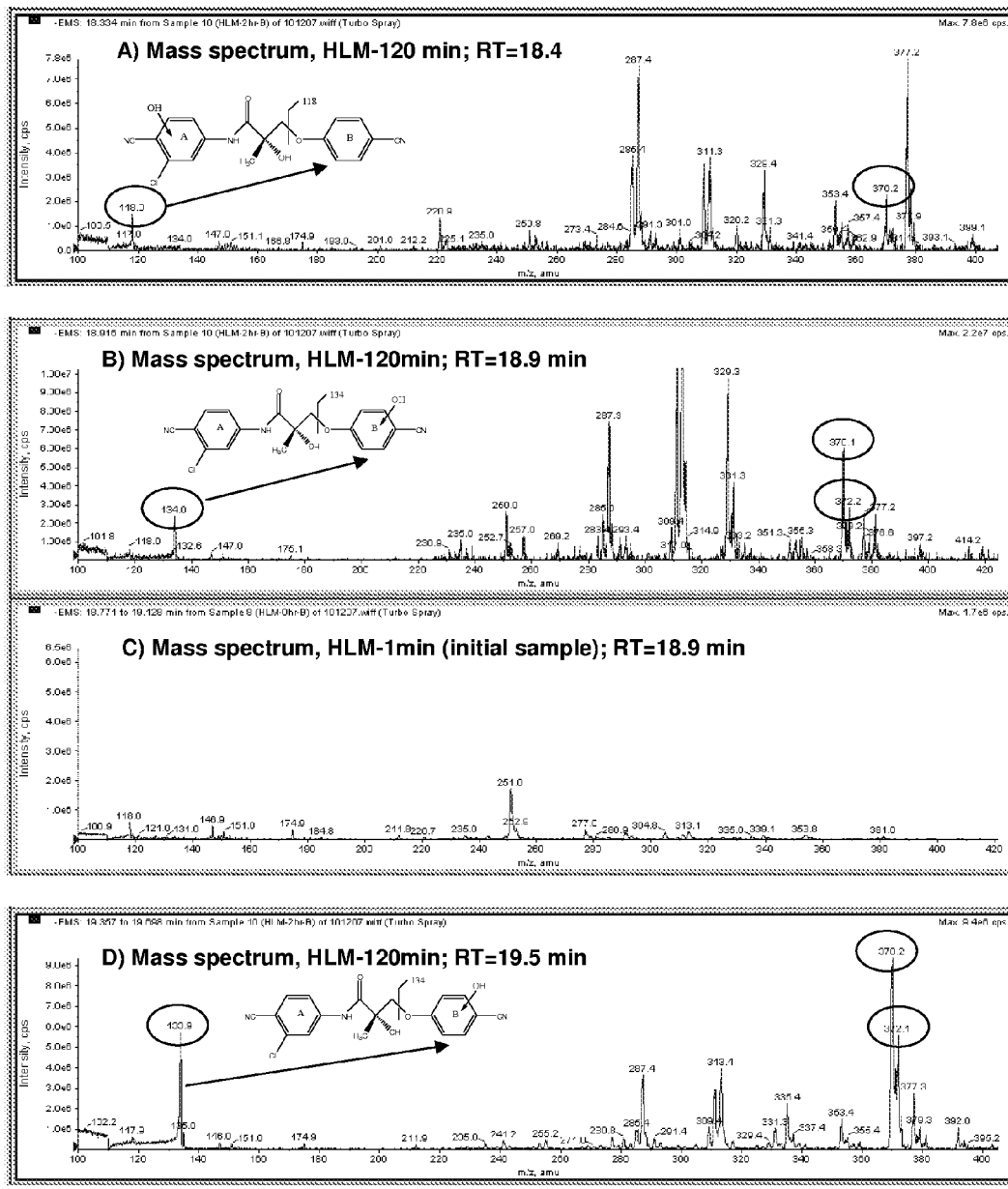
FIG. 33 depicts the mass spectra of mono-hydroxylated metabolite (negative ion mode, m/z 370) of Compound II at three different retention times (18.4, 18.9, and 19.5 min) in human liver microsomes. The scale of the vertical axis is intensity (CPS). The scale of the horizontal axis is the mass to charge ratio (m/z).

FIG. 33 provides further evidence to demonstrate the m/z 370 ion is monohydroxyl Compound II in each of the three peaks. The mass spectra for the three peaks display molecular and fragment ions consistent with a single hydroxy modification on Compound II. The hydroxy metabolite for the peak at retention time of 18.4 minutes likely occurs on the a-ring as indicated by the m/z 118 fragment for the b-ring (FIG. 33, panel A) in the mass spectrum with the molecular ion of m/z 370. The peaks with retention times of 18.9 and 19.5 minutes are likely both b-ring monohydroxyl modifications of Compound II as suggested by the key fragment ion of m/z 134 in their mass spectra (FIG. 33, panels B and D).

Figure 34:
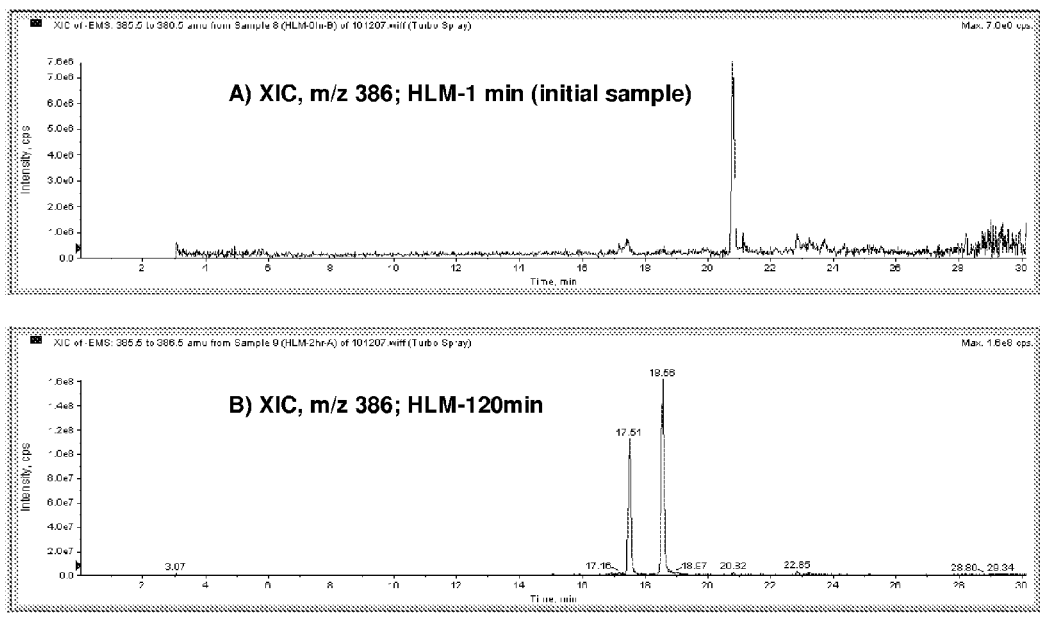
FIG. 34 depicts extracted ion chromatograms (XIC) of di-hydroxylated metabolite (negative ion mode, m/z 386) of Compound II at three different retention times (~17.5 and 18.6 after 120 min, ~20.8 min at initial) in human liver microsomes. The scale of the vertical axis is intensity (CPS). The scale of the horizontal axis is the mass to charge ratio (m/z).
Figure 35:
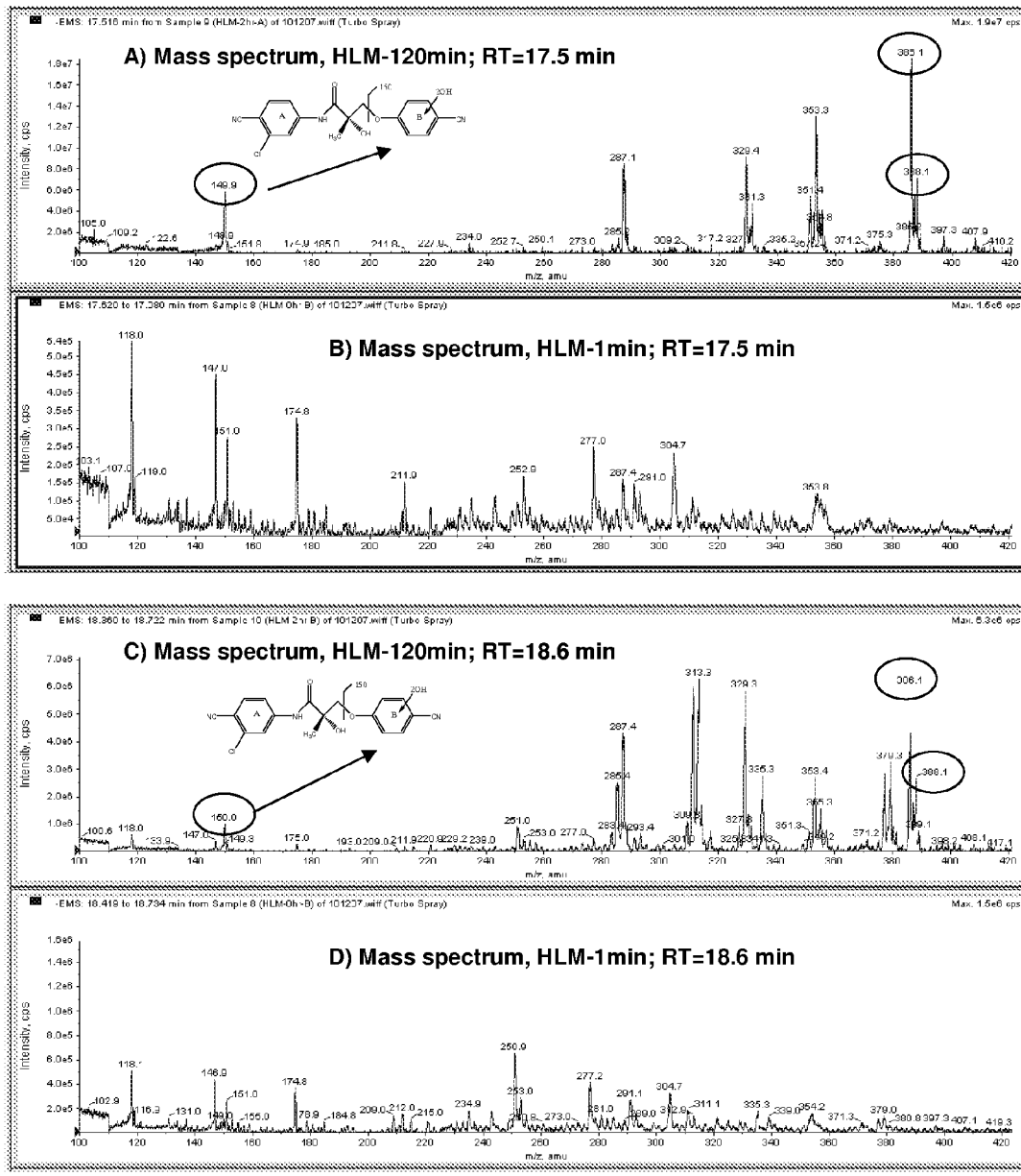
FIG. 35 depicts the mass spectra of di-hydroxylated metabolite (negative ion mode, m/z 386) of Compound II at two different retention times (17.5 and 18.6 min) in human liver microsomes. The scale of the vertical axis is intensity (CPS). The scale of the horizontal axis is the mass to charge ratio (m/z).

In addition to monohydroxylation, dihydroxylation of Compound II is also suggested as a probable biotransformation pathway from liver microsomal incubations. FIG. 34 presents the XIC for ion m/z 386 (representing [M+32]⁻) reveals two distinct chromatographic peaks with retention times of ~17.5 and 18.6 minutes in the final incubation (i.e., HLM-120 min) versus the initial sample (i.e., HLM-1 min). The mass spectra representing these peaks show molecular and fragment ions consistent with the dihydroxyl metabolite at m/z 386 (with the expected isotopic pattern for a chlorine containing compound) and m/z 150, respectively (FIG. 35, panel A and C). That the two baseline resolved peaks in the XIC have the prominent fragment ion at m/z 150 suggests dihydroxylation of the b-ring, likely at two separate ring positions.

Figure 36:
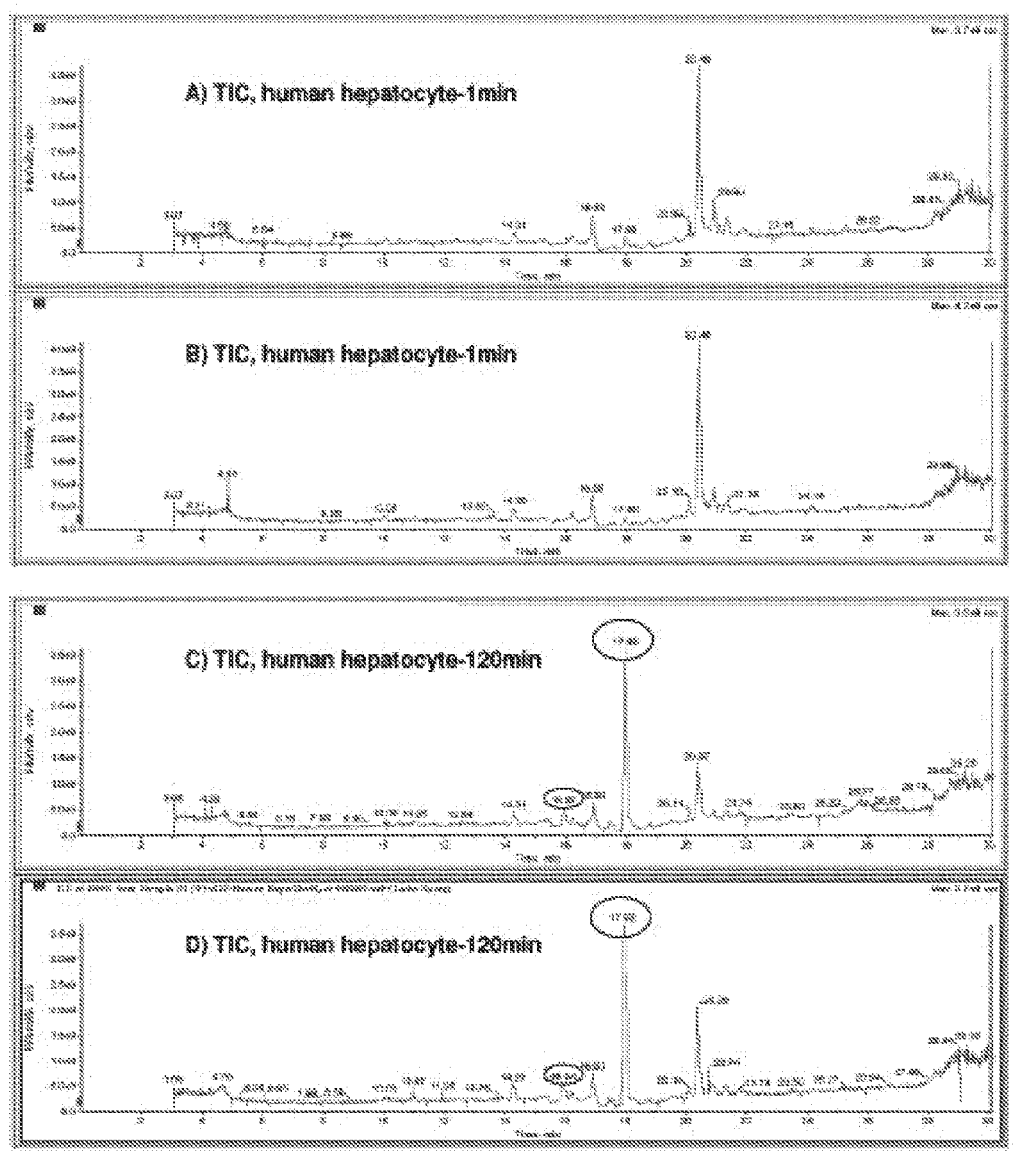
FIG. 36 depicts the total ion chromatogram (TIC) of (–)enhanced MS (EMS) of Compound II incubated in human hepatocytes.

In human hepatocytes, incubation of Compound II also produces several metabolites that may potentially be formed in vivo in humans as well. FIG. 36 illustrates and Phase I and II metabolism of Compound II in human hepatocytes.

Figure 37:
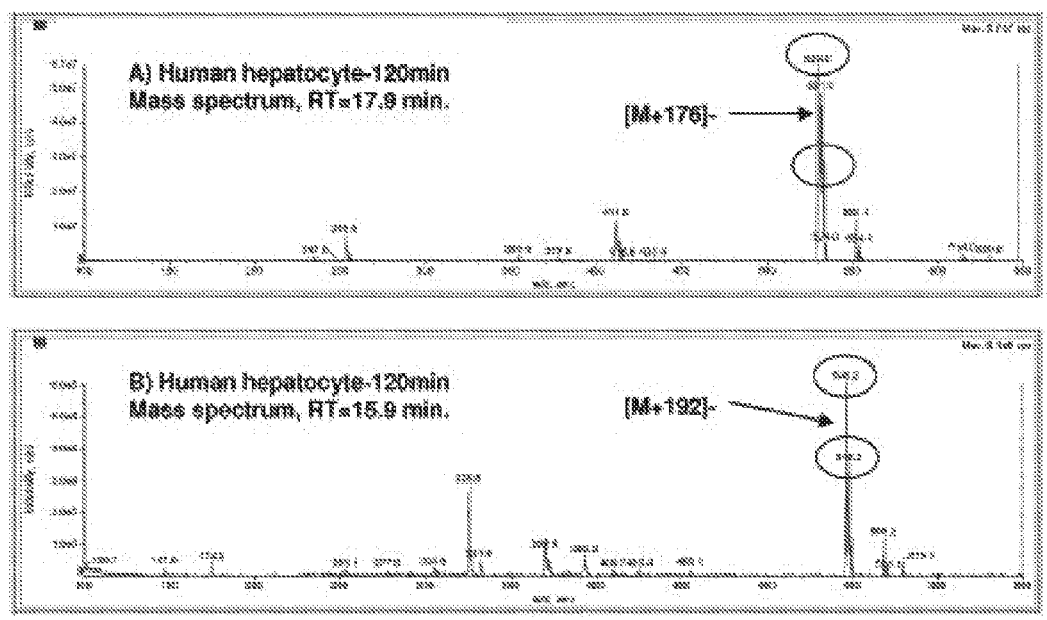
FIG. 37 depicts the mass spectra of metabolite(s) of Compound II in human hepatocytes at 17.9 min.
Figure 38:
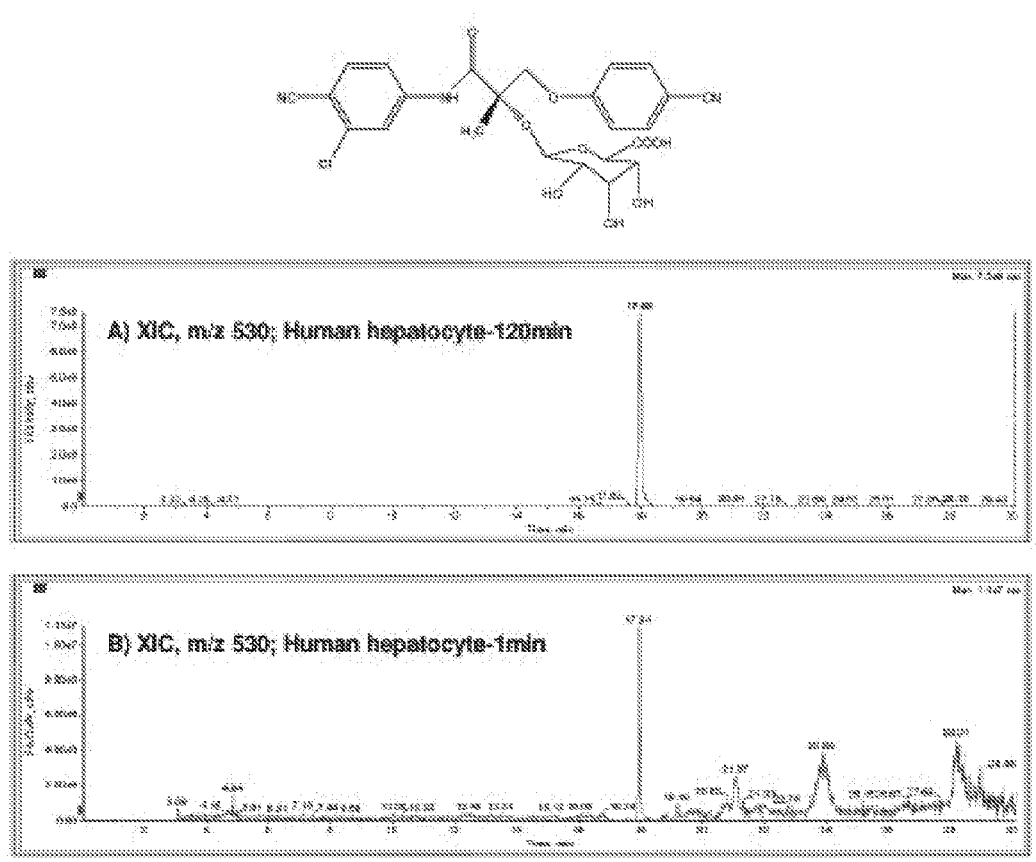
FIG. 38 depicts the extracted ion chromatograms (XIC) at m/z 530 of (–)EMS of Compound II incubated in human hepatocytes and proposed chemical structure of the metabolite at m/z 530.
Figure 39:
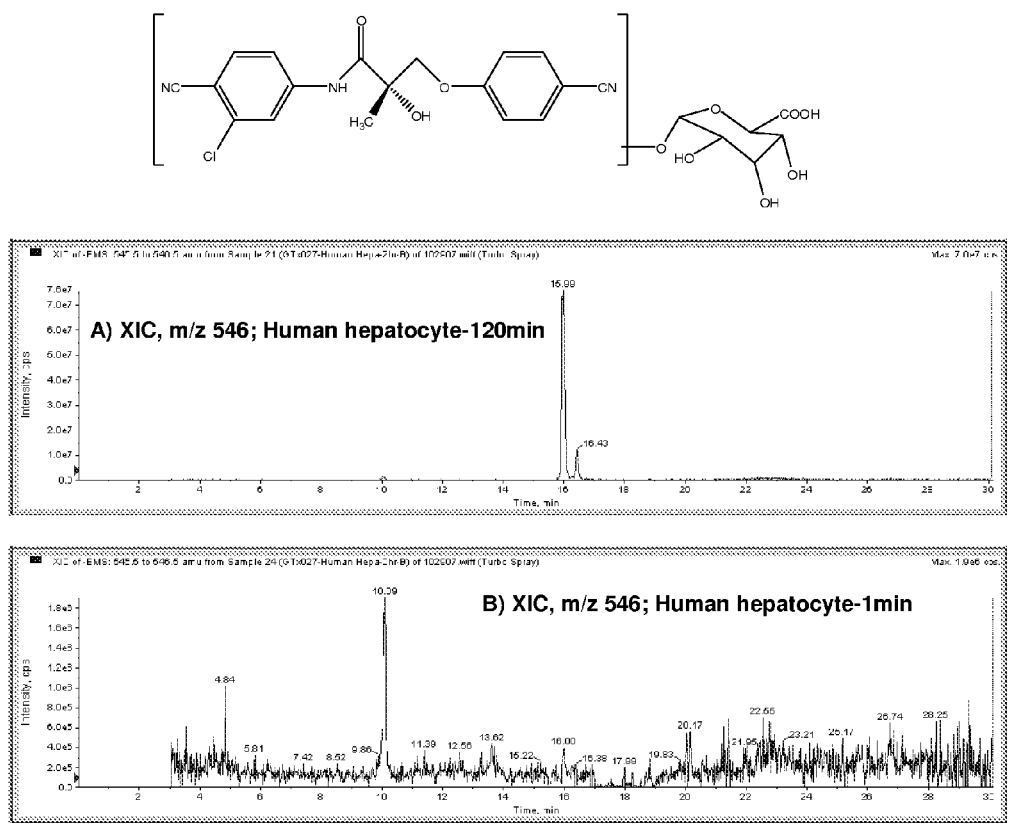
FIG. 39 depicts the extracted ion chromatograms (XIC) at m/z 546 of (–)EMS of Compound II incubated in human hepatocytes and proposed chemical structure of the metabolite at m/z 546.

FIG. 36 shows TIC for the human hepatocyte incubations at initial (i.e., human hepatocyte-1 min) and after 120 minutes incubations at 37° C. (i.e., human hepatocyte-120 min). As for the liver microsome incubations, the peak with retention time of ~20.3 minutes is the unchanged fraction of Compound II. In hepatocytes, though several minor metabolites were formed, the two prevalent peaks noted in the mass chromatograms (TIC) corresponded to retention times of ~15.9 and 17.9 minutes, respectively. Mass spectra for these peaks suggest that the peak at 17.9 minutes is the glucuronide metabolite of Compound II [M+176]⁻ with m/z 530 (FIG. 37, panel A) and the peak at 15.9 minutes is a monohydroxyl glucuronide metabolite of Compound II [M+192]⁻ with m/z 546 (FIG. 37, panel B). By selecting m/z 530 and generating an XIC, the proposed glucuronide metabolite appears to be a highly prevalent product of the Compound II incubation in human hepatocytes (FIG. 38). This metabolite is readily formed as it is present in the initial sample (i.e., HLM-1 min, panel B) though importantly in the initial sample the intensity is significantly lower than after 120 minute incubation in hepatocytes (panel A). Similarly, the XIC for m/z 564 constructed from the TIC for the human hepatocyte incubation suggests a minimum of two possible monohydroxyl glucuronide metabolite species by the two peaks as shown in FIG. 39. Further analyses suggest the b-ring modification with O-glucuronide is favored, though there is evidence that the O-glucuronide occurs on the a-ring as well (data on file, GTx, Inc.).

Figure 40:
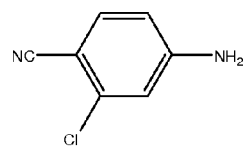
FIG. 40 depict extracted ion chromatograms (XIC) at m/z 151 of (–) EMS of Compound II incubated in human hepatocytes and proposed chemical structure of the metabolite at m/z 151.
Figure 40:
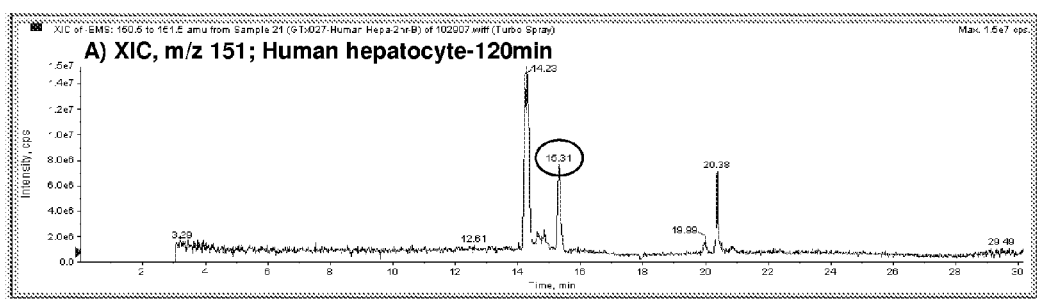
Figure 40:
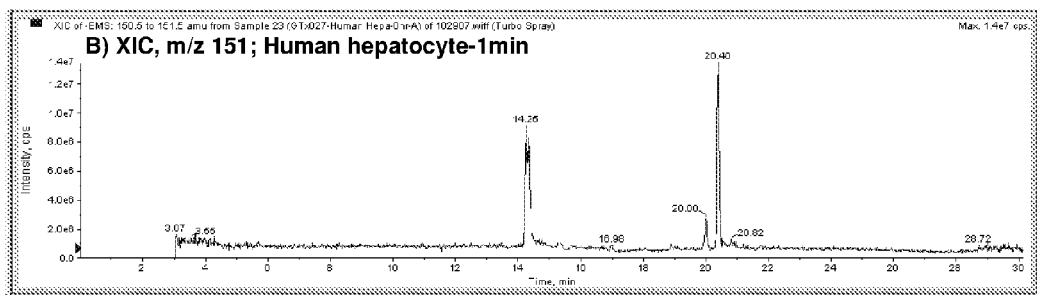
Figure 41:
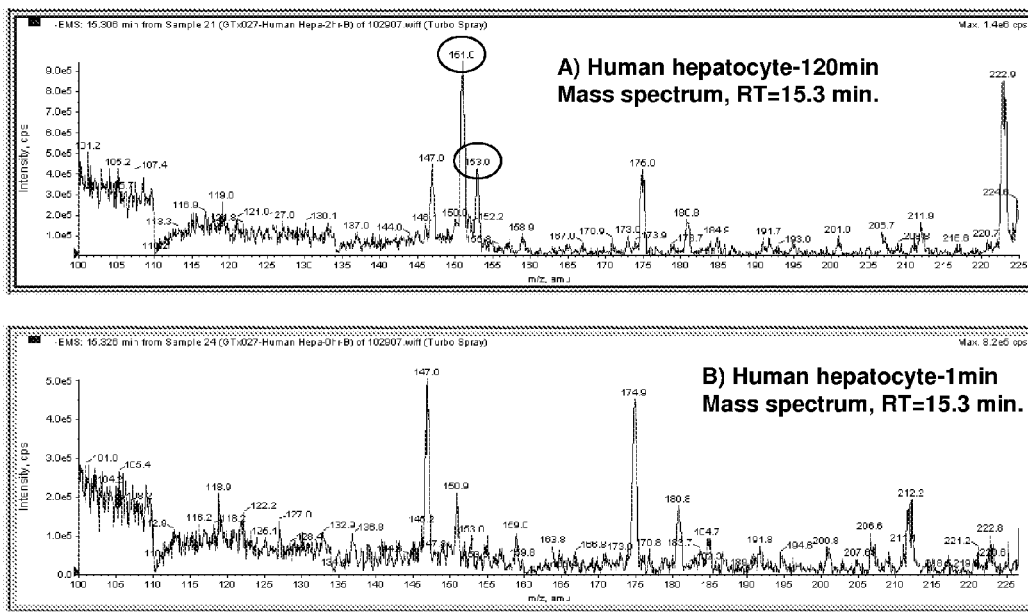
FIG. 41 depicts the mass spectra of metabolite of Compound II at m/z 151 in human hepatocytes.

Another potential biotransformation of Compound II in humans is amide hydrolysis of the a-ring to produce a cyanoaniline derivative as suggested by m/z 151 in XIC from the hepatocyte incubation (FIG. 40, panel A). The mass spectrum for the peak with retention time of 15.3 minutes demonstrates an ion at m/z 151/153, consistent with the cyano-aniline product (a chlorine containing molecule). The m/z ion was not present in the initial sample (FIG. 41, panel B). Although the method is not truly quantitative, based on intensity it is likely that this is an exceedingly low abundance metabolite (compared to glucuronide and O-glucuronide product).

Figure 42:
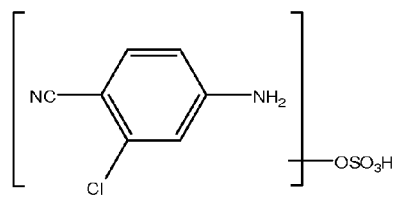
FIG. 42 depicts the extracted ion chromatograms (XIC) at m/z 247 of (–) EMS of Compound II incubated in human hepatocytes and proposed chemical structure of the metabolite at m/z 247.
Figure 42:
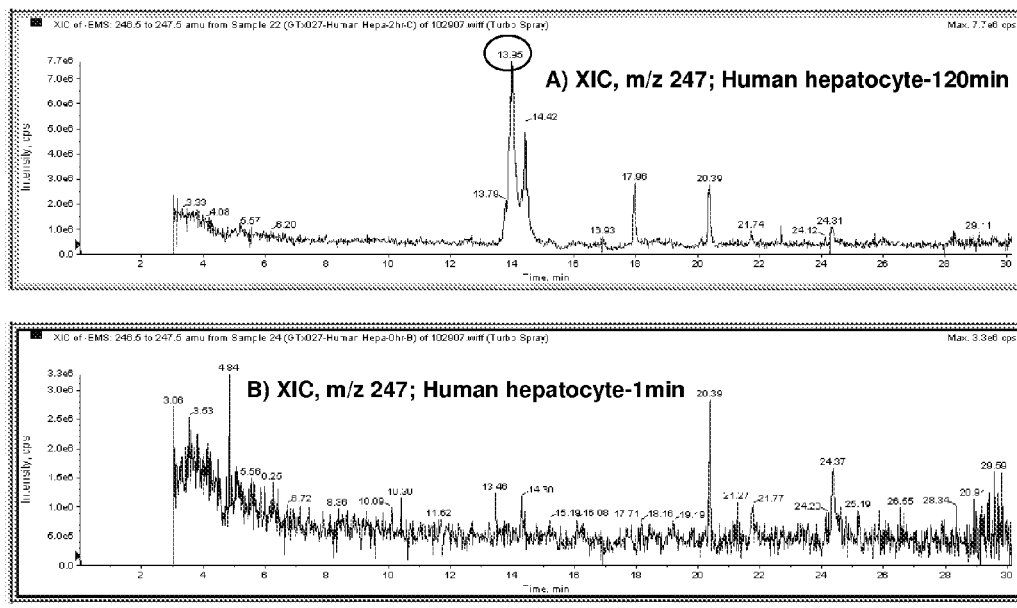
Figure 43:
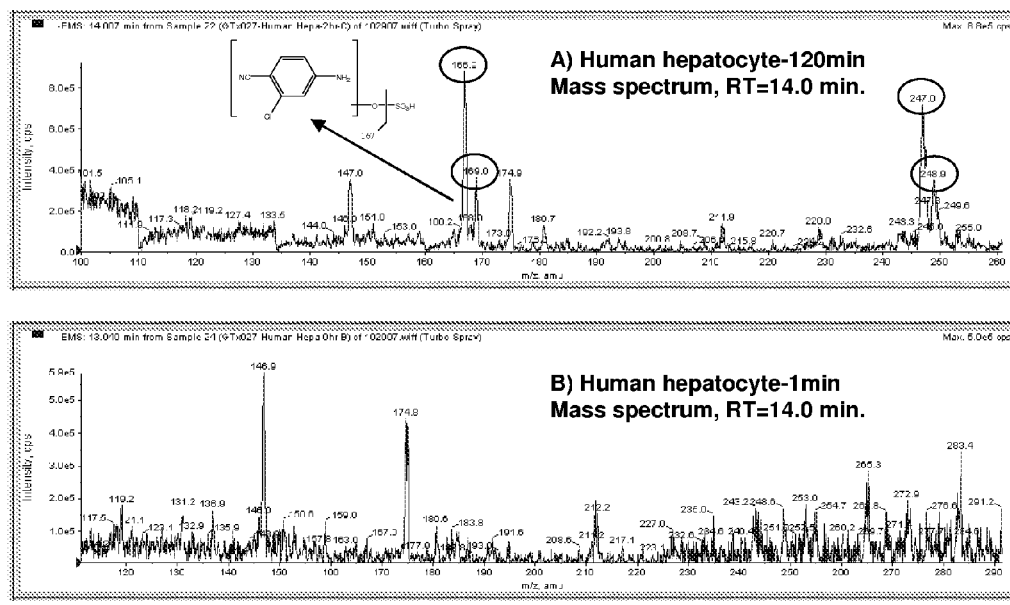
FIG. 43 depicts the mass spectra of metabolite of Compound II at m/z 247 in human hepatocytes.

To further evaluate whether the cyano-aniline or a cyanoaniline containing fragment was generated in the hepatocyte incubations, various further ions were selected by XIC as a potential further biological metabolites of this derivative. m/z 247 represents the [M+96]⁻ for the cyano-aniline derivative. The XIC for m/z 247 reveals a peak at ~14.0 minutes as is shown in FIG. 42. This ion is consistent with a monohydroxyl sulfate metabolite of the cyano-aniline derivative. Further evidence of this metabolite is provided by the mass spectra for the peak at 14.0 minutes at initial and final incubation times, with fragment ions consistent with the O-sulfate product of the cyano-aniline (m/z 247/249 and 167/169) apparent in the spectrum from the final hepatocyte incubation (refer to FIG. 43, panel A and B).

Similar to the experiments in human liver microsomes and hepatocytes, the in vitro metabolism of Compound II has been investigated for several other species including monkey, dog, rat and mouse. Several metabolites are suggested, and Table 10 provides a summary of the various Phase I and II metabolites of Compound II that have been identified in vitro.

Further, the relative abundance of Phase I metabolites has been compared in liver microsomal incubations from the various species. Table 11 is the relative percent of extracted ion chromatograms (XIC) for Phase I metabolites in liver microsomes of human, monkey, dog, rat and mouse.

TABLE 11

Relative Percent of Extracted Ion Chromatogram (XIC) For Phase I Metabolites of Compound II In Liver Microsomes Of Human, Monkey, Dog, Rat, and Mouse.

|  | 370 (1) | 370 (2) | 370 (3) | 386 (1) | 386 (2) | 386 (3) | 386 (4) | 151 |
|---|---|---|---|---|---|---|---|---|
| Human[a] | 2% | 6% | 48% | 17% | N/A | 24% | N/A | 3% |
| Monkey[a] | 2% | 6% | 50% | 11% | N/A | 26% | N/A | 4% |
| Dog[a] | 6% | 3% | 73% | 10% | N/A | 2% | N/A | 6% |
| Rat[a] | 4% | 12% | 47% | 11% | 7% | 14% | 1% | 4% |
| Mouse[a] | 6% | 6% | 59% | 17% | N/A | 6% | 1% | 4% |

[a]Due to potential difference in ionization efficiency for each analyte, values are not absolutely quatitative. (n = 2)

These results suggest that overall the rat had the most active Phase I biotransformation pathways for Compound II. Importantly, no Phase I metabolites were identified in human liver microsomes that were not apparent in the other species. Further, the b-ring monohydroxy metabolite of Compound II [i.e., m/z 370 (3)] is the prominent Phase I metabolite formed in vitro for all of the species evaluated.

Similarly, under Phase I+glucuronidation conditions in microsomes (as presented in Table 12), the glucuronide modification on the chiral center of Compound II (i.e., m/z 530) was favored for all species and the major human metabolites were well represented in other species.

TABLE 10

Phase I & II Hepatic Metabolites of Compound II Identified in vitro

| [M − H]⁻ | Mass Shift from Parent | Possible Metabolic Reactions | Type of Reaction | Proposed site of modification |
|---|---|---|---|---|
| 370 (1) | +16 | Mono-hydroxylation | Phase I | Unknown |
| 370 (2) | +16 |  |  | B-ring |
| 370 (3) |  |  |  |  |
| 386 (1) | +32 | Di-hydroxylation | Phase I | B-ring |
| 386 (3) |  |  |  |  |
| 386 (2) |  |  |  | Unknown |
| 386 (4) |  |  |  |  |
| 450 | +96 | Mono-hydroxylation and sulfation | Phase I & II | Unknown |
| 530 | +176 | Glucuronidation | Phase II | Aliphatic hydroxyl group |
| 546 (1) | +192 | Mono-hydroxylation and glucuronidation | Phase I & II | Unknown |
| 546 (2) | +192 |  |  | Unknown |
| 546 (3) | +192 |  |  | Unknown |
| 546 (4) | +192 |  |  | Unknown |
| 562 (1) | +208 | Di-hydroxylation and glucuronidation | Phase I & II | Unknown |
| 562 (2) | +208 |  |  | Unknown |
| 247 | −107 | Amide hydrolysis and mono-hydroxylation and sulfation of a-ring cleavage product (m/z 151) | Phase I & II | A-ring |
| 151 | −203 | Amide hydrolysis to yield A-ring | Phase I | A-ring |

TABLE 12

Relative Percent of XIC For Phase I and Glucuronide Metabolites of Compound II In Liver Microsomes (+UDPGA) of Human, Monkey, Dog, Rat, and Mouse.

| [M − H]⁻ | Human[a] | Monkey[a] | Dog[a] | Rat[a] | Mouse[a] |
|---|---|---|---|---|---|
| 530 | 75.9% | 48.4% | 37.9% | 58.0% | 59.0% |
| 546 (1) | 18.3% | 31.4% | 36.9% | 18.1% | 20.8% |
| 546 (2) | 3.3% | 7.9% | 2.3% | 6.0% | 2.5% |
| 546 (3) | N/A | 2.0% | N/A | 1.7% | 2.3% |
| 546 (4) | 1.0% | 6.8% | 8.9% | 9.7% | 12.1% |
| 562 (1) | 0.2% | 0.2% | 0.2% | 0.1% | 0.1% |
| 562 (2) | 0.0% | 0.2% | 0.8% | 1.4% | 0.1% |
| 370 (1) | 0.3% | 0.9% | 2.5% | 1.8% | 1.7% |
| 370 (3) | 0.1% | 0.5% | 7.7% | 1.8% | 0.3% |
| 151 | 0.8% | 1.6% | 2.9% | 1.4% | 1.1% |
| Total | 100% | 100% | 100% | 100% | 100% |

Incubations in hepatocytes of various species revealed a slightly different metabolic map (Table 13), with the glucuronide metabolite (m/z 530) most abundant for human, monkey, rat and mouse.

TABLE 13

Relative Percent of XIC For Phase I and II Metabolites of Compound II In Hepatocytes of Human, Monkey, Dog, Rat, and Mouse.

| [M − H]⁻ | Human[a] | Monkey[a] | Dog[a] | Rat[a] | Mouse[a] |
|---|---|---|---|---|---|
| 530 | 88.8% | 62.6% | 9.8% | 44.7% | 85.0% |
| 546 (1) | 6.8% | 17.8% | 21.5% | 11.6% | 7.5% |
| 546 (2) | 0.8% | 2.1% | N/A | 4.1% | 0.4% |
| 546 (3) | N/A | N/A | N/A | 0.1% | 0.4% |
| 546 (4) | N/A | 1.9% | 2.8% | 1.5% | 2.4% |
| 370 (1) | N/A | N/A | 2.4% | 0.3% | 0.2% |
| 370 (3) | 0.1% | 1.2% | 18.5% | 5.9% | 1.1% |
| 562 (2) | N/A | N/A | N/A | 0.4% | N/A |
| 450 | N/A | 2.2% | 17.5% | 28.9% | N/A |
| 151 | 0.5% | 2.2% | 4.7% | 0.9% | 0.8% |
| 247 | 3.0% | 10.1% | 22.8% | 1.6% | 2.0% |
| Total | 100.0% | 100.0% | 100.0% | 100.0% | 100.0% |

However, in dog hepatocytes, monohydroxyl glucuronide and monohydroxyl sulfate metabolites showed greater abundance than in the other species. Still, no metabolites were identified that were unique to the human hepatocyte incubations.

Using the collective data from experiments designed to identify SARM metabolites from biological samples generated under in vitro and in vivo conditions, a metabolite map was created for the SARM series, as is shown in FIG. 44. These potential metabolic transformations are known to occur for SARMs under the stated conditions, however, additional metabolites may potentially occur and the identification of further metabolites will continue.

Example 8

Synthesis of $^{15}N^{13}C$ Labeled A-Ring for Compound I

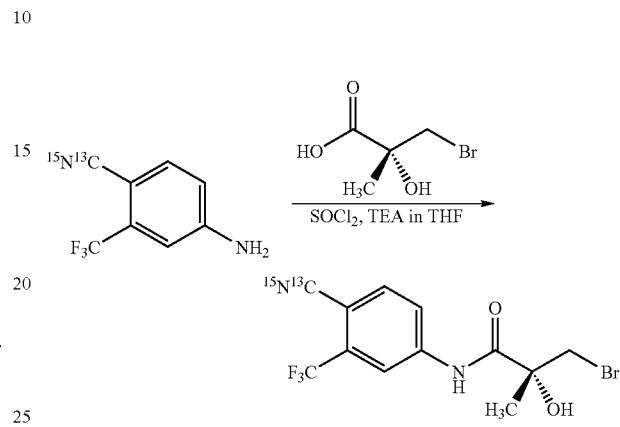

Synthesis of Labeled (2R)-3-Bromo-N-[4-cyano-3-(trifluoromethyl)phenyl]-2-hydroxy-2-methylpropanamide.

Thionyl chloride (46.02 g, 0.39 mol) was added dropwise to a cooled solution (less than 4° C.) of (R)-3-bromo-2-hydroxy-2-methylpropanoic acid (51.13 g, 0.28 mol) in 300 mL of THF under an argon atmosphere. The resulting mixture was stirred for 3 h under the same condition. To this was added Et₃N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H₂O, extracted with EtOAc (2×400 mL). The combined organic extracts were washed with saturated NaHCO₃ solution (2×300 mL) and brine (300 mL). The organic layer was dried over MgSO₄ and concentrated under reduced pressure to give a solid which was purified from column chromatography using CH₂Cl₂/EtOAc (80:20) to give a solid. This solid was recrystallized from CH₂Cl₂/hexane to give 55.8 g (73.9%) of (2R)-3-bromo-N-[4-cyano-3-(trifluoromethyl)phenyl]-2-hydroxy-2-methylpropanamide as a light-yellow solid.

¹H NMR (CDCl₃/TMS) δ 1.66 (s, 3H, CH₃), 3.11 (s, 1H, OH), 3.63 (d, J=10.8 Hz, 1H, CH₂), 4.05 (d, J=10.8 Hz, 1H, CH₂), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M−H]⁻ 349.0. M.p.: 124-126° C.

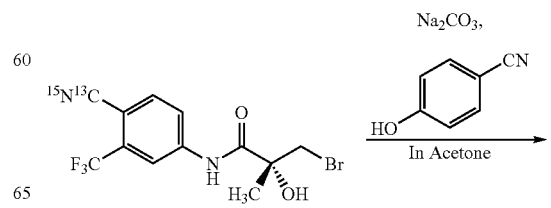

-continued

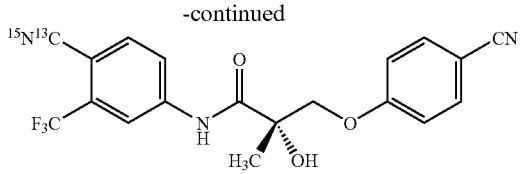

Synthesis of labeled (S)—N-(4-cyano-3-(trifluoromethyl)phenyl)-3-(4-cyanophenoxy)-2-hydroxy-2-methylpropanamide. A mixture of labeled bromoamide ((2R)-3-bromo-N-[4-cyano-3-(trifluoromethyl)phenyl]-2-hydroxy-2-methylpropanamide, 50 g, 0.14 mol), anhydrous $Na_2CO_3$ (59.04 g, 0.43 mol), 4-cyanophenol (25.44 g, 0.21 mol) in 500 mL of acetone was heated to reflux for 3 h and then concentrated under reduced pressure to give a solid. The resulting residue was treated with 500 mL of $H_2O$ and then extracted with EtOAc (2×300 mL). The combined EtOAc extracts were washed with 10% NaOH (4×200 mL) and brine. The organic layer was dried over $MgSO_4$ and then concentrated under reduced pressure to give an oil which was treated with 300 mL of ethanol and an activated carbon. The reaction mixture was heated to reflux for 1 h and then the hot mixture was filtered through Celite. The filtrate was concentrated under reduced pressure to give an oil. This oil was purified by column chromatography using $CH_2Cl_2$/EtOAc (80:20) to give an oil which was crystallized from $CH_2Cl_2$/hexane to give 33.2 g (59.9%) of (S)—N-(4-cyano-3-(trifluoromethyl)phenyl)-3-(4-cyanophenoxy)-2-hydroxy-2-methylpropanamide as a colorless solid (a cotton type).

$^1$H NMR ($CDCl_3$/TMS) δ 1.63 (s, 3H, $CH_3$), 3.35 (s, 1H, OH), 4.07 (d, J=9.04 Hz, 1H, CH), 4.51 (d, J=9.04 Hz, 1H, CH), 6.97-6.99 (m, 2H, ArH), 7.57-7.60 (m, 2H, ArH), 7.81 (d, J=8.55 Hz, 1H, ArH), 7.97 (dd, J=1.95, 8.55 Hz, 1H, ArH), 8.12 (d, J=1.95 Hz, 1H, ArH), 9.13 (bs, 1H, NH). Calculated Mass: 389.10, [M–H]$^-$ 388.1. Mp: 92-94° C.

Thus an isotope labeled compound of formula I was synthesized in one embodiment, according to the method hereinabove.

Example 9

Synthesis of Deuterium Labeled B-Ring for Compound I

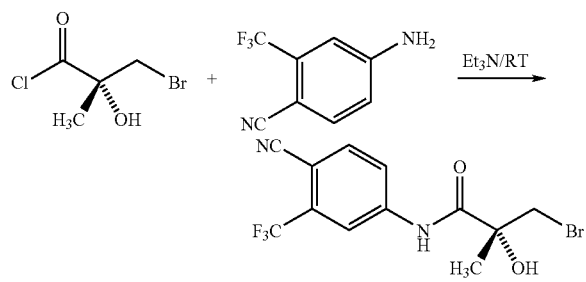

Synthesis of (2R)-3-Bromo-N-[4-cyano-3-(trifluoromethyl)phenyl]-2-hydroxy-2-methylpropanamide. Thionyl chloride (46.02 g, 0.39 mol) was added dropwise to a cooled solution (less than 4° C.) of (R)-3-bromo-2-hydroxy-2-methylpropanoic acid (51.13 g, 0.28 mol) in 300 mL of THF under an argon atmosphere. The resulting mixture was stirred for 3 h under the same condition. To this was added $Et_3N$ (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of $H_2O$, extracted with EtOAc (2×400 mL). The combined organic extracts were washed with saturated $NaHCO_3$ solution (2×300 mL) and brine (300 mL). The organic layer was dried over $MgSO_4$ and concentrated under reduced pressure to give a solid which was purified from column chromatography using $CH_2Cl_2$/EtOAc (80:20) to give a solid. This solid was recrystallized from $CH_2Cl_2$/hexane to give 55.8 g (73.9%) of (2R)-3-bromo-N-[4-cyano-3-(trifluoromethyl)phenyl]-2-hydroxy-2-methylpropanamide as a light-yellow solid.

$^1$H NMR ($CDCl_3$/TMS) δ 1.66 (s, 3H, $CH_3$), 3.11 (s, 1H, OH), 3.63 (d, J=10.8 Hz, 1H, $CH_2$), 4.05 (d, J=10.8 Hz, 1H, $CH_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M–H]$^-$ 349.0. M.p.: 124-126° C.

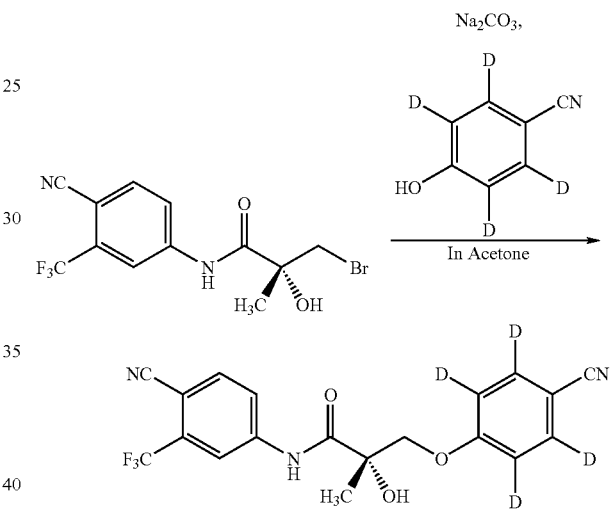

Synthesis of Deuterated (S)—N-(4-cyano-3-(trifluoromethyl)phenyl)-3-(4-cyanophenoxy)-2-hydroxy-2-methylpropanamide. A mixture of bromoamide ((2R)-3-bromo-N-[4-cyano-3-(trifluoromethyl)phenyl]-2-hydroxy-2-methylpropanamide, 50 g, 0.14 mol), anhydrous $Na_2CO_3$ (59.04 g, 0.43 mol), and 4-cyanophenol-$d_4$ (25.44 g, 0.21 mol) in 500 mL of acetone was heated to reflux for 3 h and then concentrated under reduced pressure to give a solid. The resulting residue was treated with 500 mL of $H_2O$ and then extracted with EtOAc (2×300 mL). The combined EtOAc extracts were washed with 10% NaOH (4×200 mL) and brine. The organic layer was dried over $MgSO_4$ and then concentrated under reduced pressure to give an oil which was treated with 300 mL of ethanol and an activated carbon. The reaction mixture was heated to reflux for 1 h and then the hot mixture was filtered through Celite. The filtrate was concentrated under reduced pressure to give an oil. This oil was purified by column chromatography using $CH_2Cl_2$/EtOAc (80:20) to give an oil which was crystallized from $CH_2Cl_2$/hexane to give 33.2 g (59.9%) of deuterated (S)—N-(4-cyano-3-(trifluoromethyl)phenyl)-3-(4-cyanophenoxy)-2-hydroxy-2-methylpropanamide as a colorless solid (a cotton type).

$^1$H NMR ($CDCl_3$/TMS) δ 1.63 (s, 3H, $CH_3$), 3.35 (s, 1H, OH), 4.07 (d, J=9.04 Hz, 1H, CH), 4.51 (d, J=9.04 Hz, 1H, CH), 6.97-6.99 (m, 2H, ArH), 7.57-7.60 (m, 2H, ArH), 7.81

(d, J=8.55 Hz, 1H, ArH), 7.97 (dd, J=1.95, 8.55 Hz, 1H, ArH), 8.12 (d, J=1.95 Hz, 1H, ArH), 9.13 (bs, 1H, NH). Calculated Mass: 389.10, [M−H]⁻ 388.1. Mp: 92-94° C.

Thus a deuterated compound of formula I was synthesized in one embodiment, according to the method hereinabove.

Example 10

Synthesis of Deuterium Labeled B-Ring for Compound II

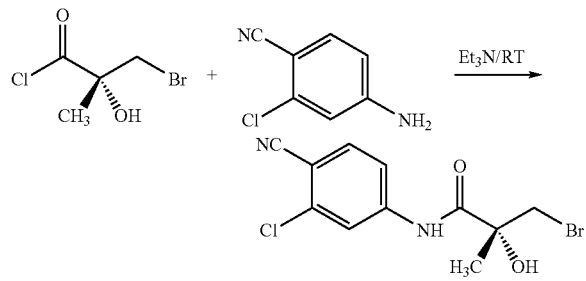

Synthesis of (2R)-3-bromo-N-(3-chloro-4-cyanophenyl)-2-hydroxy-2-methylpropanamide. Thionyl chloride (7.8 g, 65.5 mmol) was added dropwise to a cooled solution (less than 4° C.) of (R)-3-bromo-2-hydroxy-2-methylpropanoic acid (9.0 g, 49.2 mol) in 50 mL of THF under an argon atmosphere. The resulting mixture was stirred for 3 h under the same condition. To this was added Et₃N (6.6 g, 65.5 mol) and stirred for 20 min under the same condition. After 20 min, 4-amino-2-chlorobenzonitrile (5.0 g, 32.8 mmol) and 100 mL of THF were added and then the mixture was allowed to stir overnight at room temperature. The solvent was removed under reduced pressure to give a solid which was treated with 100 mL of H₂O, extracted with EtOAc (2×150 mL). The combined organic extracts were washed with saturated NaHCO₃ solution (2×100 mL) and brine (300 mL), successively. The organic layer was dried over MgSO₄ and concentrated under reduced pressure to give a solid which was purified from column chromatography using EtOAc/hexane (50:50) to give 7.7 g (49.4%) of target compound as a brown solid.

¹H NMR (CDCl₃/TMS) δ 1.7 (s, 3H, CH₃), 3.0 (s, 1H, OH), 3.7 (d, 1H, CH), 4.0 (d, 1H, CH), 7.5 (d, 1H, ArH), 7.7 (d, 1H, ArH), 8.0 (s, 1H, ArH), 8.8 (s, 1H, NH). MS:342.1 (M+23). Mp 129° C.

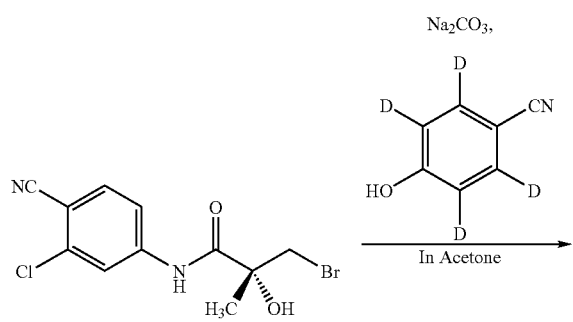

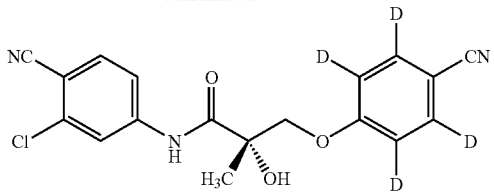

Synthesis of Deuterated (S)—N-(3-chloro-4-cyanophenyl)-3-(4-cyanophenoxy)-2-hydroxy-2-methylpropanamide. A mixture of bromoamide (2.0 g, 6.3 mmol), anhydrous K₂CO₃ (2.6 g, 18.9 mmol) in 50 mL of acetone was heated to reflux for 2 h and then concentrated under reduced pressure to give a solid. The resulting solid was treated with deuterated 4-cyanophenol (1.1 g, 9.5 mmol) and anhydrous Na₂CO₃ (1.7 g, 12.6 mmol) in 50 mL of acetone was heated to reflux for 3 h and then concentrated under reduced pressure to give a solid. The residue was treated with 100 mL of H₂O and then extracted with EtOAc (2×100 mL). The combined EtOAc extracts were washed with 10% NaOH (4×100 mL) and brine, successively. The organic layer was dried over MgSO₄ and then concentrated under reduced pressure to give an oil which was purified by column chromatography using EtOAc/hexane (50:50) to give a solid. The solid was recrystallized from CH₂Cl₂/hexane to give 1.4 g (61.6%) of deuterated (S)—N-(3-chloro-4-cyanophenyl)-3-(4-cyanophenoxy)-2-hydroxy-2-methylpropanamide as a colorless solid.

¹H NMR (CDCl₃/TMS) δ 1.61 (s, 3H, CH₃), 3.25 (s, 1H, OH), 4.06 (d, J=9.15 Hz, 1H, CH), 4.50 (d, J=9.15 Hz, 1H, CH), 6.97-6.99 (m, 2H, ArH), 7.53-7.59 (m, 4H, ArH), 7.97 (d, J=2.01 Hz, 1H, ArH), 8.96 (s, 1H, NH). Calculated Mass: 355.1, [M+Na]+378.0. Mp: 103-105° C.

Thus an isotope labeled compound of formula II was synthesized, representing one embodiment of this invention, a method of which is described hereinabove.

It will be appreciated by a person skilled in the art that the present invention is not limited by what has been particularly shown and described hereinabove.

What is claimed is:

1. An isolated metabolite of a selective androgen receptor modulator (SARM) compound represented by the following structure:

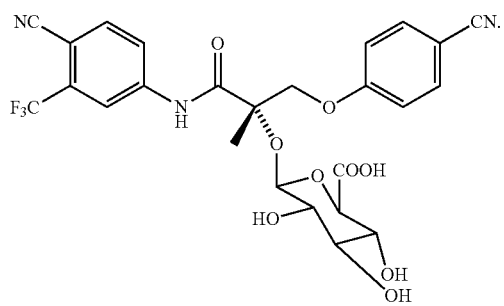

2. The metabolite of claim 1, wherein said metabolite is an optical isomer, pharmaceutically acceptable salt, or any combination thereof.

* * * * *